(12) United States Patent
Puskás et al.

(10) Patent No.: US 10,287,265 B2
(45) Date of Patent: May 14, 2019

(54) ENANTIOMERS OF 8-HYDROXYQUINOLINE DERIVATIVES AND THE SYNTHESIS THEREOF

(71) Applicants: AVIDIN Co. Ltd., Szeged (HU); SONEAS Research Co. Ltd., Budapest (HU); Synaging SAS, Nancy (FR)

(72) Inventors: László Puskás, Szeged (HU); István Kanizsai, Szeged (HU); Thierry Pillot, Crevic (FR); Márió Gyuris, Szeged (HU); András Szabó, Budapest (HU); Ferenc Takács, Monor (HU); László Hackler, Szeged (HU)

(73) Assignees: AVIDIN Co. Ltd., Szeged (HU); SONEAS Research Co. Ltd., Budapest (HU); Synaging SAS, Nancy (FR)

( * ) Notice: Subject to any disclaimer, the term of this patent is extended or adjusted under 35 U.S.C. 154(b) by 0 days.

(21) Appl. No.: 15/065,385

(22) Filed: Mar. 9, 2016

(65) Prior Publication Data
US 2017/0197936 A1    Jul. 13, 2017

Related U.S. Application Data

(63) Continuation of application No. PCT/HU2016/000012, filed on Mar. 7, 2016.

(30) Foreign Application Priority Data

Mar. 9, 2015 (HU) ................... 1500098

(51) Int. Cl.
C07D 401/12 (2006.01)
(52) U.S. Cl.
CPC .................. *C07D 401/12* (2013.01)
(58) Field of Classification Search
CPC ... C07D 215/26; C07D 215/28; C07D 401/12
See application file for complete search history.

(56) References Cited

U.S. PATENT DOCUMENTS 7,947,712 B2 *   5/2011   Bursavich ............ C07D 215/26
                                                                                514/312
8,729,097 B2 *   5/2014   Liu ........................ A61K 31/47
                                                                                514/312

(Continued)

FOREIGN PATENT DOCUMENTS

CN        104 744 439         7/2015
WO     WO 2008/116092 A1    9/2008
(Continued)

OTHER PUBLICATIONS

CAS Abstract US 2017/0197936 (2017).*
J.H. Cardellina et al., 2 ACS Medicinal Chemistry Letters, 396-401 (2011).*

(Continued)

*Primary Examiner* — Alexander R Pagano
(74) *Attorney, Agent, or Firm* — Pearl Cohen Zedek Latzer Baratz LLP

(57) ABSTRACT

Our invention relates to novel enantiomer derivatives of 8-hydroxyquinoline derivatives with general formula (I) and (II) and the synthesis thereof and pharmaceutically acceptable salts and metal complexes thereof, and the medicinal and/or pharmaceutical compositions comprising these compounds.

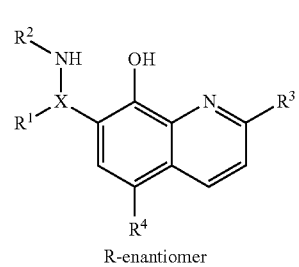

R-enantiomer

I

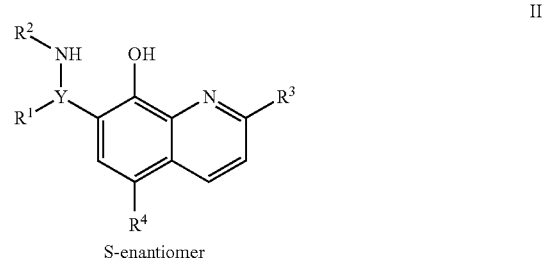

S-enantiomer

II

Figure 1:
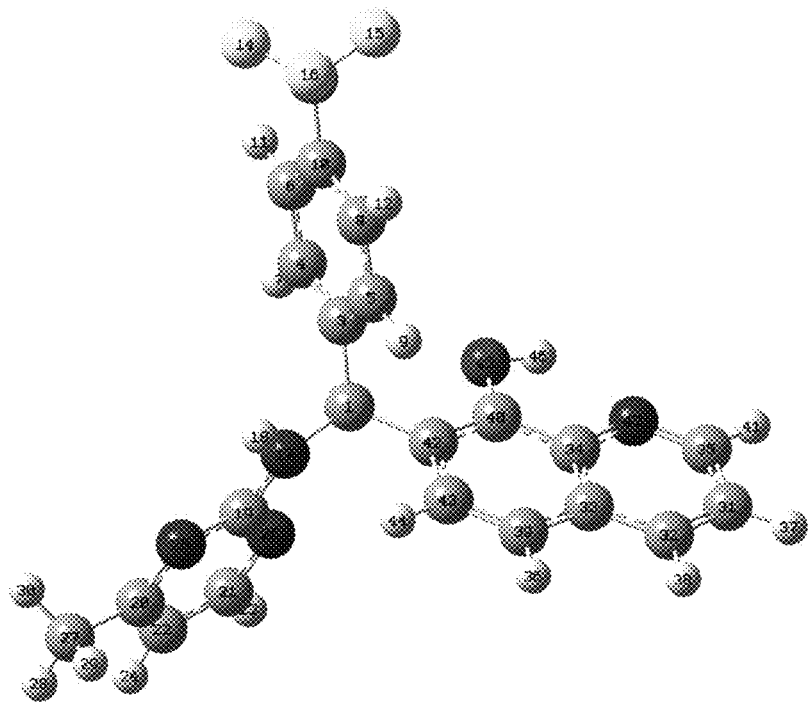

The essence of the subject matter of the invention relates to the fact that prior art discloses the biological effect and characteristics only of the racemic products, the novel enantiomer derivatives according to the invention appear in our application for the first.

The subject matter of the invention furthermore relates to a novel, stereoselective synthesis for the preparation of the novel enantiomer derivatives according to the invention. The novel medicinal and/or pharmaceutical compositions comprising these enantiomers are suitable for the treatment of the named diseases, and the enanatiomers are used for manufacture of these compositions. These applications for manufacture of the compositions are also the subject matters of the invention. The compounds according to the invention can be used preferably as cytoprotective, neuroprotective, cardioprotective, anxiolytic and antidepressant agent for treatment of neuropsychiatric and neurologic diseases and diseases in connections with transplantations and with ischemia and reperfusion injuries thereof, and inhibition of organ, advantageously skin graft rejection. According to our studies the R-enantiomer has either sole or high biological effect in some cases.

6 Claims, 13 Drawing Sheets
(10 of 13 Drawing Sheet(s) Filed in Color)

(56) References Cited

U.S. PATENT DOCUMENTS

| | | | | |
|---|---|---|---|---|
| 8,871,937 | B2* | 10/2014 | Puskas | C07D 215/26 546/159 |
| 9,273,031 | B2* | 3/2016 | Errico | C07K 16/44 |
| 9,695,157 | B2* | 7/2017 | Wilson | A61K 31/47 |
| 2003/0180321 | A1 | 9/2003 | Bertozzi | |
| 2008/0269213 | A1* | 10/2008 | Bursavich | C07D 215/26 514/235.2 |
| 2012/0196853 | A1* | 8/2012 | Durrenberger | C07D 215/26 514/232.5 |
| 2013/0096159 | A1* | 4/2013 | Maloney | C07D 215/28 514/314 |
| 2013/0131096 | A1* | 5/2013 | Puskas | C07D 215/26 514/275 |

FOREIGN PATENT DOCUMENTS

| | | | | |
|---|---|---|---|---|
| WO | WO 2010/042163 | A2 | 4/2010 | |
| WO | WO-2010042163 | A2* | 4/2010 | A61K 31/47 |
| WO | WO-2010068767 | A1* | 6/2010 | A61K 31/47 |
| WO | WO-2011022721 | A1* | 2/2011 | A61K 31/415 |
| WO | WO 2011/106226 | A2 | 9/2011 | |
| WO | WO 2011/148208 | A1 | 12/2011 | |
| WO | WO 2013063458 | A2 | 5/2013 | |
| WO | WO 2016/020892 | A1 | 2/2016 | |

OTHER PUBLICATIONS

P. kumara et al., 5 RSC Advances, 69493-69501 (2015).*
V. Kenyon et al., 54 Journal of Medicinal Chemistry, 5485-5497 (2011).*
Cardellina H.J. et al., Separation of Betti Reaction Product Enantiomers: Absolute Configuration and Inhibition of Botulinum Neurotoxin A, ACS Med. Chem. Letters, vol. 2, No. 5, pp. 396-401 (May 2011).

Cimarelli et al., Solvent-Free Asymmetric Aminoalkylation of Electron-Rich Aromatic Compounds: Stereoselective Synthesis of Aminoalkylnaphthols by Crystallization-Induced Asymmetric Transformation, J. Org. Chem., vol. 66, No. 14, pp. 4759-4765 (Jan. 2001).

Liu et al., Novel Hybrid Virtual Screening Protocol Based on Molecular Docking and Structure-Based Pharmacophore for Discovery of Methionyl-tRNA Synthetase Inhibitors as Antibacterial Agents, Int. J. Mol. Sci., vol. 14, No. 7, pp. 14225-14239 (Jul. 2013).

Lu et al., Discovery of a Nanomolar Inhibitor of the Human Murine Double Minute 2 (MDM2)-p53 Interaction through an Integrated, Virtual Database Screening Strategy, J. Med. Chem., vol. 49, No. 13, pp. 3759-3762 (Jul. 2006).

Smirnova et al., Utilization of an in Vivo Reporter for High Throughput Identification of Branched Small Molecule Regulators of Hypoxic Adaptation. Chemistry & Biology, vol. 17, No. 4, pp. 380-391, Apr. 23, 2010.

Tomlinson et al., A Chemical Genomic Approach Identifies Matrix Metalloproteinases as Playing an Essential and Specific Role in Xenopus Melanophore Migration, Chemistry & Biology, vol. 16, No. 1, pp. 93-104, Jan. 30, 2009.

Wang et al., Predicting dual-targeting anti-influenza agents using mufti-models, Molecular Diversity, vol. 19, No. 1, pp. 123-134 (Oct. 2014).

Search Report for Hungarian Patent Application No. HUP1000243 A, dated Jul. 20, 2016.

International Search Report of PCT Patent Application No. PCT/HU2016/000012, dated Aug. 5, 2018.

* cited by examiner

C3-C1-N17-C19: $\theta_1$     C4-C3-C1-N17: $\theta_3$
C1-N17-C19-C25: $\theta_2$     C3-C1-C42-C40: $\theta_4$
C42-C40-O45-H46: $\theta_5$

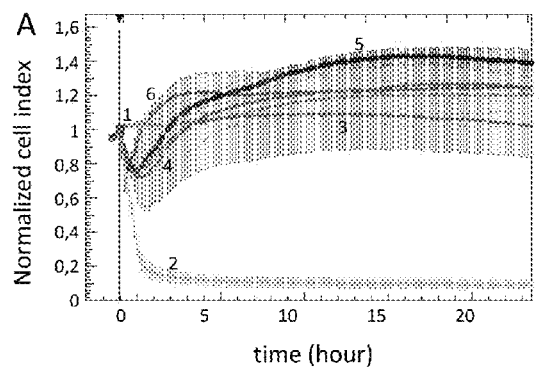
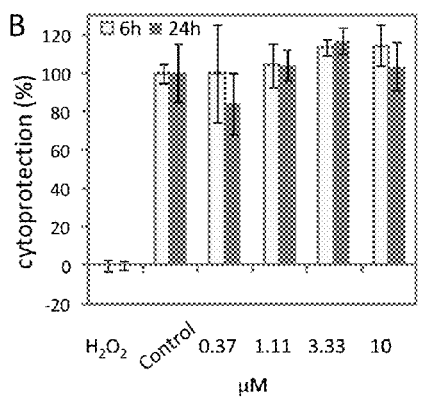
Fig. 6A                    Fig. 6B
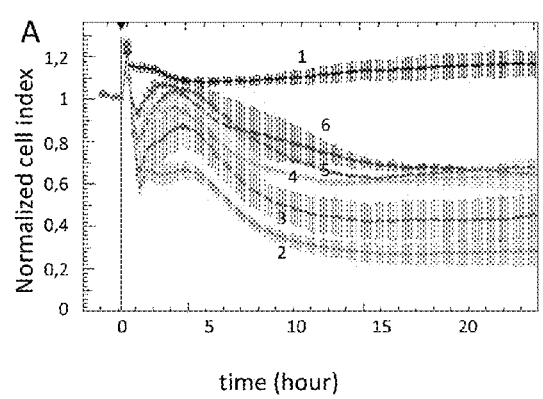
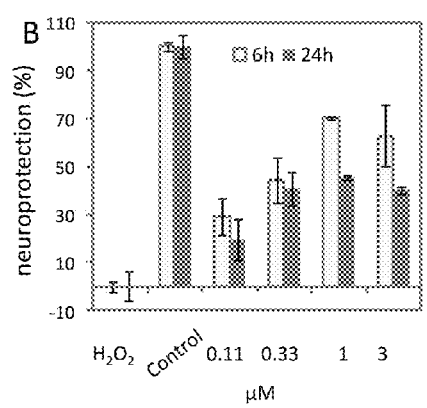
Fig. 7A                    Fig. 7B

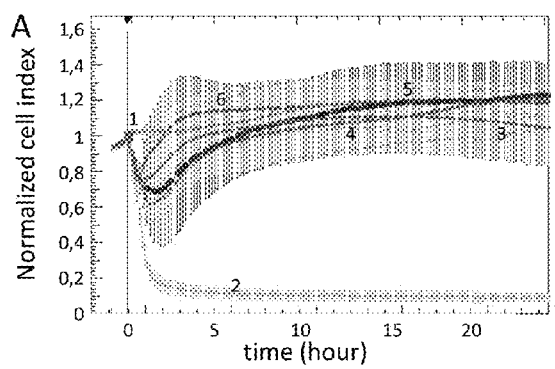 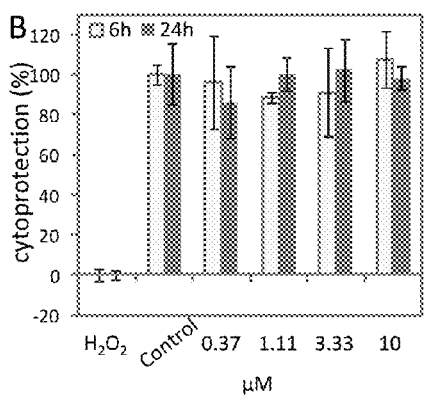
Fig. 8A  Fig. 8B
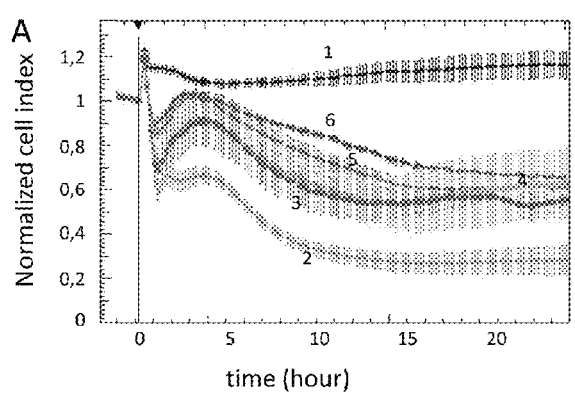 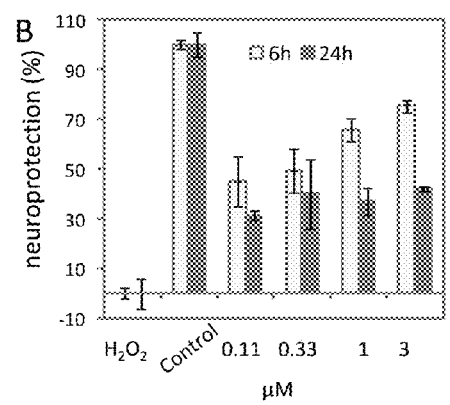
Fig. 9A  Fig. 9B

Example compound #9

ENANTIOMERS OF 8-HYDROXYQUINOLINE DERIVATIVES AND THE SYNTHESIS THEREOF

Our invention relates to novel R-enantiomeric derivatives of 8-hydroxyquinoline derivatives of general formula (I) and novel S-enantiomeric derivatives of 8-hydroxyquinoline derivatives of general formula (II), and pharmaceutically acceptable salts and complexes with divalent or polyvalent metals, advantageously iron, copper or zinc complexes thereof,

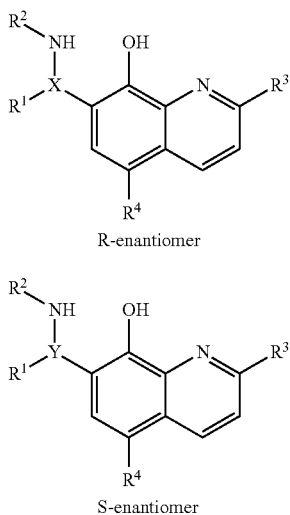

R-enantiomer

S-enantiomer wherein
in general formulas (I) and (II)
$R^1$ is a lower alkyl group, lower cycloalkyl group, aryl group, aralkyl group or six membered heteroaryl or heteroaralkyl group wherein said cyclic groups are optionally substituted at the ortho, meta or para positions with one, two, three or four electron withdrawing groups or electron donating groups or optionally substituted five membered heteroaryl or heteroaralkyl group wherein the five or six membered heteroaryl or heteroaralkyl groups comprising one, two or three nitrogen; oxygen or sulfur atoms or combinations thereof;
$R^2$ is a hydrogen atom; aryl group; or six membered heteroaryl group wherein said cyclic groups are optionally substituted at the ortho; meta or para positions with one, two, three or four electron withdrawing groups or electron donating groups or optionally substituted five membered heteroaryl group wherein the five or six membered heteroaryl groups comprising one, two or three nitrogen; oxygen or sulfur atoms or combinations thereof;
$R^3$ represents a hydrogen atom; lower alkyl group; —$CH_2F$; —$CHF_2$; —$CF_3$; —$CH_2CH_2F$; —$CH_2CHF_2$; —$CH_2CF_3$; —$CH_2OR^5$; —$CH_2CH_2OR^6$; or —$CH_2$—$NR^7R^8$ group;
$R^4$ represents a hydrogen atom; halogen atom; methylthio group; methylsulfinyl group; methylsulfonyl group; or azido group;
$R^5$ represents a hydrogen atom; or lower alkyl group;
$R^6$ represents a hydrogen atom; or lower alkyl group;
$R^7$ represents a hydrogen atom; or lower alkyl group;
$R^8$ represents a hydrogen atom; or lower alkyl group;
$R^7$ and $R^8$ represents jointly —$(CH_2)_n$— group; or —$CH_2CH_2OCH_2CH_2$— group or —$CH_2CH_2SCH_2CH_2$— group or —$CH_2CH_2NR^9CH_2CH_2$— group, wherein
n is 4, 5 or 6;
$R^9$ represents a lower alkyl group; or —$COR^{10}$ group,
$R^{10}$ represents a hydrogen atom; lower alkyl group; methoxy group; or ethoxy group;
in the general formula (I)
X represents a hydrogen substituted C atom with "R" configuration;
in the general formula (II)
Y represents a hydrogen substituted C atom with "S" configuration;
with the proviso that
$R^1$ cannot represent non-substituted phenyl group, in case
$R^2$ represents a non-substituted phenyl group; or non-substituted 2-pyridyl group; or 4-carboxyphenyl group; or 2-carboxyphenyl group;
$R^3$ represents a hydrogen atom or methyl group;
$R^4$ represents hydrogen atom or chlorine substituent;
and
$R^1$ cannot represent 3,4-dimethylphenyl group, in case
$R^2$ represents a non-substituted 2-pyridyl group;
$R^3$ represents methyl group and
$R^4$ a hydrogen atom;
and
$R^1$ cannot represent 2-furyl group, in case
$R^2$ represents a non-substituted 2-pyridyl group;
$R^3$ represents a hydrogen atom and
$R^4$ represents a chlorine substituent
and
$R^1$ cannot represent a non-substituted 2-pyridyl group, in case
$R^2$ represents 5-methylisoxazol-3-yl group
$R^3$ represents a hydrogen atom
$R^4$ represents a hydrogen atom The subject matter of the invention furthermore relates advantageously to novel R-enantiomeric derivatives of 8-hydroxyquinoline derivatives of general formula (I') and novel S-enantiomeric derivatives of 8-hydroxyquinoline derivatives of general formula (II'), and pharmaceutically acceptable salts and complexes with divalent or polyvalent metals, advantageously iron, copper or zinc complexes thereof,

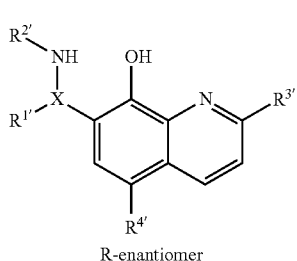

R-enantiomer

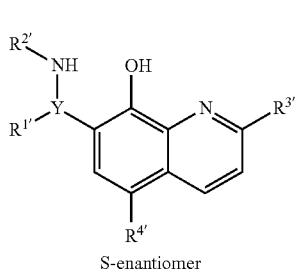

S-enantiomer wherein
in general formulas (I') and (II')
$R^{1'}$ represents an aryl group substituted with an electron withdrawing group in meta or para position, or an aryl group substituted with an electron donating group in ortho, meta or para position; or a double-substituted aryl group with electron withdrawing groups in meta and para positions; or an aryl group double substituted with electron withdrawing groups in ortho and para positions; or a substituted or unsubstituted heteroaryl group;

$R^{2'}$ represents an aryl group substituted with an electron withdrawing group in para position, or an aryl group substituted with an electron donating group in ortho, meta or para position; or an unsubstituted heteroaromatic group or a heteroaromatic or aryl group substituted with alkyl group and/or with electron withdrawing groups in ortho, meta or para positions;

$R^{3'}$ represents advantageously a hydrogen atom
$R^{4'}$ represents advantageously a hydrogen atom and
in general formula (I')
X represents a hydrogen substituted C atom with "R" configuration;
In general formula (II')
Y represents a hydrogen substituted C atom with "S" configuration.

The subject matter of the invention furthermore relates advantageously to novel R-enantiomeric derivatives of 8-hydroxyquinoline derivatives of general formula (I") and novel S-enantiomeric derivatives of 8-hydroxyquinoline derivatives of general formula (II") and pharmaceutically acceptable salts and complexes with divalent or polyvalent metals, advantageously iron, copper or zinc complexes thereof,

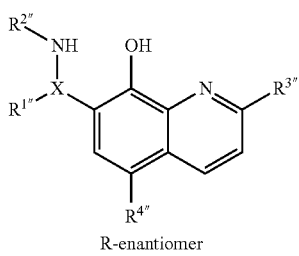
R-enantiomer

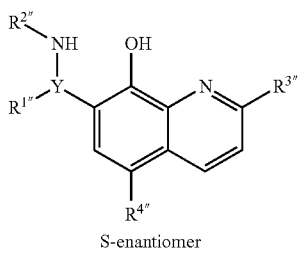
S-enantiomer wherein
in general formulas (I") and (II")
$R^{1''}$ represents advantageously a phenyl or pyridyl group optionally single or double substituted with a trifluoromethyl group, hydroxy group, fluorine atom or isopropoxy group;
$R^{2''}$ represents advantageously a phenyl group optionally single or double substituted with a trifluoromethyl group or methoxy-carbonyl group; or a pyridyl, pyrimidyl, pyrrolidinyl, oxazolidinyl group optionally single or double substituted with a methyl group or fluorine atom;
$R^{3''}$ represents advantageously hydrogen atom;
$R^{4''}$ represents advantageously hydrogen atom;
In general formula (I")
X represents a hydrogen substituted C atom with "R" configuration;
In general formula (II")
Y represents a hydrogen substituted C atom with "S" configuration.

The subject matter of the invention furthermore relates advantageously to novel enantiomeric derivatives of 8-hydroxyquinoline derivatives, and pharmaceutically acceptable salts and complexes with divalent or polyvalent metals, advantageously iron, copper or zinc complexes thereof, especially advantageously zinc complexes thereof as listed detailed as follows:

7-[(R)-[(4-Methylpyrimidin-2-yl)amino][4-(trifluoromethyl)phenyl]-methyl]quinolin-8-ol),
7-[(S)-[(4-Methylpyrimidin-2-yl)amino][4-(trifluoromethyl)phenyl]-methyl]quinolin-8-ol,
Potassium 7-[(R)-[(4-methylpirimidin-2-yl)amino][4-(trifluoromethyl)-phenyl]methyl]quinolin-8-olate,
Potassium 7-[(S)-[(4-methylpyrimidin-2-yl)amino][4-(trifluoromethyl)-phenyl]methyl]quinolin-8-olate,
Natrium 7-[(R)-[(4-methylpyrimidin-2-yl)amino][4-(trifluoromethyl)phenyl]methyl]quinolin-8-olate,
7-[(R)-[(4-Methylpyrimidin-2-yl)amino][4-(trifluoromethyl)-phenyl]methyl]quinolin-8-ol fumarate,
7-[(S)-[(4-Methylpyrimidin-2-yl)amino][4-(trifluoromethyl)-phenyl]methyl]quinolin-8-ol fumarate,
7-[(R)-[(4-Methylpyrimidin-2-yl)amino][4-(trifluoromethyl)phenyl]-methyl]quinolin-8-ol zinc complex,
7-[(R)-[(6-Methylpyridin-2-yl)amino]4-nitrophenyl)methyl]-quinolin-8-ol,
7-[(S)-[(6-Methylpyridin-2-yl)amino]4-nitrophenyl)methyl]-quinoline-8-ol,
7-[(R)-[(6-Methylpyridin-2-yl)amino]3-hydroxyphenyl)methyl]-quinoline-8-ol,
7-[(S)-[(6-Methylpyridin-2-yl)amino]3-hydroxyphenyl)methyl]-quinoline-8-ol,
7-[(R)-[(6-Methylpyridin-2-yl)amino](4-hydroxy-3-methoxyphenyl)methyl]-quinoline-8-ol,
7-[(S)-[(6-Methylpyridin-2-yl)amino](4-hydroxy-3-methoxyphenyl)methyl]-quinoline-8-ol,
7-[(R)-[(6-Methylpyridin-2-yl)amino](5-bromopyridin-2-yl)methyl]-quinoline-8-ol,
7-[(S)-[(6-Methylpyridin-2-yl)amino](5-bromopyridin-2-yl)methyl]-quinoline-8-ol,
7-[(R)-[(6-Methylpyridin-2-yl)amino]2-hydroxyphenylmethyl]-quinoline-8-ol,
7-[(S)-[(6-Methylpyridin-2-yl)amino]2-hydroxyphenylmethyl]-quinoline-8-ol,
5-Chloro-7-[(R)-[(4-methylpyrimidin-2-yl)amino][4-(trifluoromethyl)phenyl]methyl]quinolin-8-ol,
5-Chloro-7-[(S)-[(4-methylpyrimidin-2-yl)amino][4-(trifluoromethyl)phenyl]methyl]quinoline-8-ol,
5-Chloro-7-[(R)-[(6-methylpyridin-2-yl)amino][4-(trifluoromethyl)phenyl]methyl]quinoline-8-ol,
2-Methyl-7-[(R)-[(4-methylpyrimidin-2-yl)amino][4-(trifluoromethyl)phenyl]methyl]quinoline-8-ol,
2-Methyl-7-[(S)-[(4-methylpyrimidin-2-yl)amino][4-(trifluoromethyl)phenyl]methyl]quinoline-8-ol,
2-[(Dimethylamino)methyl]-7-[(R)-[(4-methylpyrimidin-2-yl)amino][4-(trifluoromethyl)phenyl]methyl]quinoline-8-ol, 2-[(Dimethylamino)methyl]-7-[(S)-[(4-methylpyrimidin-2-yl)amino][4-(trifluoromethyl)phenyl]methyl]quinoline-8-ol,
2-[(Dimethylamino)methyl]-7-[(R)-[(4-methylpyridin-2-yl)amino][4-(trifluoromethyl)phenyl]methyl]quinoline-8-ol,
2-[(Dimethylamino)methyl]-7-[(S)-[(4-methylpyridin-2-yl)amino][4-(trifluoromethyl)phenyl]methyl]quinoline-8-ol,
5-Nitro-7-[(R)-[(4-methylpyrimidin-2-yl)amino][4-(trifluoromethyl)phenyl]methyl]quinoline-8-ol,
5-Nitro-7-[(S)-[(4-methylpyrimidin-2-yl)amino][4-(trifluoromethyl)phenyl]methyl]quinoline-8-ol,
7-[(R)-[(Pyridin-2-yl) [4-(trifluoromethyl)phenylamino] methyl]quinoline-8-ol,
7-[(S)-[(Pyridin-2-yl) [4-(trifluoromethyl)phenylamino] methyl]quinoline-8-ol
2-(Hydroxymethyl)-7-[(R)-[(4-methylpyrimidin-2-yl)amino][4-(trifluoromethyl)phenyl]methyl]quinoline-8-ol,
2-(Hydroxymethyl)-7-[(S)-[(4-methylpyrimidin-2-yl)amino][4-(trifluoromethyl)phenyl]methyl]quinoline-8-ol.

The subject matter of the invention furthermore relates especially advantageously to the novel enantiomeric derivatives of 8-hydroxyquinoline derivatives, and pharmaceutically acceptable salts and complexes with divalent or polyvalent metals, advantageously iron, copper or zinc complexes thereof, especially advantageously zinc complexes thereof as listed detailed as follows:
7-[(R)-[(4-Methylpyrimidin-2-yl)amino][4-(trifluoromethyl)phenyl]methyl]quinoline-8-ol,
7-[(S)-[(4-Methylpyrimidin-2-yl)amino][4-(trifluoromethyl)phenyl]methyl]quinoline-8-ol.

The subject matter of the invention furthermore relates especially advantageously to the pharmaceutically acceptable salts and zinc complex of novel enantiomeric derivatives of 8-hydroxyquinoline derivatives, as listed detailed as follows:
Potassium 7-[(R)-[(4-methylpirimidin-2-yl)amino][4-(trifluoromethyl)-phenyl]methyl]quinoline-8-olate,
Potassium 7-[(S)-[(4-methylpyrimidin-2-yl)amino][4-(trifluoromethyl)-phenyl]methyl]quinoline-8-olate,
Natrium 7-[(R)-[(4-methylpyrimidin-2-yl)amino][4-(trifluoromethyl)phenyl]methyl]quinoline-8-olate,
7-[(R)-[(4-Methylpyrimidin-2-yl)amino][4-(trifluoromethyl)-phenyl]methyl]quinoline-8-ol fumarate,
7-[(S)-[(4-Methylpyrimidin-2-yl)amino][4-(trifluoromethyl)-phenyl]methyl]quinoline-8-ol fumarate,
7-[(R)-[(4-Methylpyrimidin-2-yl)amino][4-(trifluoromethyl)phenyl]-methyl]quinoline-8-ol zinc complex.

The subject matter of the invention furthermore relates to medicinal and/or pharmaceutical compositions comprising novel enantiomeric derivatives of 8-hydroxyquinoline derivatives disclosed by general formulas (I) and (II), advantageously (I') and (II'), advantageously (I'') and (II'')—henceforth General Formulas according to the Invention—and advantageously named specifically as above, and/or pharmaceutically acceptable salts and/or complexes with divalent or polyvalent metals, advantageously iron, copper or zinc complexes thereof, as active agent, which compositions are containing inert, pharmaceutically acceptable, solid or liquid carrier and/or excipient, advantageously starch, gelatinized starch, cellulose, microcrystalline cellulose or cellulose-derivatives, lactose, lactose monohydrate, talcum, mannitol, sodium chloride, sodium carbonate, saccharose, maltose, calcium carbonate, colloidal anhydrous silicon dioxide, stearic acid, magnesium stearate or isomalt.

The subject matter of the invention furthermore relates to medicinal and/or pharmaceutical composition, advantageously solid composition, especially advantageously tablet, inhalation powder or capsule, advantageously semi-solid composition, especially advantageously suppository, or advantageously liquid composition especially advantageously solution for injection.

The subject matter of the invention furthermore relates to process for the preparation of medicinal and/or pharmaceutical compositions comprising novel enantiomeric derivatives of 8-hydroxyquinoline derivatives described by General Formulas according to the Invention and advantageously named specifically as above, and pharmaceutically acceptable salts and/or complexes with divalent or polyvalent metals, advantageously iron, copper or zinc complexes thereof by mixing the enantiomeric derivatives and/or pharmaceutically acceptable salts and/or complexes thereof, according to the invention with pharmaceutically applicable carriers and/or excipients disclosed as above, then by formulating the mixture to a medicinal and/or pharmaceutical composition advantageously to tablet, inhalation powder or capsule, suppository or solution especially advantageously to tablet, using the usual, standard formulation technics.

The subject matter of the invention furthermore relates to novel, stereoselective process for the preparation of novel enantiomeric derivatives of 8-hydroxyquinoline derivatives described by General Formulas according to the Invention and advantageously named specifically as above, and pharmaceutically acceptable salts and/or complexes with divalent or polyvalent metals, advantageously iron, copper or zinc complexes thereof, specifically concerning the enantiomeric derivatives of general formula (I) and (II) by reacting an 8-hydroxyquinoline derivative of general formula III

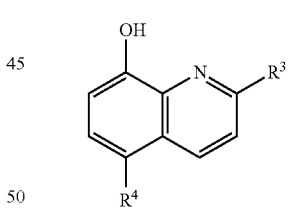

with an amine of general formula (IV),

and with an oxo-compound of general formula (V)

using quinidine (obtaining R-enantiomer) or quinine (obtaining S-enantiomer) as catalyst.

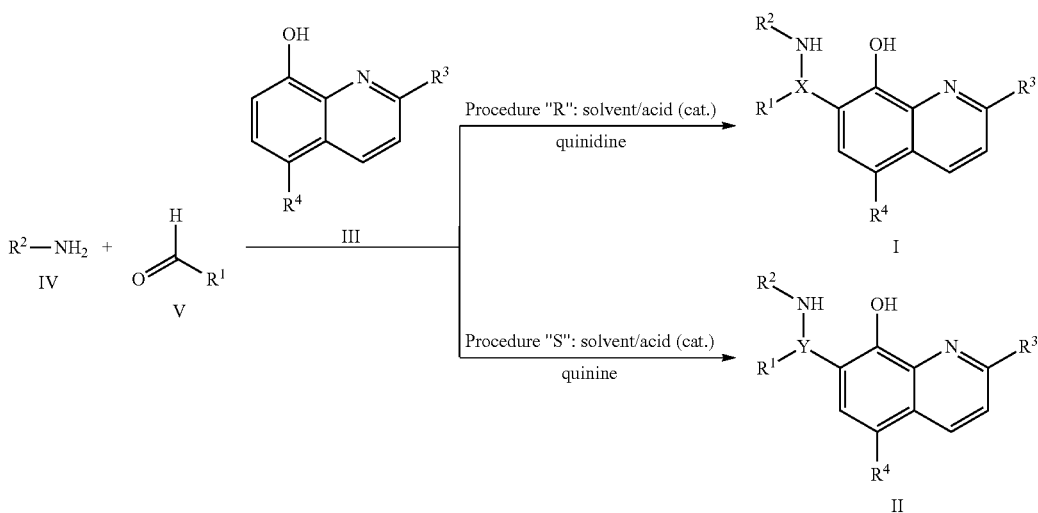

By this method pure R-enantiomeric derivative of general formula (I) or pure S-enantiomeric derivative can be obtained, and can be used as active agent or can be converted to pharmaceutically acceptable salts or to complexes with divalent or polyvalent metals, advantageously iron, copper or zinc complexes specifically advantageously to zinc complexes thereof or can be released from the salt or complex thereof.

The terms quinidine or quinine catalysts are interpreted to have the following chemical structures with the well-known meaning in the art:

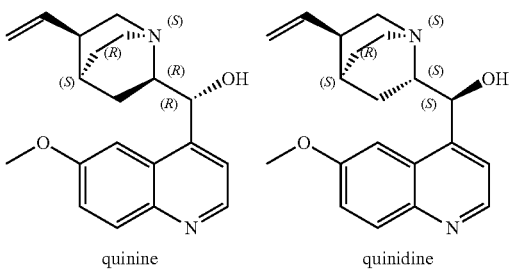

See, for example, X. Liu et al., 7 Organic Letters, 167-169 (2005).

Concerning the further advantageous versions of the compounds of general formulas according to the invention, the process according to the invention is described as above, using the proper R' and R" substituents indexed properly in the general formulas (III'), (III"), (IV') (IV") and (V") and (V"') of the starting materials and reagents according to the different versions of General Formulas according to the Invention and compounds advantageously specifically named as above.

The subject matter of the invention furthermore relates to novel, stereoselective process for the preparation of novel R-enantiomeric derivatives of 8-hydroxyquinoline derivatives of general formulas (I), (I') and (I"), and advantageously named specifically as above, and pharmaceutically acceptable salts and/or complexes with divalent or polyvalent metals, advantageously iron, copper or zinc complexes thereof, specifically concerning the enantiomeric derivatives of general formula (I) and (II) by reacting an 8-hydroxyquinoline derivative of general formula (III), advantageously (III'), further advantageously (III") with an amine of general formulas (IV), advantageously (IV'), further advantageously (IV") and with an oxo-compound of general formulas (V), advantageously (V'), further advantageously (IV"), advantageously using quinidine as catalyst and obtaining by this method pure R-enantiomeric derivative.

The subject matter of the invention furthermore relates to novel, stereoselective process for the preparation of novel S-enantiomeric derivatives of 8-hydroxyquinoline derivatives of general formulas (I), (I') and (I"), and advantageously named specifically as above, and pharmaceutically acceptable salts and/or complexes with divalent or polyvalent metals, advantageously iron, copper or zinc complexes thereof, specifically concerning the enantiomeric derivatives of general formula (I) and (II) by reacting an 8-hydroxyquinoline derivative of general formula (III), advantageously (III'), further advantageously (III") with an amine of general formulas (IV), advantageously (IV'), further advantageously (IV") and with an oxo-compound of general formulas (V), advantageously (V'), further advantageously (IV"), advantageously using quinine as catalyst and obtaining by this method pure S-enantiomeric derivative.

For the process according to the invention solvent, advantageously organic solvent or water, especially advantageously acetonitrile was used as reaction medium. The reaction can be implemented by using advantageously acidic catalyst, especially advantageously formic acid.

For the preparation of the compounds according to the invention the following novel, general stereoselective processes have been applied according to the invention, depending on the starting materials:

For the process according to the invention solvent, advantageously organic solvent or water, especially advantageously acetonitrile was used as reaction medium. The reaction can be implemented by using advantageously acidic catalyst, especially advantageously formic acid.

For the preparation of the compounds according to the invention the following novel, general stereoselective processes have been applied according to the invention, depending on the starting materials:

Process "R" for Preparation of Enantiomers with "R" Configuration:

To a solution of 50 mmol of quinidine in the proper solvent (180 ml), formic acid (0.84 equivalent) was added in inert atmosphere, then amine derivative (1 equivalent), aldehyde compound (1 equivalent) and 8-hydroxyquinoline derivative (1.2 equivalent) were added.

The mixture was stirred at a proper temperature until the product was formed in a desired quantity.

The reaction mixture was concentrated in vacuum to its third volume, the residue was dissolved in dichloromethane. The solution was washed with 1 M NaOH and extracted further by 1M NaOH 6 times.

A non-polar solvent was added to the organic phase then the dichloromethane was evaporated off. The solution obtained was added to 100 ml of 3 M HCl. The phases were separated and the organic layer was extracted with 3 M HCl solution.

To the combined HCl phase methyl-t-butyl-ether was added then the pH of the biphasic system was adjusted with 40% NaOH solution to four.

The precipitated quinidine was filtered off, the biphasic filtrate was separated, then the water layer was washed twice by methyl-t-butyl-ether, the combined organic phase was dried on sodium sulfate and filtered.

A proper solvent was added to the filtrate, the methyl-t-butyl-ether was evaporated off and the residue was stirred at room temperature for 16 hours. The precipitated racemic crystals were filtered.

The mother liquor was concentrated in reduced pressure and the remaining pure R-enantiomer was dissolved in 40 ml of isopropanol, stirred at room temperature for 48 hours, then the precipitated crystals were filtered off, to give pure crystalline R-enantiomer.

Process "S" for Preparation of Enantiomers with S-Configuration

To a solution of quinine (55 mmol) in a proper solvent (300 ml) in inert atmosphere, formic acid (0.8 equivalent), amine (2.5 equivalent), aldehyde derivative (3.7 equivalent), and finally 8-hydroxyquinoline derivative (1.0 equivalent) were added.

The mixture was stirred at a proper temperature until the product was formed in a desired quantity.

The solvent was evaporated off in vacuum, the residue was dissolved in dichloromethane and chromatographed on silica gel. The fractions containing the product were collected and the solvent was evaporated off.

The raw product obtained was purified by normal phase Flash chromatography using hexane-ethyl-acetate gradient, then the fractions containing the product were collected and concentrated.

The residue was dissolved in 2-propanol. After 2 hours stirring the precipitated racemic crystals were filtered off. The mother liquor was concentrated in vacuum to get the S-enantiomer. The raw product was isolated by the usual methods (e.g. filtration, centrifugation) and was purified by known methods if needed (e.g. recrystallization or chromatography).

The subject matter of the invention furthermore relates to the use of novel enantiomeric derivatives of 8-hydroxyquinoline described by General Formulas according to the Invention and advantageously named specifically as above and pharmaceutically acceptable salts and complexes with divalent or polyvalent metals, advantageously iron, copper or zinc complexes thereof, for the manufacture of a medicinal and/or pharmaceutical composition suitable for the treatment and/or prevention of neuropsychiatric diseases advantageously anxiety disorders, schizophrenia, depression, bipolar disorder, especially advantageously bipolar disorder, depression.

The subject matter of the invention furthermore relates to the use of novel enantiomeric derivatives, advantageously the R-enantiomeric derivatives of 8-hydroxyquinoline described by General Formulas according to the Invention and advantageously named specifically as above and pharmaceutically acceptable salts and complexes with divalent or polyvalent metals, advantageously iron, copper or zinc complexes thereof, for the manufacture of a medicinal and/or pharmaceutical composition suitable for the treatment and/or prevention of neurologic diseases, advantageously epilepsy, amnesia, different memory disorders, cognitive functional problems, neurodegenerative diseases especially advantageously memory disorders, epilepsy, amnesia, cognitive functional problems, Alzheimer's disease, Huntington disease, Parkinson disease, Wilson disease, amyotrophic lateral sclerosis (ALS).

The subject matter of the invention furthermore relates to the use of novel enantiomeric derivatives of 8-hydroxyquinoline described by General Formulas according to the Invention and advantageously named specifically as above and pharmaceutically acceptable salts and complexes with divalent or polyvalent metals, advantageously iron, copper or zinc complexes thereof, for the manufacture of a medicinal and/or pharmaceutical composition suitable for the treatment and/or prevention of ischemia and reperfusion injuries thereof, advantageously of cardiovascular disorders, blood vessel catastrophes, traumatic injuries, neurodegenerative traumas, diseases in connection with transplantations and in connection with ischemia and reperfusion injuries thereof, advantageously of impairments of the brain, heart, liver, kidney or lung especially advantageously of traumatic brain injuries and for inhibition of organ, advantageously of skin graft rejection, especially advantageously for inhibition of skin graft rejection.

The subject matter of the invention furthermore relates to the use of novel enantiomeric derivatives of 8-hydroxyquinoline described by General Formulas according to the Invention and advantageously named specifically as above and pharmaceutically acceptable salts and complexes with divalent or polyvalent metals, advantageously iron, copper or zinc complexes thereof, for the manufacture of metal chelate forming, cyto-protective, neuroprotective and/or cardio-protective medicinal and/or pharmaceutical composition, showing favourable binding to the target protein, suitable for the treatment and/or prevention of neuropsychiatric, neurologic diseases and of diseases in connection with ischemia.

The subject matter of the invention furthermore relates to the use of novel enantiomeric derivatives of 8-hydroxyquinoline described by General Formulas according to the Invention and advantageously named specifically as above and pharmaceutically acceptable salts and complexes with divalent or polyvalent metals, advantageously iron, copper or zinc complexes thereof, for the manufacture of a cyto-protective, neuroprotective and/or cardio-protective medicinal and/or pharmaceutical composition suitable for protecting the cells from the cytotoxic attacks, and for the treatment of patients suffering in diseases combined with "cell-death" and/or prevention of their diseases.

The subject matter of the invention furthermore relates to the use of medicinal and/or pharmaceutical compositions comprising novel enantiomeric derivatives of 8-hydroxyquinoline described by General Formulas according to the Invention and advantageously named specifically as above and pharmaceutically acceptable salts and complexes with divalent or polyvalent metals, advantageously iron, copper or zinc complexes thereof for treatment and prevention of the above described diseases, which compositions can be administered by a usual method in medicine, advantageously by oral, buccal, sublingual, parenteral or intravenous, rectal or inhalation method especially advantageously administered by oral method.

The subject matter of the invention furthermore relates to a cytoprotective, neuroprotective or cardioprotective process for treatment and/or prevention of cardiovascular diseases, blood vessel catastrophes, traumatic injuries, neurodegenerative traumas, diseases in connection with transplantations and in connection with ischemia and reperfusion injuries thereof, advantageously of impairments of the brain, heart, liver, kidney or lung especially advantageously of traumatic brain injuries and for inhibition of organ, advantageously for skin graft rejection, especially advantageously for inhibition of skin graft rejection, by administering a medicinal and/or pharmaceutical composition by a usual method in medicine, advantageously by oral, buccal, sublingual, parenteral or intravenous, rectal or inhalation method especially advantageously administered by oral method, which composition comprises novel enantiomeric derivatives of 8-hydroxyquinoline described by General Formulas according to the Invention and advantageously named specifically as above and pharmaceutically acceptable salts and complexes with divalent or polyvalent metals, advantageously iron, copper or zinc complexes thereof.

The subject matter of the invention furthermore relates to a cytoprotective, neuroprotective process for treatment and/or prevention of neuropsychiatric diseases advantageously anxiety disorders, schizophrenia, depression, bipolar disorder, especially advantageously bipolar disorder, and depression and further of neurologic diseases, advantageously epilepsy, amnesia, different memory disorders, cognitive functional problems, neurodegenerative diseases especially advantageously memory disorders, epilepsy, amnesia, cognitive functional problems, Alzheimer's disease, Huntington disease, Parkinson disease, Wilson disease, amyotrophic lateral sclerosis (ALS) by administering a medicinal and/or pharmaceutical composition by a usual method in medicine, advantageously by oral, buccal, sublingual, parenteral or intravenous, rectal or inhalation method especially advantageously administered by oral method, which composition comprises novel enantiomeric derivatives of 8-hydroxyquinoline described by General Formulas according to the Invention and advantageously named specifically as above and pharmaceutically acceptable salts and complexes with divalent or polyvalent metals, advantageously iron, copper or zinc complexes thereof.

II. History, the State of the Art, Mechanism of Action

1) The specification of the history, state of the art, mechanism of action of the novel enantiomeric derivatives of 8-hydroxyquinoline according to the invention, described by General Formulas according to the Invention and advantageously named specifically as above and pharmaceutically acceptable salts and metal complexes thereof and medicines suitable for treatment and/or prevention of different diseases and comprising the subject compounds.

The prior art and patents referred and cited in the present specification hereinafter are all part of the state of the art.

The various etiological cell injuries and cell deaths are the main characteristics of many cardiovascular, neurological and inflammatory disorders. Cell injuries may occur as the results of cellular hypoxia or ischemia, formation of various kinds of oxidants or free radicals and/or overproduction of various biological mediators (cytokines, chemokines, lipid mediators) and overproduction and/or aggregation of different toxic peptides (e.g. β-amyloid peptides) or of proteins (synuclein, huntigtin, prion) in case of neurodegenerative diseases (comprehensive literature: Orrenius, 2007; Mattson, 2006).

These processes are often interdependent; so those occur as parts of self-amplifying ("suicidal") intracellular cycles and form the determining basis of many human diseases.

Though cell death is typically referred as apoptosis or necrosis, these two forms only represent the two ends of the range of the forms of cell injuries.

The intercellular mechanisms taking part in the above cell death processes are complex, but often activate the cell death effector family called caspases and mitochondrial dysfunction, mitochondrial depolarisation, generation of reactive oxygen species and release of mitochondrial components into the cytosol (comprehensive literature: Szabó, 2005; Duprez et al., 2009; Degterev and Yuan, 2008; Wang et al., 2009; Stefanis, 2005).

In the case of Alzheimer's disease, neuronal cell death results mainly from the direct cytotoxic effects of aggregated β-amyloid peptides which, in part are generated by caspase-triggered apoptosis.

The other reason of the deterioration of the cognitive functions is the quantitative decreasing of different synaptic proteins playing role in neurotransmission and the reduced reactivity of different receptors like acetylcholine and muscarine (Machova et al., 2008; Bartus, 2000).

There are more and more evidences, that in the course of β-amyloid peptide aggregation not the fibrillary but the oligomer form has a correlation with neuropathological changes in connection with mortality and dementia, like development of protein tangles and neuritic disorders (e.g. reduced dentrit-spike and reduced numbers of active synapses) (comprehensive literature: Lue et al., 1999; McLean et al., 1999; Wang et al., 1999).

However besides the oligomer forms of β-amyloid peptide aggregates the fibrillary forms results also neuronal destruction and reduced functionality partly through LDI receptors (Janciauskiene et al., 1999).

The compounds preventing cell injury and cell death are usually called "cytoprotective" compounds. Cytoprotection may be achieved by many pharmacological and biochemical methods. The following examples of them are mentioned here: scavengers of oxidants and free radicals, inhibitors of certain "death effector pathways", stabilisation of cell membranes, etc. In the course of ischemia or several related disease processes, iron and copper cations are released from the tissues which catalyse hydroxy-free radical formation in the Haber-Weiss pathway in a known manner causing cell injuries. Inactivation or chelate formation of these metal cations may result in a cytoprotective effect. Thus experiments were conducted to mitigate the catalytic efficiency of iron and copper cations in such a way that iron-chelate forming siderophores (e.g. deferoxamine) were administered (Lewen et al., 2000; Britton et al., 2002).

It is known that glutamate is released along with zinc cations from the synaptosomes of the nervous system cells using glutamate as a chemical messenger. Usually, the zinc released in the nerve synapse is quickly built again in the synaptosomes. As a result of ischemia, lasting attacks and cerebral lesion, the zinc released from the synaptosomes is accumulated in the extracellular liquid surrounding the neurons. When an excessive amount of zinc enters the cell body, zinc may trigger cell death via apoptosis and necrosis.

Zinc-chelate forming through that mechanism may result in neuroprotection and influence the outcome of various neuropsychiatric diseases. (Regland et al., 2001; Koh et al., 1996).

Therefore the zinc-chelating agents may also be useful in treatment of the Alzhemier's disease by binding zinc occurring in the plaques thus weakening the structure of the plaques (Frederickson et al., 2005; Schäfer et al., 2007). The zinc-chelating agents may also be useful in the treatment of Huntington's disease (Nguyen et al., 2005).

According to another way of cytoprotection, the intracellular pathways mediating protective effects are induced. A prototype of this approach is the so-called "ischemic preconditioning" where the cells or organs are subjected to ischemia for a short time in order to induce over-regulation of the cytoprotective genes (e.g. genes of antioxidant enzymes, heat shock proteins and others). Induction of heme oxygenase enzyme (HMOX-1) has demonstrated cytoprotection in several experimental systems (e.g. Li et al., 2007; Idris et al., 2008).

Compounds used for inhibition of endoplasmatic reticulum stress have been described in the American patent application publication no. US 2008/293699.

Part of the state of the art is our own earlier patent application also, where recently new racemic 8-hydroxquinoline derivatives and indications thereof have been described and where some members of this compound family have been identified by cell-based screening tests for systematic identification of cytoprotective compounds (WO2011148208).

In this test a certain form of cell injury was simulated and a chemical library was screened in order to identify compounds preventing or retarding cell injury (e.g. Gero et al., 2007).

By means of the cell-based screening method, we have found and identified novel racemic 8-hydroxyquinoline derivatives. These compounds protect the cells from injuries induced by oxidative stress therefore these can potentially be used in the treatment of many diseases.

The racemic compounds exert various cellular effects e.g. iron-copper and zinc chelating, inhibition of PARP-activation, inhibition of mitochondrial dysfunction, or activation of heme oxygenase enzyme.

However according to our earlier invention only the racemic compounds have been described, the enantiomerically pure derivatives thereof have not been prepared at all, and neither the chemical characters thereof have been disclosed.

Moreover concerning the earlier cytoprotection tests, no direct evidence has been provided, that neuronal destruction triggered by the different aggregated forms of β-amyloid peptides (oligomer, and high molecular weight fibrillary complexes) can be prevented by the racemic compounds and whether they can be used for increasing cognitive functions.

Earlier it was also not known, through which molecular mechanisms the positive effects of each enantiomer can be achieved on neurons, cardiac sells and in neurodegenerative animal models induced by beta oligomers.

It was shown that, the pure R-enantiomeric derivative has effect on several targets that can be related to the neuroprotective effect and inhibiting effect concerning neuroinflammation of the clinical candidate.

The R-enantiomer compound of the Example 2 according to the invention inhibits in micromolar concentration the caspase-3 and 5-lipoxygenase enzymes and the transcriptional induction regulated by the activated T-cell nuclear factor (NF-AT). The activation of caspase-3 is strongly related to several degenerative processes of the aging brain (Lynch et al., 2002) and to the pathogenesis of neurodegenerative diseases occurred in old age (Eckert et al., 2003).

The activation of caspase-3 is a common connection point of many toxic stimulations, included the oxidative injury and the toxicosis induced by the aggregated β-amyloid peptides. The activated caspase-3 protease induces degradation of several key intracellular proteins, resulting apoptosis at the end (Hengartner, 2000).

However the caspase-3 plays important role not only in the late phase of neurodegeneration inducing neuronal destruction but also encourages the development of the pathological changes in the early stage, because it is responsible also for the proteolytic cleavage of both of amyloid precursor protein (APP) and the GGA3 adaptor which are transforming to toxic amyloid peptide aggregates at the end.

The axonal microtubule-associated tau protein forming neurofibrillary tangles is also substrate of the caspase-3 enzyme, so increased function of the caspase-3 enzyme reduces the binding of the tau with total length to microtubule, leading to a neuritic degeneration at the end.

Moreover it has been shown that the fibrillary tau protein deposits in neurons are not causes but consequences of the degenerative processes within the cell induced by the activation of caspase (Calignon et al., 2010).

Coming from all these, the neuronal destruction related to the neurodegenerative processes for different reasons (oxidative stress, effects of β-amyloid peptide aggregates) and the developed deterioration of the cognitive processes can be inhibited inter alia by using the pure R-enantiomeric derivative according to the invention and to the Example 2 for inhibition the caspase enzyme in the brain.

Disturbance in calcium ion homeostasis and the following activation of calcineurin can induce pathological changes related to the Alzheimer's disease (Liu et al., 2005.

The activated T-cell nuclear factor (NFAT) is dephosphorylated by calcineurin, translocated in the cell nucleus by dephosphorylation, triggering expressions of several genes which are inducing neuronal destruction, activation of astrocyte and neuroinflammatory processes. Among these the induction of interleukin-1β (IL-1β) is of primary importance, being one of the causes of the increased level of extracellular glutamic acid, and are involved in hyperexcitable synaptic activity, generally in induction and maintenance of neuroinflammatory processes related to several neurodegenerative diseases (Sama et al., 2008).

Recently it was shown that, the neurotoxicity triggered by β-amyloid could be reduced by pharmacological inhibition of NFAT in transgenic mouse (Hudry et al., 2012).

Furthermore different levels of each NAFT isoforms have been stated in brain samples of patients of Alzheimer's disease suffering from dementia with different severity (Abdul et al., 2009).

It was published by the same authors also, that the protein level of excitatory amino acid transporter (EAAT-2) was NFAT depending reduced by β-amyloid oligomers in astrocytes and the level of glutamic acid resulting neuronal destruction was increased.

Using general NFAT inhibitors all these effects could be reversed proving that NFAT transcriptional activation has important role in pathological processes related to the central nervous system and with the inhibition thereof it was proved that the NFAT system could be an important target concerning the therapy of neurodegenerative diseases.

It is well known that the inhibition of calcineurin/NFAT system reduces the organ graft rejection, so the compounds according to the invention could also be suitable for inhibition of organ graft rejection.

It is well known that the inhibition of calcineurin/NFAT system reduces the organ graft rejection, so the compounds according to the invention could also be suitable for inhibition of organ graft rejection. (Lee és Park, 2006):Lee M, Park J. *Regulation of NFAT activation: a potential therapeutic target for immunosuppression. Mol Cells.* 2006 Aug. 31; 22(1):1-7.).

NFAT transcriptional induction triggered by A23187 ionophore and PMA inductive agent was inhibited by the compound according to the Example 2 and the invention in micromolar concentration. Therefore it can be concluded that the enantiomerically pure R-enantiomeric derivative according to Example 2 is able to inhibit the increased calcineurin activity induced by β-amyloid and by the increased level of intracellular calcium and the consequent calcineurin activity, and therefore it is able to inhibit the apoptotic and neuroinflammatory processes, and positive effect may have generated in different neurodegenerative diseases and by transplantations.

The calcineurin/NFAT system and the caspase-3 apoptotic activation system are related to each other.

The calcineurin over function induces caspase-3 activation and apoptosis (Asai et al., 1999).

As the compound according to Example 2 inhibits both NFAT transcriptional activity and caspase-3 enzyme activity the compound according to the invention reduces the neuronal destruction by double effects, but also has positive effect on the neuroinflammatory processes induced by NFAT.

Therefore it is assumed that pure R-enantiomeric derivative has more efficiency than the solely on NAFT system active or solely the caspase-3 enzyme inhibiting compounds.

The third target of the pure R-enantiomeric derivative according to the invention and to Example 2 is the enzyme 5-lipoxygenase (5-LOX) having an important role in inflammatory and traumatic (excitotoxic and ischemic) processes related to central nervous system (Zhou et al., 2006) and in neurodegenerative diseases related to aging (Uz et al., 1998).

It was shown in transgenic mice that inhibition of 5-LOX reduced β-amyloid aggregates and improved the cognitive functions (Firuzi et al., 2008).

Increased activity of 5-LOX reduced the level of PSD-95, synaptophysin and MAP2 proteins being important in synaptic integrity (Chu et al., 2013).

It is concluded from all these that, the R-enantiomeric derivative according to the Example 2 having micromole activity validly, reduces the neuroinflammatory processes by inhibition of 5-LOX enzyme thereof and has positive influence on pathological changes related to β-amyloid peptides and tau proteins The cell injury caused by hypoxia is a common characteristic of different diseases including brain infarct, brain stroke and infarct of heart muscle.

An important and central element of cell's accommodation to hypoxia is the hypoxia-inducible factor (HIF), a transcription factor activating expressions of several genes inter alia including the genes playing important role in glucose metabolism, in the antioxidant system, in angiogenesis or in blood cell formation (comprehensive article: Chowdhury et al., 2008).

It was shown that, impacts causing rise of the level of HIF, have advantageous effect on ischemic diseases and on reproduction of stem cells (Zhang et al., 2006).

Using a screening system described earlier, HIF system activating small molecules, including several 8-hydroxyguinoline type compounds with furcate structure could be identified (Smirnova et al., 2010). However among the molecules listed in the examples there was not any pure enantiomer, only racemic mixtures have been worked with.

The subject racemic compounds activated the expression of genes with a value between 2-10 µM $IC_{50}$ by 2-7× maximal value. According to our invention, it has been found that, the R-enantiomeric derivatives according to Example 2 and S-enantiomeric derivatives according to Example 3 were capable to increase the gene activity of phosphoglycerate kinase 1 (PGK-1), the vascular endothelial growth factor (VEGF), the hemoxygenase 1 (HMOX-1) and the erythropoietin (EPO) in the cells, all regulated by HIF.

According to our invention the highest activation was found in case of EPO gene, in submicromolar concentration with over 20× maximal activation value.

The PGK1, VEGF, EPO activations have been disclosed in the subject document (Smirnova et al., 2010), but it was not shown any activity of 8-hydroxyquinoline type compounds Furthermore recently it has been shown that, the hemoxygenase 1 (HMOX-1), an antioxidant enzyme induced by HIF has strong cytoprotective effect in neurons (Chen et al., 2000) and in endothelial cells of brain capillaries (Bresgen et al., 2003).

As oxidative stress plays an important role in several neurodegenerative and neuroinflammatory processes, the pharmacological induction of HMOX-1 is judged as a logic and desirable therapeutic solution (Calabrese et al., 2003; Jazwa and Cuadrado., 2010).

The induction of HMOX-1 influenced also the outcome of heart transplantation advantageously (Bach 2006).

In one of our earlier publication it has been shown that, a racemic 8-hydroxyquinoline causes increase of HMOX-1 gene activity in cardiac sells, explaining partly the cardioprotective characteristics thereof in cell system and protective effect
thereof in case of heart muscle injury caused by ischemia/reperfusion in rat (Korkmaz et al., 2013).

On the other hand none of the enantiomerically pure form of the compound group described in the present patent application of general formula has been examined yet.

It was shown that, the R-enantiomeric derivative according to Example 2 and S-enantiomeric derivative according to Example 3 caused the induction of HMOX-1 in astrocytes, concluding that, both pure enantiomer described by us can have cytoprotective effect concerning the diseases with oxidative stress.

The highest inductive effect of R-enantiomeric derivative according to Example 2 and S-enantiomeric derivative according to Example 3 on expression of gene was stated in case of EPO gene.

Moreover it has been shown that, by oral administration, the R-enantiomeric derivative according to Example 2 resulted increased EPO gene activity in cerebral cortex and hippocampus of elderly mice chronically.

Recently it was shown that, the EPO in brain has outstanding role in neuroprotection and advantageous characteristics thereof revealed itself in several psychiatric diseases like depression, schizophrenia, bipolar disorder, epilepsy (Newton et al., 2013) in neurodegenerative diseases like Alzheimer's disease, Parkinson disease (Arabpoor et al., 2012; Xue et al., 2007), traumatic brain injury, blood vessel catastrophes in brain (Mammis et al., 2009), diseases characterized by neuroinflammation, like sclerosis multiplex (Hagemeyer et al., 2012), and had positive effect in animal models and several clinical tests concerning other diseases related to central nervous system, like amyotrophic lateral sclerosis (ALS) (Noh at al., 2014; Merelli et al., 2013; Chong et al., 2013). Because of this there were several methods examined targeting the ingestion of the EPO directly into the brain.

The intravenous EPO injection could cause system side effects, therefore there were experiments also for ingesting EPO through the nose (Merelli et al., 2011).

However these kind of applications could have several disadvantages inter alia the costly production, the involved administration, stability, dosage and the side effect on possible blood cell forming organs of EPO.

Therefore according to an advantageous solution an EPO synthesis could be induced locally in the brain by a small molecule.

This goal has been achieved by the enantiomeric derivatives according to the invention, described in the present patent application and concrete examples has been given concerning the EPO inducing effect of R-enantiomeric derivative according to Example 2 and S-derivative according to Example 3 in cell system.

Concerning the R-enantiomeric derivative according to the Example 2 and the invention it was shown that, it can increase the EPO gene activity in different regions of brain also in living animal.

By these characteristics of the compounds according to the invention and disclosed in the present patent application it is obvious to use them in case of different psychiatric diseases, diseases related to ischemia and central nervous system, neurodegenerative disorders, and inflammatory processes related to the brain.

2) History of the Process According to the Invention

The process is actually a modification according to the invention of the known Betti-reaction, which makes possible to prepare novel enantiomeric derivatives by novel, stereoselective synthesis.

In the course of the stereoselective process according to our invention the R- or S-enantiomeric derivatives have been prepared by using cinchona stereoisomer (quinidine or quinine) in a novel enantioselective version of Betti reaction (Betti, 1900; Betti, 1903; Phillips et al., 1954; Phillips et al., 1956; Phillips, 1956) modified and optimised by us.

The advantage of our process is that the proper enantiomers were obtained by a simple recrystallization over 99% enantiomeric excess, without using any separation technique (e.g. chiral preparative HPLC) using low-cost cinchona organocatalysts: catalysed by quinidine R-enantiomer, catalysed by quinine S-enantiomer could be obtained.

The known processes disclosed in the background literature of stereoselective Betti-reaction mainly enantiomerically pure reactant (e.g. aralkyl amine) was used, then the proper enantiomers were isolated by separation of the chiral support (Palmieri, 2000).

Organocatalysed asymmetric reactions using cinchona alkaloids or modified derivatives thereof are known in case of Mannich reactions (Verkade at al., 2008).

III. Summary

The essence and advantages of the invention can be summarised as follows.

The enantiomerically pure R-enantiomeric derivative prevents the destruction of neurons, the neuroinflammatory processes induced by astrocytes and microglia and furthermore advantageously reduces the pathological reactions related to amyloid peptides and to tau proteins which are destroying the neurotoxic and synaptic systems, In consequence the compounds according to the invention advantageously to Example 2 reduces the deterioration of the cognitive functions related to neurodegenerative processes and therefore they could be therapeutically effective in treatment of several degenerative diseases related to the central nervous system.

As the of enantiomerically pure compounds according to the invention advantageously to Example 2 influence all the three identified targets (caspase-3, NAFT, 5-LOX), effectively, they are effective not only in neurodegenerative processes, but also in different ischemic processes like ischemic and inflammatory processes related to heart vascular system, therefore the compound could be also effective in treatment of diseases related to these processes.

The active ingredient of the medicinal and/or pharmaceutical compositions according to our invention is a molecule on one side not complexed with iron, copper or zinc cations, on the other side forms complex with iron, copper or zinc cations. The essence of the subject matter of the invention and base of novelty is that all prior art documents and patents being part of the state of the art disclosed only the racemic products and characteristics, biological effect thereof, the pure enantiomers according to the invention and characteristics, biological effect thereof are disclosed in our present patent application for the first time.

The essence of our invention is furthermore that the novel enantiomers according to the subject matter of invention are prepared by the stereoselective synthesis also according to the subject matter of the invention therefore the novel pharmaceutical compositions are well applicable for prevention and/or treatment of the diseases listed in present specification, which applications are also part of the subject matter of the invention.

The essence of the stereoselective process according to the invention is that using quinidine catalyst enantiomerically pure R-enantiomer, using quinine catalyst enantiomerically pure S-enantiomer is formed.

The medicinal and/or pharmaceutical compositions according to our invention can be used for prevention and/or treatment of the diseases listed in present specification as cytoprotective, neuroprotective and cardioprotective agent.

So the subject matter of our invention furthermore relates to a cytoprotective, neuroprotective and cardioprotective process for prevention and/or treatment of the diseases listed in present specification by administering the medicinal and/or pharmaceutical compositions according to the invention by a usual method in medicine, advantageously administered by oral method.

IV. Statement of the Figures

The patent or application file contains at least one drawing executed in color. Copies of this patent or patent application publication with color drawing(s) will be provided by the U.S. Patent and Trademark Office upon request and payment of the necessary fee.

FIG. 1

The calculated configuration of the conformer of the S-enantiomer compound according to the invention (1) with the lowest energy.

FIG. 2

The FTIR (Fourier transform infrared spectroscopy) and VCD (Vibrational Circular Dichroism) spectrum of the sample of R-enantiomer compound according to the invention measured in $CDCl_3$ (deuterated chloroform) solvent.

FIG. 3

The calculated VCD spectrum of the conformers of the S-enantiomer compound according to the invention with greater population than 1%.

FIG. 4.

The theoretical VCD spectrum of S- and R-enantiomer compounds according to the invention and the conformers thereof measured in $CDCl_3$ calculated as with the population weighted sum.

FIG. 5

The inhibiting effect of the R- and S-enantiomer compounds according to the invention on different matrix metalloprotease enzymes is shown.

FIGS. 6A and 6B

The effect of R-enantiomer compound according to the invention on cell death in vitro caused by hydrogen-peroxide on cardiac sells is shown.

FIGS. 7A and 7B

The effect of R-enantiomer compound according to the invention on cell death in vitro caused by hydrogen-peroxide on SH5Y neuron cells is shown.

FIGS. 8A and 8B

The effect of S-enantiomer compound according to the invention on cell death in vitro caused by hydrogen-peroxide on cardiac sells is shown.

FIGS. 9A and 9B

The effect of S-enantiomer compound according to the invention on cell death in vitro caused by hydrogen-peroxide on SH5Y neuron cells is shown.

FIG. 10

The effect of sodium salt of R-enantiomer compound according to the invention on cell death in vitro caused by fibrillar aggregates of β-amyloid peptides on primer cortical neuron cells is shown.

FIG. 11

The effect of zinc complex of R-enantiomer compound according to the invention on cell death in vitro caused by fibrillar aggregates of β-amyloid peptides on primer cortical neuron cells is shown.

FIG. 12

The effect of R-enantiomer and S-enantiomer compounds according to the invention and according to Example 2 and 3 on short-term memory disorders in vivo caused by oligomer aggregate of β-amyloid peptides is shown.

FIG. 13

The effect of different concentration of R-enantiomer compound according to the invention and according to Example 2 on short-term memory disorders in vivo caused by oligomer aggregate of β-amyloid peptides is shown.

FIG. 14

The effect of R-enantiomer and S-enantiomer compounds according to the invention and according to Example 2 and 3 on short-term memory disorders in vivo caused by scopolamine is shown.

FIG. 15

The diagram of inhibition effect of R-enantiomeric derivative according to the invention and according to Example 2 on NFAT protein transcriptional activity

FIG. 16

The effect of R-enantiomeric derivative according to the invention and according to Example 2 influencing the gene expression in primer astrocytes

FIG. 17

The effect of R-enantiomeric derivative according to the invention and according to Example 2 influencing erythropoietin gene expression in hippocampus and cerebral cortex of elderly animals in course of chronical treatment.

FIG. 18

The effect of R-enantiomeric derivative according to the invention and according to Example 2 influencing the survival of the skin graft in course of chronical treatment after skin grafting.

V. Explanation of Expressions, Abbreviations Used in the Specification

Expression "enantiomerically pure":

Characteristic property of a certain enantiomeric form containing the other enantiomeric form to a specified percentage: so e.g. in case of 100% purity there is no other enantiomeric form at all, in case of 98% purity the other enantiomeric form is in 2% present etc.

Expression "lower alkyl group":

Straight or branched chained alky groups with 1-4 carbon atoms like e.g. methyl, ethyl, isopropyl groups etc.

Expression "cyclo alkyl group"

Cyclic groups comprising 3-8 carbon atoms like cyclopropyl, cyclobutyl, cyclohexyl group etc.

Expression "aryl group":

Monocyclic or bicyclic aromatic hydrocarbon groups like e.g. phenyl group, naphthyl group Expression "aralkyl group":

Alkyl group described above, substituted by one or two aryl groups described above, like e.g. benzyl, beta phenylethyl group etc.

Expression "heteroaryl group":

5 or 6 membered aryl groups containing one or more oxygen, nitrogen and/or sulfur atoms like pyridyl, pyrimidyl, pyrroryl, oxazolyl groups etc.

Expression "halogen atom":

Fluorine, chlorine, bromine or iodine atoms

Expression "Electron withdrawing substitutes":

The indicator of electron withdrawing groups, represented as substituents, advantageously halogen atoms, nitro groups, trifluoromethyl, methysulfinyl or methylsulfonyl groups.

Expression "Electron donating group":

The indicator of electron donating groups represented as substituents advantageously lower alkyl groups with 1-4 carbon atoms like e.g. methyl group.

Expression "General Formulas according to the invention"

The common meaning of the general formulas (I) and (II), advantageously (I') and (II'), especially advantageously (I" and II"), where the general formulas signed by comma are meaning the advantageous properly substituted versions.

Pharmaceutically acceptable salts:

The novel enantiomers of 8-hydroxyquinoline derivatives according to the invention described by the General Formulas according to the Invention as given above and named specifically can form salts with bases on the hydroxy group and with acids on nitrogen atom in the substituent attached to position 7 of the quinoline ring.

For the salt formation pharmaceutically suitable bases advantageously alkaline metal hydroxydes like sodium-hydroxyde potassium-hydroxyde or organic acids advantageously hydrogen bromide, acetic acid, fumaric acid, maleic acid, malic acid, succinic acid, tartaric acid, benzenesulfonic acid, p-toluenesulfonic acid or methane sulfonic acid can be used.

Pharmaceutically acceptable complexes:

The novel enantiomers of 8-hydroxyquinoline derivatives according to the invention described by the General Formulas according to the Invention as given above and named specifically can coordinatively bind divalent or polyvalent metals (like e.g. iron, zinc, copper etc.) and forming complexes with them.

In such complexes the free electron pairs of the oxygen atom of hydroxyl group and of nitrogen atom of the quinolone are participating.

Chelate forming effect:

The novel enantiomers of 8-hydroxyquinoline derivatives according to the invention described by the General Formulas according to the Invention as given above and named specifically are capable to form chelates with the free electron pairs described as above the same way as complexes are formed. Thank to this chelate forming feature the unbeneficial processes caused by metal ions can be inhibited in different diseases, and also the functioning of proteins containing metal ions can be influenced advantageously.

Indications, Explanations of Sets of Diseases

The following statement of sets and collective nouns of indications and diseases gives help to interpret and to understand the specification of the application and the use claims containing the indications.

1) Neuropsychiatric diseases
   anxiety disorders, schizophrenia, depression, bipolar disorder
2) Neurologic diseases:
   epilepsy, amnesia, different memory disorders, cognitive functional problems and neurodegenerative diseases including memory disorders, epilepsy, amnesia, cognitive functional problems, Alzheimer's disease, Huntington disease, Parkinson disease, Wilson disease, amyotrophic lateral sclerosis (ALS).
3) Ischemia and Reperfusion Injuries Thereof in Connection mainly but not solely with cardiovascular disorders, blood vessel catastrophes, traumatic injuries and neurodegenerative traumas, diseases in connection with transplantations: impairments of the brain, including traumatic brain injuries, and impairments of heart, liver, kidney or lung and organ, advantageously skin graft rejections.

VI. Chemical Examples

The subject matter of our invention is supported by the following examples without limiting the scope of protection to the examples.

Example 1

The Determination of the Absolute Configuration

The racemic mixture of molecules according to Example 2 and Example 3 comprises one chiral center, but they have significant conformation freedom so to determine the absolute configuration also detailed analysis of conformation was needed.

The essence of the determination of the absolute conformation based on VCD spectroscopy is the ab initio (DFT) levelled calculation of the VCD spectrum of one or the other enantiomeric form, and then the comparison of the calculated and the measured spectrum thereof. As the VCD spectrum comprises high number of bands with alternating signals the comparison is generally extremely reliable.

In case the position and signal-pattern of the bands of calculated and measured spectrum correspond, the absolute configuration corresponds with the configuration of the chosen enantiomeric form, if mirrored, the configuration is the opposite.

In presence of more conformers the measured spectrum should be compared with the theoretic spectrum obtained as population-weighted average of calculated spectrum of each of enantiomeric compounds.

The FTIR and VCD spectra of the sample were recorded by a Bruker PMA-37 typed VCD-module connected with a Bruker Equinox55 FTIR spectrometer with resolution of 4 $cm^{-1}$, in a $BaF_2$ cuvette with 0.05 mm layer thickness, in $CDCl_3$ solvent, in 100 mg/ml concentration, using MCT detector cooled by liquid $N_2$. The spectrometer was optimized on fingerprint-range therefore an optical filter transparent in 1800-800 $cm^{-1}$ range was used and the photoelastic modulator of the device was set on 1300 $cm^{-1}$ wave number.

The calibration of the device was implemented with the help of a Cds standard double refracted crystal (CdS multiple wave-plate, MPW) and a polarisation filter as analyser with metal grid and with KRS-5 carrier.

In case of the sample and the reference approximately 42000 interferograms were averaged that corresponds to a recording time if 12 hours to optimize the bad signal-to-noise ratio caused by the low signal-intensity of VCD spectra.

To correct the baseline of the VCD spectrum, the solvent spectrum recorded under same condition was extracted from the raw spectrum.

The infrared spectrum can be obtained together with the VCG spectrum from the ratio of one channelled DC spectrum of the sample and that of the reference (solvent) (this is a global infrared signal not containing any chiral information).

The quantum chemical calculations were performed on a Supermicro server (2× Intel Xeon™ X5680 3.3 GHz 6-corn processor, 72 GB RAM) using a Gaussian 09 software package (Frisch et al., 2010.).

The quantum chemical calculations were performed on the S-enantiomeric form on B3LYP/6-31G** DFT theoretical level, under vacuum condition, the mapping of the conformers was performed along the five torsion angle $(\theta_1-\theta_5)$ (FIG. 1) describing the flexibility of the molecule with partly systematic partly heuristic searching.

The calculation of the IR- and VCD-spectra of the structures with optimized geometry was performed also on B3LYP/6-31G** DFT level.

The calculated frequency (wave number) values were corrected by 0.97 scale factor usable in case of B3LYP/6-31G** theoretical level.

For the generation of the theoretical spectra were assumed a signal-shape of Lorentz diagram and half-width measured at 6 $cm^{-1}$ mid-height.

For visualization of the vibrational spectrum GaussView 5.0 program package has been used.

For estimating the population formed on temperature T=298K, Boltzmann-distribution was assumed. According to the Boltzmann distribution the relative population of the ith conformer compared to the conformer having the lowest free enthalpy (i=0) is:

$$\frac{N_i}{N_0} = e^{-\frac{\Delta G_i}{RT}}$$

$$\Delta G_i = G_i - G_0$$

The mole fraction of ith conformer (the population measured to the whole conformer mixture) is:

$$x_i = \frac{N_i}{\sum_i N_i}$$

In that case the calculated IR- or VCD spectrum is the weighted sum of the spectra of each conformers:

$$S(\tilde{v}) = \sum_i x_i S_i(\tilde{v})(IR, VCD)$$

It can be stated after implementation of the population analysis of the 32 calculated conformer results that there are very small energy differences between the individual conformers so no dominant conformer can be determined.

Among of these eleven have higher population than 1%. Summarizing these eleven conformers they take 99.6%, so the spectral contribution of conformers with higher energy was neglected.

The geometrical data, relative free enthalpies and population of the eleven conformers with higher population than 1% are summarized in Table 1.

TABLE 1

The characterising torsion angle data, relative free enthalpy and estimated population of the S-enantiomer at 298 K temperature, on the basis of quantum chemical calculations carried out on B3LYP/6-31G** levelled vacuum status.

| Conformer | $\theta_1$ (°) | $\theta_2$ (°) | $\theta_3$ (°) | $\theta_4$ (°) | $\theta_5$ (°) | ΔG (kJ/mol) | Population (%) |
|---|---|---|---|---|---|---|---|
| 1 | 142.0 | −173.5 | −95.5 | −74.4 | −179.2 | 0.0 | 20.3 |
| 1 | 136.3 | −14.7 | 162.1 | 70.6 | 179.9 | 0.6 | 15.9 |
| 3 | 82.7 | −172.8 | 65.5 | 87.1 | 178.9 | 1.0 | 13.6 |
| 4 | 137.3 | 166.7 | 160.5 | 71.0 | 179.8 | 1.3 | 12.2 |
| 5 | 83.3 | −172.8 | −109.4 | 87.4 | 178.9 | 1.4 | 11.5 |
| 6 | 88.3 | −10.8 | 13.7 | −136.6 | 179.4 | 3.1 | 5.8 |
| 7 | 88.4 | −10.8 | −166.6 | −136.9 | 179.4 | 3.1 | 5.7 |
| 8[a] | 80.9 | 8.2 | 62.2 | 87.0 | 178.7 | 3.3 | 5.4 |
| 9[a] | 81.2 | 8.2 | 119.0 | 87.4 | 178.6 | 3.8 | 4.4 |
| 10 | 143.8 | 6.7 | −93.0 | −73.7 | −179.5 | 4.2 | 3.7 |
| 11 | 89.6 | 169.4 | 12.7 | −136.4 | 179.3 | 7.5 | 1.0 |

[a]Differing only in spacing of $CF_3$ group

It is characteristic for all these conformers that thay have H-bound between the hydrogen atom of the hydroxyl group and the nitrogen of the quinolone ring. In some conformers not mentioned here this is missing, respectively the conformers with H-bound with the N-atom of the aminopyrimidine part are energetically also less favourable. The spatial structure of the conformers with the lowest energy is shown on Scheme 1.

Infrared and VCD Spectra, the Determination of Absolute Configuration

Figure 2:
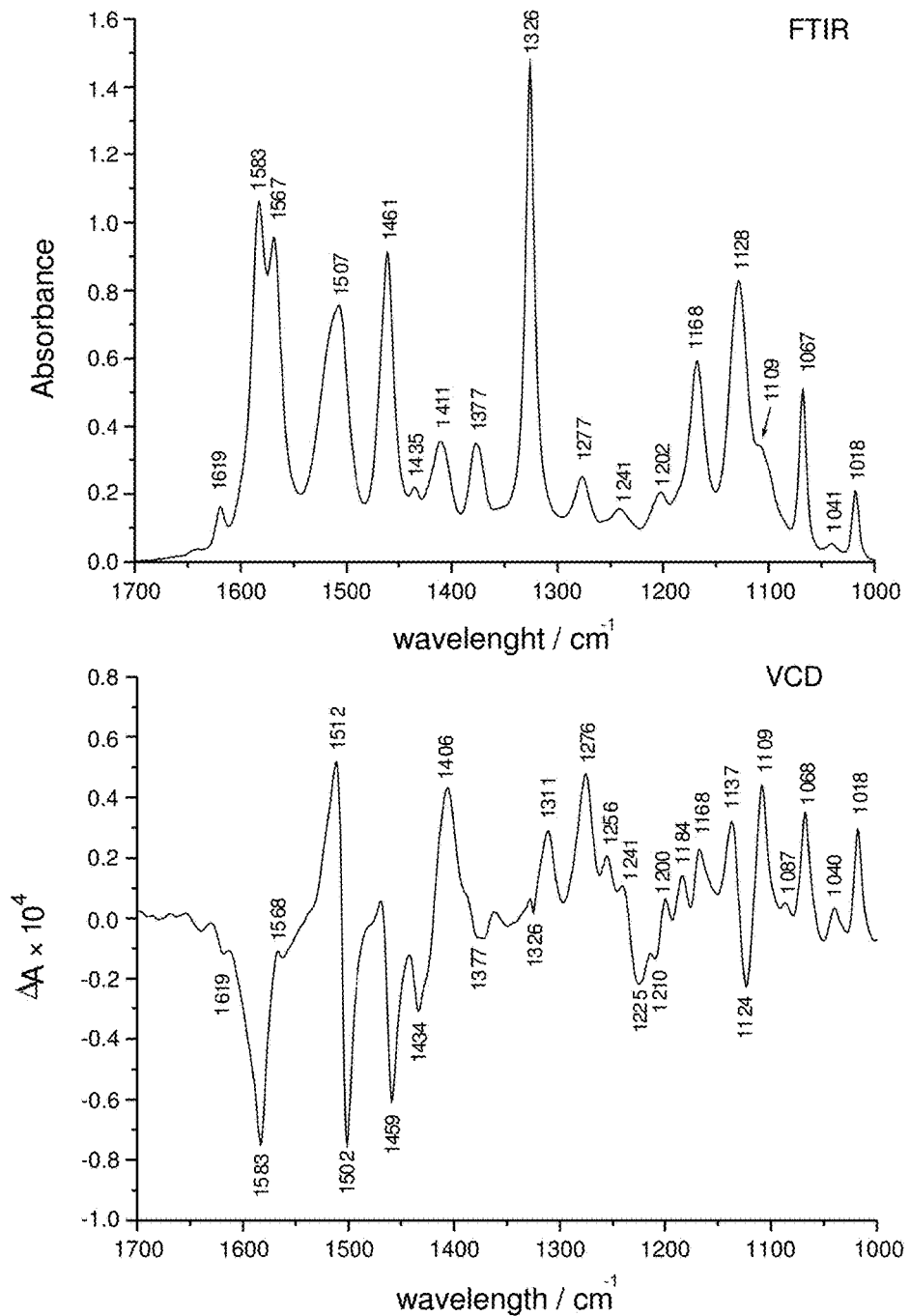

The FTIR and VCD spectrum of compound according to Example 2, is shown in FIG. 2 in the spectral range of 1700-1000 $cm^{-1}$.

This approximately corresponds to the spectral region limited by the characteristics of optics of VCD spectrometer and the transmission of the solvent ($CDCl_3$) used in 0.05 mm cuvette. It can be stated that there are more bands in the VCD spectrum than in the FTIR spectrum referring to the fact that in several cases there is a band overlap in the infrared spectrum so the corresponding bands of VCD spectrum can be identified either only as a "shoulder" or cannot be identified at all.

The extreme values (maximums or minimums) in VCD and in infrared spectrum should appear at identical wavelength in principle; small differences can be explained also by band overlap. It can generally be stated that the vibrations of aromatic and heteroaromatic rings couple strongly with the functional groups attached to them hence their assignation is fairly difficult due to their delocalization.

The most intensive band of the IR spectrum at 1326 $cm^{-1}$ derives from the coupling of the symmetric deformation vibration of $CF_3$ group and the skeletal vibration of benzene ring, but the corresponding VCD band has a very low intensity.

One of the most indicative part of VCD the spectrum is the negative-positive band-pair at 1502 $cm^{-1}$ and 1512 $cm^{-1}$ that are not separated in the IR spectrum but they merge into a broader band at 1507 $cm^{-1}$. According to the calculations the positive band at 1512 $cm^{-1}$ has a special diagnostic value as it derives from coupling of the deformation of the C—H bond attached to the chiral center and the in-plane deformation vibration of C—N—H part of 2-aminopyrimidine group. The negative band at 1507-$cm^{-1}$ derives from the skeletal vibration of quinoline ring and the in-plane OH deformation vibration of its OH substituent, to a certain extent coupled with the deformation of the C—H bond of the chirality center. The intensive band at 1583 $cm^{-1}$ derives from coupling of the skeletal vibration of pyrimidine ring and the in-plane N—H deformation vibration of the seconder amino group attached to it.

Figure 3:
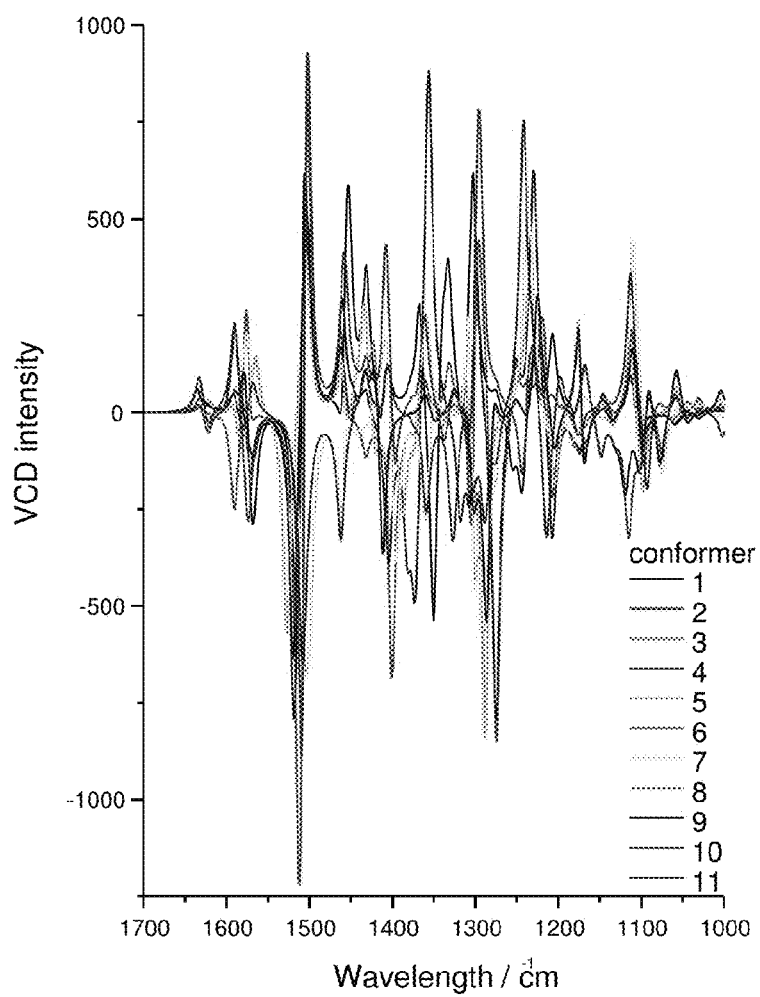
Figure 4:
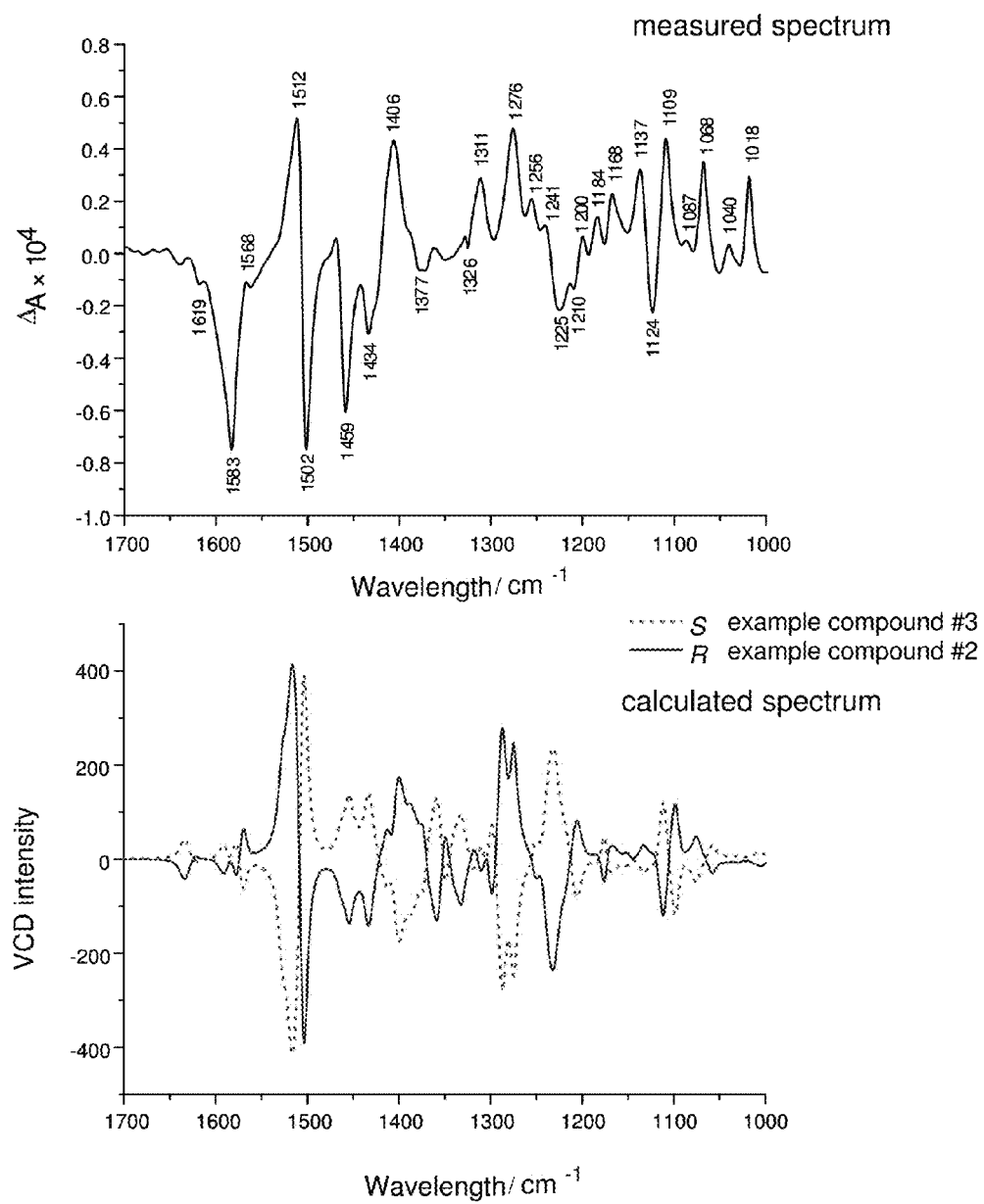

The calculated VCD spectrum of the relevant conformers of the S-enantiomer is shown in FIG. 3. It can be seen from the spectrum that the pattern of the VCD bands depends strongly from the conformers, resulting high averaging and due to coupling of vibrations it is not possible to abstract from the conformation conditions of the achiral aromatic and heterocyclic parts. In the case of the bands at the area of 1500 $cm^{-1}$ mentioned above having high diagnostic value, there is luckily almost no change at least concerning the conformers with higher population. The analysis of all calculated spectra of the conformers (32 pieces) resulted in that the sign of these bands with diagnostic value turns to the opposite only in case of conformers where the N—H bond and the bond of chiral center have the same direction. These conformers are energetically negligible, very unfavourable forms with a population far below 0.1%. It is obvious that for the determination of absolute configuration both the experimental spectrum and the calculated spectrum weighted with population are needed (FIG. 4), but according to FIG. 3 it is also shown that the signs of most of the bands (included also the bands at the area of 1500 $cm^{-1}$) are opposite from the signs of experimental VCD spectrum.

Considering that the VCD spectra of enantiomers are mirrored, based on the wave number and sing-pattern of VCD bands of the measured spectrum and the theoretical, calculated spectrum weighted with the population (FIG. 4) it has been concluded that the compound according to Example 2 is an R-enantiomer (Scheme 2). The measured VCD spectrum is in good agreement with its theoretical spectrum and it has basically opposite spectrum compared to the molecule with S-configuration used in the course of molecular modelling.

Example 2

Preparation of Enantiomerically-Pure 7-[(R)-[(4-Methylpyrimidin-2-yl)amino][4-(trifluoromethyl)phenyl]methyl]quinolin-8-ol In inert atmosphere 180 ml of acetonitrile, 16.22 g (50 mmol, 0.5 eq) of quinidine, 3.87 g (84 mmol, 0.84 eq) of formic acid, 10.91 g (100 mmol, 1.0 eq) of 2-amino-4-methylpyrimidine, 17.41 g (100 mmol, 1.0 eq) of 4-trifluoromethylbenzaldehyde, and finally 17.42 g (120 mmol, 1.2 eq) of 8-hydroxyquinoline were added into a 500 ml round bottom flask. The mixture was stirred for 16 hours at acetonitrile reflux temperature.

The acetonitrile solution was concentrated in reduced pressure to its third volume; the residue was dissolved in 100 ml of dichloromethane. The solution was washed twice with 100 ml of 1M NaOH solution and extracted further six times by 50 ml of 1M NaOH solution. 100 ml of toluene was added to the organic phase then the dichloromethane was evaporated off. The solution obtained was added to 100 ml of 3 M HCl. The phases were separated and the toluene phase was extracted with 30 ml of 3 M HCl solution. To the combined HCl phases methyl-t-butyl-ether was added then the pH of the biphasic system was adjusted with 40% NaOH solution to 4.

The precipitated quinidine was filtered off, the biphasic filtrate was separated, then the water layer was washed twice by 20 ml of methyl-t-butyl-ether, the combined ether phase was dried on sodium sulphate and filtered. 30 ml acetonitrile was added to the filtrate, the methyl-t-butyl-ether was evaporated off and the acetonitrile residue was stirred at room temperature for 16 hours. The precipitated crystals were filtered to get 7.61 g (18.5 mmol, HPLC: 95%) of racemic crystalline product.

The mother liquor was concentrated in reduced pressure to give 14.3 g of crude enantiomerically-pure R-isomer (HPLC: 80%).

The crude R-enantiomer was then dissolved in 40 ml of isopropanol, stirred at room temperature for 48 hours, then the precipitated crystals were filtered off, to give 5.67 g (13.8 mmol, HPLC:98.9%, ee: 99%) of pure crystalline R-enantiomer.

$^1$H-NMR (ppm): 10.1, 1H, s; 8.85, 1H, dd; 8.30, 1H, dd; 8.15, 1H, d; 8.07, 1H, d; 7.75, 1H, d; 7.65, 2H, d; 7.60, 2H, d; 7.53, 1H, dd; 7.41, 1H, d; 7.09, 1H, d; 6.51, 1H, d; 2.25, 3H, s Example 3

Preparation of Enantiomerically-Pure 7-[(S)-[(4-Methylpyrimidin-2-yl)amino][4-(trifluoromethyl)phenyl]methyl]quinolin-8-ol In inert atmosphere 300 ml of acetonitrile, 18 g (55 mmol, 0.5 eq) of quinine, 3.05 g (66 mmol, 0.80 eq) of formic acid, 22.00 g (200 mmol, 2.5 eq) of 2-amino-4-methylpyrimidine, 51.00 g (290 mmol, 3.7 eq) of 4-trifluoromethylbenzaldehyde, and finally 11.5 g (79 mmol, 1.0 eq) of 8-hydroxyquinoline were added in a 1 l, four necked round bottom flask.

The mixture was stirred at 73° C. for six days.

The solvent was evaporated off in reduced pressure. The residue (93.4 g) was dissolved in 200 ml of dichloromethane and chromatographed on 100 g silica gel.

The fractions containing the product were collected and the solvent was evaporated off (60.4 g). The raw product obtained was purified by normal phase Flash chromatography using hexane-ethyl-acetate gradient, then the fractions containing the product were collected and concentrated (19.81 g).

The residue was dissolved in 190 ml of 2-propanol. After 2 hours stirring the precipitated racemic crystals were filtered off. The mother liquor was concentrated in vacuum obtaining 13.44 g of pure product (HPLC:96.2%, ee: +99%).

$^1$H-NMR (ppm): 10.1, 1H, s; 8.85, 1H, dd; 8.30, 1H, dd; 8.15, 1H, d; 8.07, 1H, d; 7.75, 1H, d; 7.65, 2H, d; 7.60, 2H, d; 7.53, 1H, dd; 7.41, 1H, d; 7.09, 1H, d; 6.51, 1H, d; 2.25, 3H, s.

Example 4

Preparation of Enantiomerically-Pure Potassium-7-[(R)-[(4-methylpyrimidin-2-yl)amino][4-(trifluoromethyl)phenyl]methyl]quinolin-8-olate 10 g (24.4 mmol) of neutral compound according to Example 2 was dissolved in 60 ml of ethanol, then a solution of 2.73 g (24.4 mmol) of potassium tert-butoxide in ethanol (60 ml) was added drop-wise. After 1 hour stirring 360 ml of methylcyclohexane was added and the alcohol was evaporated off in reduced pressure. After 16 hours stirring the precipitated crystals were filtered to get 6.09 g of pure product (13.6 mmol, HPLC: 98.1%, ee: +99%).

$^1$H-NMR (ppm): 9.97, 1H, s; 8.43, 1H, dd; 8.07, 1H, d; 7.87, 1H, dd; 7.76, 2H, d; 7.51, 2H, d; 7.24, 1H, d; 7.14, 1H, dd; 6.39, 1H, d; 6.38, 1H, d; 6.15, 1H, d; 3.38, 1H, s; 2.21, 3H, s.

$^{13}$C-NMR (ppm): 161.5, 160.3, 150.0, 145.3, 139.8, 138.0, 129.6, 128.5, 127.3, 124.6, 122.7, 121.0, 109.8, 107.6, 67.0, 56.6, 25.1, 23.7

Example 5

Preparation of Enantiomerically-Pure Potassium-7-[(S)-[(4-methylpyrimidin-2-yl)amino][4-(trifluoromethyl)phenyl]methyl]quinolin-8-olate 6.12 g (13.9 mmol) of neutral compound according to Example 3 was dissolved in 17 ml of ethanol, then a solution of 1.56 g (13.9 mmol) of potassium tert-butoxide in ethanol (9 ml) was added drop-wise. After 1 hour stirring 55 ml of methylcyclohexane was added, then the alcohol was evaporated off in reduced pressure and after 16 hours stirring the precipitated crystals were filtered to get 5.08 g of pure product (13.6 mmol, HPLC: 98.1%, ee: +99%).

$^1$H-NMR (ppm): 9.97, 1H, s; 8.43, 1H, dd; 8.07, 1H, d; 7.87, 1H, dd; 7.76, 2H, d; 7.51, 2H, d; 7.24, 1H, d; 7.14, 1H, dd; 6.39, 1H, d; 6.38, 1H, d; 6.15, 1H, d; 3.38, 1H, s; 2.21, 3H, s.

$^{13}$C-NMR (ppm): 161.5, 160.3, 150.0, 145.3, 139.8, 138.0, 129.6, 128.5, 127.3, 124.6, 122.7, 121.0, 109.8, 107.6, 67.0, 56.6, 25.1, 23.7

Example 6

Preparation of Enantiomerically-Pure Sodium 7-[(R)-[(4-methylpyrimidin-2-yl)amino][4-(trifluoromethyl)phenyl]methyl]quinolin-8-olate 0.50 g (1.22 mmol) of neutral compound according to Example 2 was dissolved in 5 ml of ethanol, then this solution was added drop-wise to 1 ml (1.22 mmol) of ethanol solution of sodium ethoxide (28 mg Na+1 ml ethanol). After 1 hour stirring 360 ml of methylcyclohexane was added, then the alcohol was evaporated off in reduced pressure and after 16 hours stirring the precipitated crystals were filtered, and 408 mg (0.94 mmol) pure product was obtained.

Example 7

Preparation of Enantiomer-Pure 7-[(R)-[(4-Methylpyrimidin-2-yl)amino][4-(trifluoromethyl)phenyl]methyl]quinolin-8-ol fumarate 22.6 g (55.0 mmol) of neutral compound according to Example 2 was dissolved in 30 ml of ethanol, then a solution of 3.2 g (27.5 mmol) of fumaric acid in ethanol (90 ml) was added drop-wise. After 16 hours stirring the precipitated crystals were filtered to get 16.8 g of pure product (35.9 mmol, HPLC: 98.1%, ee: 99.4%).

$^1$H-NMR (ppm): 8.86, 1H, d; 8.30, 1H, dd; 8.15, 1H, d; 8.06, 1H, d; 7.74, 1H, d; 7.65, 2H, d; 7.59, 2H, d; 7.55, 1H, dd; 7.41, 1H, d; 7.07, 1H, d; 6.63, 1H, s; 6.51, 1H, d; 2.25, 3H, s.

$^{13}$C-NMR (ppm): 167.4, 165.9, 161.5, 149.5, 148.3, 148.1, 138.0, 136.0, 133.9, 127.6, 127.3, 127.1, 126.7, 125.1, 124.5, 121.8, 117.5, 110.3, 51.6

Example 8

Preparation of Enantiomerically-Pure 7-[(S)-[(4-Methylpyrimidin-2-yl)amino][4-(trifluoromethyl) phenyl]methyl]quinolin-8-ol fumarate 9.21 g (22.4 mmol) of neutral compound according to Example 3 was dissolved in 15 ml of ethanol, then a solution of 1.30 g (11.2 mmol) of fumaric acid in ethanol (40 ml) was added drop-wise. After 16 hours stirring the precipitated crystals were filtered to get 8.34 g of pure product (17.8 mmol, HPLC: 98.5%, ee: 99%).

$^1$H-NMR (ppm): 8.86, 1H, d; 8.30, 1H, dd; 8.15, 1H, d; 8.07, 1H, d; 7.74, 1H, d; 7.65, 2H, d; 7.59, 2H, d; 7.55, 1H, dd; 7.41, 1H, d; 7.07, 1H, d; 6.63, 1H, s; 6.51, 1H, d; 2.25, 3H, s.

$^{13}$C-NMR (ppm): 167.4, 165.9, 161.5, 149.5, 148.3, 148.1, 138.0, 136.0, 133.9, 127.6, 127.3, 127.1, 126.7, 125.1, 124.5, 121.8, 117.5, 110.3, 51.6

Example 9

Preparation of Enantiomerically-Pure 7-[(R)-[(4-Methylpyrimidin-2-yl)amino][4-(trifluoromethyl) phenyl]methyl]quinolin-8-ol zinc complex 1.098 g (5.0 mmol) of zinc acetate dihydrate was dissolved in 150 ml of tetrahydrofuran, then a solution of 4.104 g (10 mmol) of neutral compound according to Example 2 in tetrahydrofuran (150 ml) was added drop-wise. To the mixture obtained 300 ml of hexane was added drop-wise.

After 16 hours stirring the precipitated crystals were filtered to get 2.73 g (3.09 mmol) of pure product.

$^1$H-NMR (ppm): 8.80, 1H, d; 8.75, 1H, s; 8.32, 1H, d; 8.16, 1H, d; 7.75, 2H, d; 7.58, 2H, d; 7.50, 2H, d; 6.85, 1H, d; 6.58, 1H, d; 6.48, 1H, d; 3.60, 1H, t; 2.28, 3H, s; 1.75, 1H, s.

$^{13}$C-NMR (ppm): 161.5, 160.3, 150.0, 145.3, 139.8, 138.0, 129.6, 128.5, 127.3, 124.6, 122.7, 121.0, 109.8, 107.6, 67.0, 56.6, 25.1, 23.7.

Example 10

Preparation of Enantiomerically-Pure 7-[(R)-[(6-Methylpyridin-2-yl)amino]4-nitrophenyl)methyl]-quinolin-8-ol In inert atmosphere into 18 ml of acetonitrile 1.622 g (5.0 mmol, 0.5 eq) of quinidine, 0.387 g (8.4 mmol, 0.84 eq) of formic acid, 1.091 g (10 mmol, 1.0 eq) of 2-amino-6-methylpyridine, 4.379 g (29 mmol, 3.7 eq) of 4-nitrobenzaldehyde, and finally 1.742 g (12 mmol, 1.2 eq) of 8-hydroxyquinoline were added.

The mixture was stirred at room temperature for four days. The reaction mixture was processing up as given above to get the product as pure R-enantiomer (HPLC: 98.9%, ee: 99%).

$C_{22}H_{18}N_4O_3$(MS: 386.1); HPLC (Chiralpak ADn-Hexane/IPA/TEA=90/10/0.1): Tr=10.30 min. 1H NMR (DMSO-$d_6$) δ 2.2 (3H, s, $CH_3$), 6.37 (1H, d, J=7.0 Hz), 6.49 (1H, d, J=7.9 Hz), 6.98 (1H, d, J=8.8 Hz, NHCH), 7.28 (1H, t, J=7.9 Hz), 7.40 (2H, t, J=7.9 és 8.8 Hz), 7.50-7.55 (1H, m), 7.59-7.66 (3H, m), 8.16 (2H, d, J=8.8 Hz), 8.28 (1H, d, J=7.9 Hz), 10.1 (1H, wide s, OH); $^{13}$C NMR (DMSO-$d_6$) δ 24.2 ($CH_3$), 51.5 (CH), 105.6 (CH), 111.6 (CH), 117.7 (CH), 121.9 (CH), 123.5 (2×CH), 124.5 (Cq), 126.7 (CH), 127.7 (Cq), 128.2 (2×CH), 136.1 (CH), 137.3 (CH), 138.2 (Cq), 146.2 (Cq), 148.4 (CH), 149.8 (Cq), 152.0, 155.7 and 157.3 (Cq)

Example 11

Preparation of Enantiomerically-Pure 7-[(S)-[(6-Methylpyridin-2-yl)amino]4-nitrophenyl)methyl]-quinolin-8-ol In inert atmosphere into 30 ml of acetonitrile 1.8 g (5.5 mmol, 0.7 eq) of quinine, 0,305 g (6.6 mmol, 0.8 eq) of formic acid, 2.20 g (20 mmol, 2.0 eq) of 2-amino-6-methylpyridine, 4.38 g (29 mmol, 3.7 eq) of 4-nitrobenzaldehyde, and finally 1.15 g (7.9 mmol, 1.0 eq) of 8-hydroxyquinoline were added.

The mixture was stirred at room temperature for six days. The reaction mixture was processing up as given above to get the product as pure S-enantiomer (HPLC:98.9%, ee: 99%).

$C_{22}H_{18}N_4O_3$(MS: 386.1); HPLC (Chiralpak ADn-Hexane/IPA/TEA=90/10/0.1): Tr=10.30 min. 1H NMR (DMSO-$d_6$) δ 2.2 (3H, s, $CH_3$), 6.37 (1H, d, J=7.0 Hz), 6.49 (1H, d, J=7.9 Hz), 6.98 (1H, d, J=8.8 Hz, NHCH), 7.28 (1H, t, J=7.9 Hz), 7.40 (2H, t, J=7.9 és 8.8 Hz), 7.50-7.55 (1H, m), 7.59-7.66 (3H, m), 8.16 (2H, d, J=8.8 Hz), 8.28 (1H, d, J=7.9 Hz), 10.1 (1H, wide s, OH); $^{13}$C NMR (DMSO-$d_6$) δ 24.2 ($CH_3$), 51.5 (CH), 105.6 (CH), 111.6 (CH), 117.7 (CH), 121.9 (CH), 123.5 (2×CH), 124.5 (Cq), 126.7 (CH), 127.7 (Cq), 128.2 (2×CH), 136.1 (CH), 137.3 (CH), 138.2 (Cq), 146.2 (Cq), 148.4 (CH), 149.8 (Cq), 152.0, 155.7 and 157.3 (Cq)

Example 12

Preparation of Enantiomerically-Pure 7-[(R)-[(6-Methylpyridin-2-yl)amino]3-hydroxyphenyl)-methyl]quinolin-8-ol In inert atmosphere into 18 ml of acetonitrile 1.622 g (50 mmol, 0.5 eq) of quinidine, 0.387 g (8.4 mmol, 0.84 eq) of formic acid, 1.091 g (10 mmol, 1.0 eq) of 2-amino-6-methylpyridine, 3.538 g (29 mmol, 3.7 eq) of 3-hydroxybenzaldehyde, and finally 1.742 g (12 mmol, 1.2 eq) of 8-hydroxyquinoline were added.

The mixture was stirred at reflux temperature of the solvent for 16 hours. The reaction mixture was processing up as given above to get the product as pure R-enantiomer (HPLC:98.9%, ee: 99%).

$C_{22}H_{18}N_4O_3$(MS: 357); HPLC (Chiralpak AD n-Hexane/IPA/TEA=90/10/0.1): Tr=8.90 min.

Example 13

Preparation of Enantiomerically-Pure 7-[(S)-[(6-Methylpyridin-2-yl)amino]3-hydroxyphenyl)-methyl]quinolin-8-ol In inert atmosphere into 30 ml of acetonitrile 1.8 g (5.5 mmol, 0.7 eq) of quinine, 0.305 g (6.6 mmol, 0.8 eq) of formic acid, 2.2 g (20 mmol, 2.0 eq) of 2-amino-6-methyl-pyridine, 3.538 g (29 mmol, 3.7 eq) of 3-hydroxybenzalde-hyde, and finally 1.15 g (7.9 mmol, 1.0 eq) of 8-hydroxy-quinoline were added.

The mixture was stirred at reflux temperature of the solvent for six days. The reaction mixture was processing up as given above to get the product as pure S-enantiomer (HPLC:98.9%, ee: 99%).

$C_{22}H_{18}N_4O_3$ (MS: 357); HPLC (Chiralpak AD n-Hexane/IPA/TEA=90/10/0.1): Tr=17.18 min.

Example 14

Preparation of Enantiomerically-Pure 7-[(R)-[(6-Methylpyridin-2-yl)amino]3-methoxyphenyl)-methyl]quinolin-8-ol In inert atmosphere into 18 ml of acetonitrile 1.622 g (50 mmol, 0.5 eq) of quinidine, 0.387 g (8.4 mmol, 0.84 eq) of formic acid, 1.091 g (10 mmol, 1.0 eq) of 2-amino-6-methylpyridine, 1.52 g (10 mmol, 1.0 eq) of 4-hydroxy-3-methoxy-benzaldehyde, and finally 1.742 g (12 mmol, 1.2 eq) of 8-hydroxyquinoline were added.

The mixture was stirred at reflux temperature of the solvent for 16 hours. The reaction mixture was processing up as given above to get the product as pure R-enantiomer (HPLC: 95%, ee: 99%).

$C_{22}H_{18}N_4O_3$ (MS=387); HPLC (Chiralpak AD n-Hexane/IPA/TEA=90/10/0.1): Tr=8.61 min.

Example 15

Preparation of Enantiomerically-Pure 7-[(S)-[(6-Methylpyridin-2-yl)amino]3-methoxyphenyl)-methyl]quinolin-8-ol In inert atmosphere into 30 ml of acetonitrile 1.8 g (5.5 mmol, 0.7 eq) of quinine, 0.305 g (6.6 mmol, 0.8 eq) of formic acid, 2.2 g (20 mmol, 2.0 eq) of 2-amino-6-methyl-pyridine, 4.408 g (29 mmol, 3.7 eq) of 4-hydroxy-3-methoxy-benzaldehyde, and finally 1.15 g (7.9 mmol, 1.0 eq) of 8-hydroxyquinoline were added.

The mixture was stirred at reflux temperature of the solvent for six days. The reaction mixture was processing up as given above to get the product as pure S-enantiomer (HPLC:95%, ee: 99%).

$C_{22}H_{18}N_4O_3$ (MS=387); HPLC (Chiralpak AD n-Hexane/IPA/TEA=90/10/0.1): Tr=11.14 min.

Example 16

Preparation of Enantiomerically-Pure 7-[(R)-[(6-Methylpyridin-2-yl)amino](5-bromopyridin-2-yl)methyl]quinolin-8-ol Using 8-hydroxyquinoline, 5-bromopyridine-2-carbalde-hyde, 2-amino-6-methylpyridine and quinidine, pure R-enantiomer was obtained according to the general R-process (HPLC: +99%, ee: +99%).

$C_{21}H_{17}BrN_4O$ (MS=421); HPLC (Lux 5u Cellulose-4, 100*4.6 n-Hexane/IPA/TEA=90/10/0.1): Tr=5.20 min.

Example 17

Preparation of Enantiomerically-Pure 7-[(S)-[(6-Methylpyridin-2-yl)amino](5-bromopyridin-2-yl)methyl]quinolin-8-ol Using 8-hydroxyquinoline, 5-bromopyridine-2-carbalde-hyde, 2-amino-6-methylpyridine and quinine, pure R-enantiomer was obtained according to the general S-process (HPLC: +99%, ee: +99%).

$C_{21}H_{17}BrN_4O$ (MS=421); HPLC (Lux 5u Cellulose-4, 100*4.6 n-Hexane/IPA/TEA=90/10/0.1): Tr=6.56 min.

Example 18

Preparation of Enantiomerically-Pure 7-[(R)-[(6-Methylpyridin-2-yl)amino]2-hydroxyphenyl)-methyl]quinolin-8-ol Using 8-hydroxyquinoline, 2-hydroxybenzaldehyde, 2-amino-6-methylpyridine and quinidine, pure R-enantiomer was obtained according to the general R-process (HPLC: +99%, ee: +99%).

$C_{22}H_{19}N_3O_2$ (MS=357); HPLC (Lux 5u Cellulose-4, 100*4.6 n-Hexane/IPA/TEA=90/10/0.1): Tr=2.39 min.

Example 19

Preparation of Enantiomerically-Pure 7-[(S)-[(6-Methylpyridin-2-yl)amino]2-hydroxyphenyl)-methyl]quinolin-8-ol Using 8-hydroxyquinoline, 2-hydroxybenzaldehyde, 2-amino-6-methylpyridine and quinine, pure S-enantiomer was obtained according to the general S-process (HPLC: +99%, ee: +99%).

$C_{22}H_{19}N_3O_2$ (MS=357); HPLC (Lux 5u Cellulose-4, 100*4.6 n-Hexane/IPA/TEA=90/10/0.1): Tr=7.04 min.

Example 20

Preparation of Enantiomerically Pure 5-Chloro-7-[(R)-[(4-methylpyrimidin-2-yl)amino][4-(trifluorom-ethyl)phenyl]methyl]quinolin-8-ol In inert atmosphere 3 ml of acetonitrile, 540 mg (1.67 mmol, 0.5 eq) of quinidine, 129 mg (2.8 mmol, 0.84 eq) of formic acid, 364 mg (3.33 mmol, 1.0 eq) of 2-amino-4-methylpyrimidine then 580 mg (3.33 mmol, 1.0 eq) of 4-(trifluoromethyl)benzaldehyde, and finally 716 mg (4 mmol, 1.2 eq) 5-chloro-8-hydroxyquinoline were added into a round bottom flask.

The mixture was stirred for 6 days at 75° C. temperature.
The reaction mixture was processing up as usual to get the pure product.

$C_{22}H_{16}ClF_3N_4O$; mass (ESI positive mode): 445 (444+ H$^+$). HPLC (Lux4; Hexane:Isopropanol 95:5) Tr=22.8 minute.

1H NMR (500 MHz, D6MSO) δ 10.43 (wide s, 1H), 8.95-8.91 (m, 1H), 8.47-8.42 (m, 1H), 8.20 (d, J=9.6 Hz, 1H), 8.15 (d, J=4.9 Hz, 1H), 7.71-7.66 (m, 1H), 7.65 (d, J=8.2 Hz, 2H), 7.58 (d, J=8.1 Hz, 2H), 7.09 (1H, d, J=9.5 Hz), 6.51 (1H, d, J=4.95 Hz), 2.24 (3H, s); $^{13}$C-NMR (125

MHz, D6MSO): 25.5, 110.5, 118.8, 123.0, 125.0, 125.3, 125.4, 126.6, 127.8, 132.5, 138.7, 147.5, 149.2, 149.4, 161.5.

Example 21

Preparation of Enantiomerically Pure 5-Chloro-7-[(S)-[(4-methylpyrimidin-2-yl)amino][4-(trifluoromethyl)phenyl]methyl]quinolin-8-ol In inert atmosphere 3 ml of acetonitrile, 540 mg (1.67 mmol, 0.5 eq) of quinine, 129 mg (2.8 mmol, 0.84 eq) of formic acid, 364 mg (3.33 mmol, 1.0 eq) of 2-amino-4-methylpyrimidine then 580 mg (3.33 mmol, 1.0 eq) of 4-(trifluoromethyl)benzaldehyde, and finally 716 mg (4 mmol, 1.2 eq) 5-chloro-8-hydroxyquinoline were added into a round bottom flask.

The mixture was stirred for 6 days at 75° C. temperature.
The reaction mixture was processing up as usual to get the pure product.

$C_{22}H_{16}ClF_3N_4O$; mass (ESI positive mode): 445 (444+H$^+$). HPLC (Lux4; Hexane:Isopropanol 95:5) Tr=22.8 minute.

1H NMR (500 MHz, D6MSO) δ 10.43 (wide s, 1H), 8.95-8.91 (m, 1H), 8.47-8.42 (m, 1H), 8.20 (d, J=9.6 Hz, 1H), 8.15 (d, J=4.9 Hz, 1H), 7.71-7.66 (m, 1H), 7.65 (d, J=8.2 Hz, 2H), 7.58 (d, J=8.1 Hz, 2H), 7.09 (1H, d, J=9.5 Hz), 6.51 (1H, d, J=4.95 Hz), 2.24 (3H, s); $^{13}$C-NMR (125 MHz, D6MSO): 25.5, 110.5, 118.8, 123.0, 125.0, 125.3, 125.4, 126.6, 127.8, 132.5, 138.7, 147.5, 149.2, 149.4, 161.5.

Example 22

Preparation of Enantiomerically Pure 5-Chloro-7-[(R)-[(6-methylpyridin-2-yl)amino][4-(trifluoromethyl)phenyl]methyl]quinolin-8-ol In inert atmosphere 3 ml of acetonitrile, 540 mg (1.67 mmol, 0.5 eq) of quinidine, 129 mg (2.8 mmol, 0.84 eq) of formic acid, 364 mg (3.33 mmol, 1.0 eq) of 2-amino-6-picoline then 580 mg (3.33 mmol, 1.0 eq) of 4-(trifluoromethyl)benzaldehyde, and finally 716 mg (4 mmol, 1.2 eq) 5-chloro-8-hydroxyquinoline were added into a round bottom flask.

The mixture was stirred for 6 days at 75° C. temperature.
The reaction mixture was processing up as usual to get the pure product.

$C_{23}H_{17}ClF_3N_3O$; mass (ESI positive mode): 444 (443+H$^+$).

Example 23

Preparation of Enantiomerically Pure 2-Methyl-7-[(R)-[(4-methylpyrimidin-2-yl)amino][4-(trifluoromethyl)phenyl]methyl]quinolin-8-ol In inert atmosphere 3 ml of acetonitrile, 540 mg (1.67 mmol, 0.5 eq) of quinidine, 129 mg (2.8 mmol, 0.84 eq) of formic acid, 364 mg (3.33 mmol, 1.0 eq) of 2-amino-4-methylpyrimidine then 580 mg (3.33 mmol, 1.0 eq) of 4-(trifluoromethyl)benzaldehyde, and finally 636 mg (4 mmol, 1.2 eq) 8-hydroxyquinaldine were added into a round bottom flask.

The mixture was stirred for 6 days at 75° C. temperature.
The reaction mixture was processing up as usual to get the pure product.

$C_{23}H_{19}F_3N_4O$, mass (ESI positive mode): 425 (424+H$^+$)

Example 24

Preparation of Enantiomerically Pure 2-Methyl-7-[(S)-[(4-methylpyrimidin-2-yl)amino][4-(trifluoromethyl)phenyl]methyl]quinolin-8-ol In inert atmosphere 3 ml of acetonitrile, 540 mg (1.67 mmol, 0.5 eq) of quinine, 129 mg (2.8 mmol, 0.84 eq) of formic acid, 364 mg (3.33 mmol, 1.0 eq) of 2-amino-4-methylpyrimidine then 580 mg (3.33 mmol, 1.0 eq) of 4-(trifluoromethyl)benzaldehyde, and finally 636 mg (4 mmol, 1.2 eq) 8-hydroxyquinaldine were added into a round bottom flask.

The mixture was stirred for 6 days at 75° C. temperature.
The reaction mixture was processing up as usual to get the pure product.

$C_{23}H_{19}F_3N_4O$, mass (ESI positive mode): 425 (424+H$^+$)

Example 25

Preparation of Enantiomerically Pure 2-[(Dimethylamino)methyl]-7-[(R)-[(4-methylpyrimidin-2-yl)amino][4-(trifluoromethyl)phenyl]methyl]quinolin-8-ol In inert atmosphere 3 ml of acetonitrile, 540 mg (1.67 mmol, 0.5 eq) of quinidine, 129 mg (2.8 mmol, 0.84 eq) of formic acid, 364 mg (3.33 mmol, 1.0 eq) of 2-amino-4-methylpyrimidine then 580 mg (3.33 mmol, 1.0 eq) of 4-(trifluoromethyl)benzaldehyde, and finally 808 mg (4 mmol, 1.2 eq) 2-((dimethylamino)methyl)quinolin-8-ol were added into a round bottom flask.

The mixture was stirred for 6 days at 75° C. temperature.
The reaction mixture was processing up as usual to get the pure product.

$C_{25}H_{24}F_3N_5O$; mass (ESI positive mode): 468 (467+H$^+$)

Example 26

Preparation of Enantiomerically Pure 2-[(Dimethylamino)methyl]-7-[(S)-[(4-methylpyrimidin-2-yl)amino][4-(trifluoromethyl)phenyl]methyl]quinolin-8-ol In inert atmosphere 3 ml of acetonitrile, 540 mg (1.67 mmol, 0.5 eq) of quinine, 129 mg (2.8 mmol, 0.84 eq) of formic acid, 364 mg (3.33 mmol, 1.0 eq) of 2-amino-4-methylpyrimidine then 580 mg (3.33 mmol, 1.0 eq) of 4-(trifluoromethyl)benzaldehyde, and finally 808 mg (4 mmol, 1.2 eq) 2-[(dimethylamino)methyl]quinolin-8-ol were added into a round bottom flask.

The mixture was stirred for 6 days at 75° C. temperature.
The reaction mixture was processing up as usual to get the pure product.

$C_{25}H_{24}F_3N_5O$; mass (ESI positive mode): 468 (467+H$^+$)

Example 27

Preparation of Enantiomerically Pure 2-[(Dimethylamino)methyl]-7-[(R)-[(4-methylpyridin-2-yl)amino][4-(trifluoromethyl)phenyl]methyl]quinolin-8-ol In inert atmosphere 3 ml of acetonitrile, 540 mg (1.67 mmol, 0.5 eq) of quinidine, 129 mg (2.8 mmol, 0.84 eq) of formic acid, 364 mg (3.33 mmol, 1.0 eq) of 2-amino-4-picoline then 580 mg (3.33 mmol, 1.0 eq) of 4-(trifluoromethyl)benzaldehyde, and finally 808 mg (4 mmol, 1.2 eq) 2-[(dimethylamino)methyl]quinolin-8-ol were added into a round bottom flask.

The mixture was stirred for 6 days at 75° C. temperature.

The reaction mixture was processing up as usual to get the pure product.

$C_{26}H_{25}F_3N_4O$; tömeg (ESI positive mode): 467 (466+H$^+$)

Example 28

Preparation of Enantiomerically Pure 2-[(Dimethylamino)methyl]-7-[(S)-[(4-methylpyridin-2-yl)amino] [4-(trifluoromethyl)phenyl]methyl]quinolin-8-ol In inert atmosphere 3 ml of acetonitrile, 540 mg (1.67 mmol, 0.5 eq) of quinine, 129 mg (2.8 mmol, 0.84 eq) of formic acid, 364 mg (3.33 mmol, 1.0 eq) of 2-amino-4-picoline then 580 mg (3.33 mmol, 1.0 eq) of 4-(trifluoromethyl)benzaldehyde, and finally 808 mg (4 mmol, 1.2 eq) 2-[(dimethylamino)methyl]quinolin-8-ol were added into a round bottom flask.

The mixture was stirred for 6 days at 75° C. temperature.

The reaction mixture was processing up as usual to get the pure product.

$C_{26}H_{25}F_3N_4O$; mass (ESI positive mode): 467 (466+H$^+$)

Example 29

Preparation of Enantiomerically Pure 5-Nitro-7-[(R)-[(4-methylpyrimidin-2-yl)amino]20 [4-(trifluoromethyl)phenyl]methyl]quinolin-8-ol Using 5-nitro-8-hydroxyquinoline, 4-(trifluoromethyl)benzaldehyde, 2-amino-4-methylpyrimidine and quinidine, pure R-enantiomer was obtained according to the general R-process (HPLC: +99%, ee: +99%).

$C_{22}H_{16}F_3N_5O_3$; mass (ESI positive mode): 456 (455+H$^+$)

Example 30

Preparation of Enantiomerically Pure 5-Nitro-7-[(S)-[(4-methylpyrimidin-2-yl)amino]30 [4-(trifluoromethyl)phenyl]methyl]quinolin-8-ol Using 5-nitro-8-hydroxyquinoline, 4-(trifluoromethyl)benzaldehyde, 2-amino-4-methylpyrimidine and quinine, pure S-enantiomer was obtained according to the general S-process (HPLC: +99%, ee: +99%).

$C_{22}H_{16}F_3N_5O_3$; mass (ESI positive mode): 456 (455+H$^+$)

Example 31

Preparation of Enantiomerically Pure 7-[(R)-[(Pyridin-2-yl) [4-(trifluoromethyl)phenylamino]methyl] quinolin-8-ol Using 8-hydroxyquinoline, 4-(trifluoromethyl)aniline, 2-pyridine-carbaldehyde and quinidine, pure R-enantiomer was obtained according to the general R-process.

$C_{22}H_{16}F_3N_3O$; mass (ESI positive mode): 396 (395+H$^+$)

Example 32

Preparation of Enantiomerically Pure 7-[(S)-[(Pyridin-2-yl) [4-(trifluoromethyl)phenylamino]methyl] quinolin-8-ol Using 8-hydroxyquinoline, 4-(trifluoromethyl)aniline, 2-pyridine-carbaldehyde and quinine, pure S-enantiomer was obtained according to the general S-process.

$C_{22}H_{16}F_3N_3O$; mass (ESI positive mode): 396 (395+H$^+$)

Example 33

Preparation of Enantiomerically Pure 2-(Hydroxymethyl)-7-[(R)-[(4-methylpyrimidin-2-yl)amino][4-(trifluoromethyl)phenyl]methyl]quinolin-8-ol Using 2-hydroxymethyl-8-hydroxyquinoline, 4-(trifluoromethyl)benzaldehyde, 2-amino-4-methylpyrimidine and quinidine, pure R-enantiomer was obtained according to the general R-process.

$C_{23}H_{19}F_3N_4O_2$; mass (ESI positive mode) 441 (440+H$^+$)

Example 34

Preparation of Enantiomerically Pure 2-(Hydroxymethyl)-7-[(R)-[(4-methylpyrimidin-2-yl)amino][4-(trifluoromethyl)phenyl]methyl]quinolin-8-ol Using 2-hydroxymethyl-8-hydroxyquinoline, 4-(trifluoromethyl)benzaldehyde, 2-amino-4-methylpyrimidine and quinine, pure S-enantiomer was obtained according to the general S-process.

$C_{23}H_{19}F_3N_4O_2$; mass (ESI positive mode) 441 (440+H$^+$)

VII. Biological Examples: In Vitro Procedures

Example 35

Inhibition of Matrix Metalloproteinase 2 (MMP-2, 72 kDa Gelatinase), Matrix Metalloproteinase 8 (MMP-8), Matrix Metalloproteinase 10 (MMP-10), Matrix Metalloproteinase 12 (MMP-12), Matrix Metalloproteinase 13 (MMP-13), and Matrix Metalloproteinase 14 (MMP-14) Activity with Compounds 7-[(R)-[(4-Methylpyrimidine-2-yl)amino][4-(trifluoromethyl)phenyl]methyl]quinoline-8-ol and 7-[(S)-[(4-Methylpyrimidine-2-yl)amino][4-(trifluoromethyl)phenyl]methyl]quinoline-8-ol According to Examples 2 and 3

Different matrix metalloproteinase activities were investigated in a set of fluorophotometric, biochemical measurements. Recombinant matrix metalloproteinase enzymes were pre-incubated at 37° C. with different concentrations (25 μM-195 nM) of compounds 7-[(R)-[(4-Methylpyrimidine-2-yl)amino][4-(trifluoromethyl)phenyl]methyl]quinoline-8-ol and 7-[(S)-[(4-Methylpyrimidine-2-yl)amino][4-(trifluoromethyl)phenyl]methyl]quinoline-8-ol according to Examples 2 and 3.

Cleavage of the applied substrate resulted in a fluorescently active molecule which was measured one hour after reaction start with a Wallac Victor microtiter plate reader by using 355 nm extinction and 460 nm emission filters. Enzyme activities were compared to controls which were not treated with the inhibitor, and are given as percentages.

Figure 5:
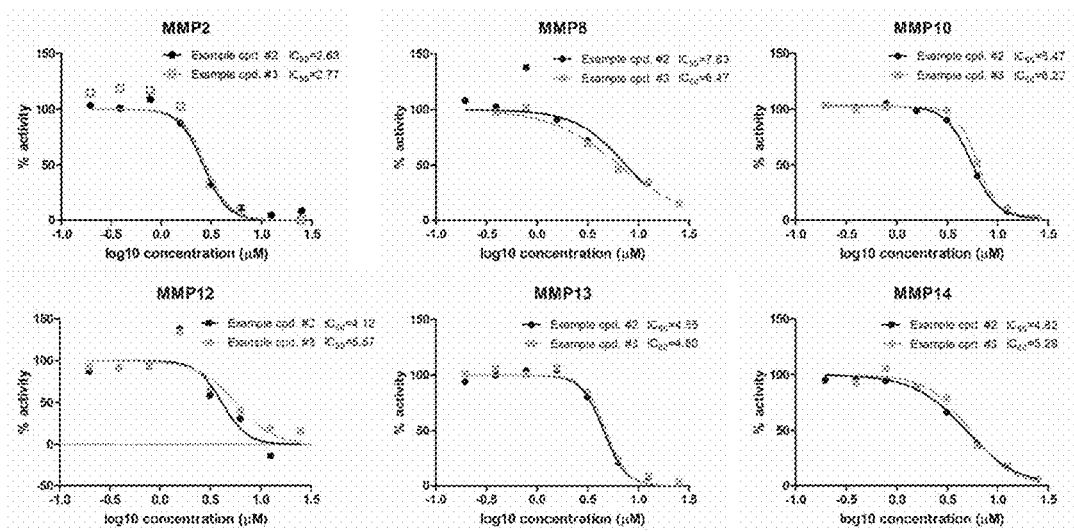

FIG. 5 shows the activity of the six investigated MMP enzymes being dependent on concentrations of compounds according to Examples 2 and 3. According to the $IC_{50}$ values (half maximal inhibitory concentrations) shown in the figure, the R- and S-enantiomers inhibited activities of the investigated enzymes to a similar extent.

Example 36

Treatment with the compound 7-[(R)-[(4-Methylpyrimidine-2-yl)amino][4-(trifluoromethyl)phenyl] methyl]quinoline-8-ol According to Example 2 for Inhibition of $H_2O_2$-Induced Cell Death of Cardiac Muscle Cells In Vitro Cell line H9c2 (ATCC, Rockville, 10MD, USA), derived from embryonic rat heart, was cultured in Dulbecco's Modified Eagle Medium containing 10% bovine serum, 4 mM L-glutamine (Sigma-Aldrich, Hungary), 100 U/ml penicillin, and 100 μg/ml streptomycin. Cells were cultured in 100 mm TC-treated culture dishes (Orange Scientific, Belgium) in an incubator set at 37° C. and 5% $CO_2$ with humid air. For real-time monitoring of cell viability, a Roche xCELLigence SP and DP (ACEA-Roche, Hungary) was used, which gives us information about cell viability on the basis of changes in cell conductivity. Prior to plating, the special 96-well e-plate was covered with 0.2% type I collagen, and then placed into the incubator for 30 min. Cell-free baseline impedance was measured once in a minute for 10 min. After plating (6000 cells/well), measuring began. Treatment of cells was always carried out the morning after plating. Measurement proceeded for 72 h.

Results are shown in FIG. 6. Curve 1 refers to untreated control, curve 2. to control treated with $H_2O_2$, curve 3, 4, 5, 6 refer to different concentrations (3: 0.11 μM compound according to Example 2+900 μM of $H_2O_2$, 4: 0.33 μM compound according to Example 2+900 μM of $H_2O_2$, 5: 1 μM compound according to Example 2+900 μM of $H_2O_2$, 6: 3 μM compound according to Example 2+900 μM of $H_2O_2$) of the compound according to Example 2 (7-[(R)-[(4-Methylpyrimidine-2-yl)amino][4-(trifluoromethyl)phenyl] methyl]quinoline-8-ol). B: refers to percentage of viability at 6 and 24 h after treatment, compared to control cells.

Example 37

Treatment with the Compound 7-[(R)-[(4-Methylpyrimidine-2-yl)amino][4-(trifluoromethyl)phenyl] methyl]quinoline-8-ol According to Example 2 for Inhibition of $H_2O_2$-Induced Cell Death of SH-SY5Y Human Neuroblastoma Cells In Vitro SH-SY5Y cells (ATCC, Rockville, 10MD, USA) were cultured in 100 mm TC-treated culture dishes (Orange Scientific, Belgium) in an incubator set at 37° C. and 5% $CO_2$ with humid air. For real-time monitoring of cell viability, a Roche xCELLigence SP and DP (ACEA-Roche, Hungary) was used, which gives us information about cell viability on the basis of changes in cell conductivity. For plating, DMEM (Dulbecco's Modified Eagle Medium) supplemented with 10% FBS was used. Prior to plating, the special 96-well e-plate was covered with 0.2% type I collagen, and then placed into the incubator for 30 min. Cell-free baseline impedance was measured once in a minute for 10 min. After plating (20.000 cells/well), measuring began. Treatment of cells was always carried out the morning after plating. Measurement proceeded for 72 h.

Results are shown in FIG. 7 Curve 1 refers to untreated control, curve 2 to control treated with $H_2O_2$, curve 3, 4, 5, 6 refer to different concentrations (3: 0.11 μM compound according to Example 2+500 μM of $H_2O_2$, 4: 0.33 μM compound according to Example 2+500 μM of $H_2O_2$, 5: 1 μM compound according to Example 2+500 μM of $H_2O_2$, 6: 3 μM compound according to Example 2+500 μM of $H_2O_2$) of the compound according to Example 2 (7-[(R)-[(4-Methylpyrimidine-2-yl)amino][4-(trifluoromethyl)phenyl] methyl]quinoline-8-ol). B: refers to percentage of viability at 6 and 24 h after treatment, compared to control cells.

Example 38

Treatment with the Compound 7-[(S)-[(4-Methylpyrimidine-2-yl)amino][4-(trifluoromethyl)phenyl] methyl]quinoline-8-ol According to Example 3 for Inhibition of $H_2O_2$-Induced Cell Death of Cardiac Muscle Cells In Vitro Cell line H9c2 (ATCC, Rockville, 10MD, USA), derived from embryonic rat heart, was cultured in Dulbecco's Modified Eagle Medium containing 10% bovine serum, 4 mM L-glutamine (Sigma-Aldrich, Hungary), 100 U/ml penicillin, and 100 μg/ml streptomycin. Cells were cultured in 100 mm TC-treated culture dishes (Orange Scientific, Belgium) in an incubator set at 37° C. and 5% $CO_2$ with humid air. For real-time monitoring of cell viability, a Roche xCELLigence SP and DP (ACEA-Roche, Hungary) was used, which gives us information about cell viability on the basis of changes in cell conductivity. Prior to plating, the special 96-well e-plate was covered with 0.2% type I collagen, and then placed into the incubator for 30 min. Cell-free baseline impedance was measured once in a minute for 10 min. After plating (6000 cells/well), measuring began. Treatment of cells was always carried out the morning after plating. Measurement proceeded for 72 h.

Results are shown in FIG. 8. Curve 1. refers to untreated control, curve 2. to control treated with $H_2O_2$, curve 3, 4, 5, 6 refer to different concentrations (3: 0.11 μM compound according to Example 3+900 μM of $H_2O_2$, 4: 0.33 μM compound according to Example 3+900 μM of $H_2O_2$, 5: 1 μM compound according to Example 3+900 μM of $H_2O_2$, 6: 3 μM compound according to Example 3+900 μM of $H_2O_2$) of the compound according to Example 3. (7-[(S)-[(4-Methylpyrimidine-2-yl)amino][4-(trifluoromethyl)phenyl] methyl]quinoline-8-ol). B: refers to percentage of viability at 6 and 24 h after treatment, compared to control cells.

Example 39

Treatment with the Compound 7-[(S)-[(4-Methylpyrimidine-2-yl)amino][4-(trifluoromethyl)phenyl] methyl]quinoline-8-ol According to Example 3 for Inhibition of $H_2O_2$-Induced Cell Death of SH-SY5Y Human Neuroblastoma Cells In Vitro SH-SY5Y cells (ATCC, Rockville, 10MD, USA) were cultured in 100 mm TC-treated culture dishes (Orange Scientific, Belgium) in an incubator set at 37° C. and 5% $CO_2$ with humid air. For real-time monitoring of cell viability, a Roche xCELLigence SP and DP (ACEA-Roche, Hungary) was used, which gives us information about cell viability on the basis of changes in cell conductivity. For plating, DMEM (Dulbecco's Modified Eagle Medium) supplemented with 10% FBS was used. Prior to plating, the special 96-well e-plate was covered with 0.2% type I collagen, and then placed into the incubator for 30 min. Cell-free baseline impedance was measured once in a minute for 10 min. After plating (20.000 cells/well), measuring began. Treatment of cells was always carried out the morning after plating. Measurement proceeded for 72 h.

Results are shown in FIG. 9 Curve 1. refers to untreated control, curve 2 to control treated with $H_2O_2$, curve 3, 4, 5, 6 refer to different concentrations (3: 0.11 µM compound according to Example 3+500 µM of $H_2O_2$, 4: 0.33 µM compound according to Example 3+500 µM of $H_2O_2$, 5: 1 µM compound according to Example 3+500 µM of $H_2O_2$, 6: 3 µM compound according to Example 3+500 µM of $H_2O_2$) of the compound according to Example 3 (7-[(S)-[(4-Methylpyrimidine-2-yl)amino][4-(trifluoromethyl)phenyl]methyl]quinoline-8-ol). B: refers to percentage of viability at 6 and 24 h after treatment, compared to control cells.

Example 40

Treatment with the Compound Potassium-7-[(R)-[(4-Methylpyrimidine-2-yl)amino][4-(trifluoromethyl)phenyl]methyl]quinoline-8-olate According to Example 4 for Inhibition of Cell Death Caused by Fibrillar Aggregates of Amyloid Peptides in Primary Cortical Neurons in Vitro Cortical neurons from embryonic day 16-17 Wistar rat fetuses were maintained as previously described [1]. Peptide used: Aβ1-42 (Bachem, ref. H1368, batch #1025459). Oligomer preparation: the preparation of Aβ oligomers was performed according to SynAging standard operating procedures. The oligomeric preparation contains a mixture of stable dimers, trimers and tetramers of Aβ1-42 peptide, as well as monomeric forms of the peptide. The same preparation of oligomers was used for all experimental set-ups and has been previously characterized in terms of oligomer composition, neurotoxicity in vitro as well as induction of cognitive impairment.

Figure 10:
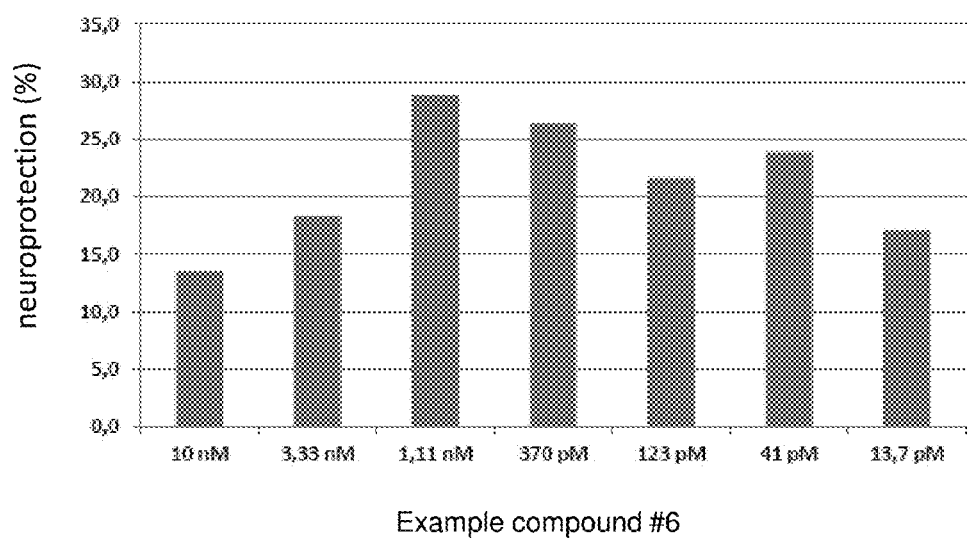

Primary cortical neurons were incubated with increasing concentrations of the compound according to Example 2 in the presence or absence of 1 □M Aβ1-42 oligomers. Following 24 h incubation, neuronal viability was monitored using the calcein-AM assay as previously described [1, 2]. Data shown in FIG. 10 are obtained from 3-4 separate experiments (mean±SEM). Student's t-test (, $p<0.05$, *, $p<0.001$) as well as ANOVA followed by a Scheffe's post hoc test were used to test statistical significance.

Example 41

Treatment with the Compound 7-[(R)-[(4-Methylpyrimidine-2-yl)amino][4-(trifluoromethyl)phenyl]methyl]quinoline-8-ol Zinc Complex According to Example 9 for Inhibition of Cell Death Caused by Fibrillar Aggregates of Amyloid Peptides in Primary Cortical Neurons In Vitro Cortical neurons from embryonic day 16-17 Wistar rat fetuses were maintained as previously described [1]. Peptide used: Aβ1-42 (Bachem, ref. H1368, batch #1025459). Oligomer preparation: the preparation of Aβ oligomers was performed according to SynAging standard operating procedures. The oligomeric preparation contains a mixture of stable dimers, trimers and tetramers of Aβ1-42 peptide, as well as monomeric forms of the peptide. The same preparation of oligomers was used for all experimental set-ups and has been previously characterized in terms of oligomer composition, neurotoxicity in vitro as well as induction of cognitive impairment.

Figure 11:
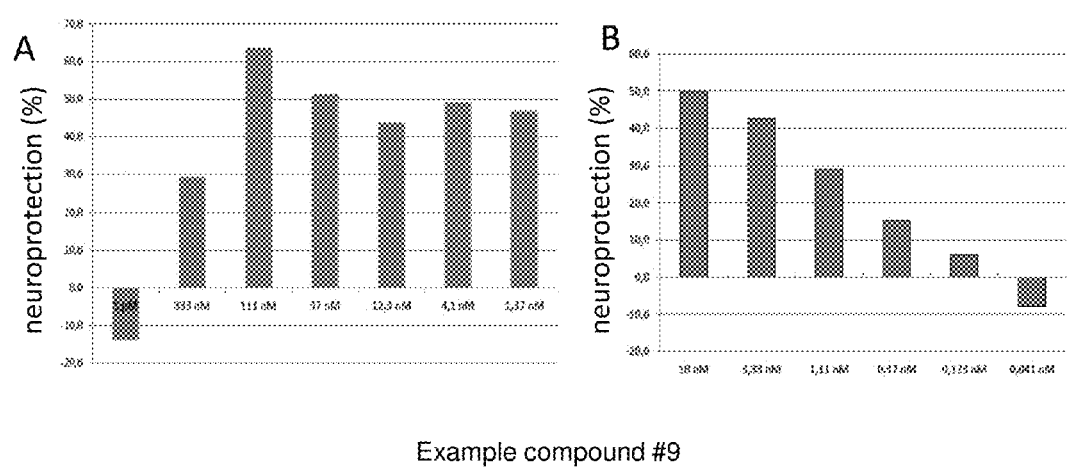
Figure 12:
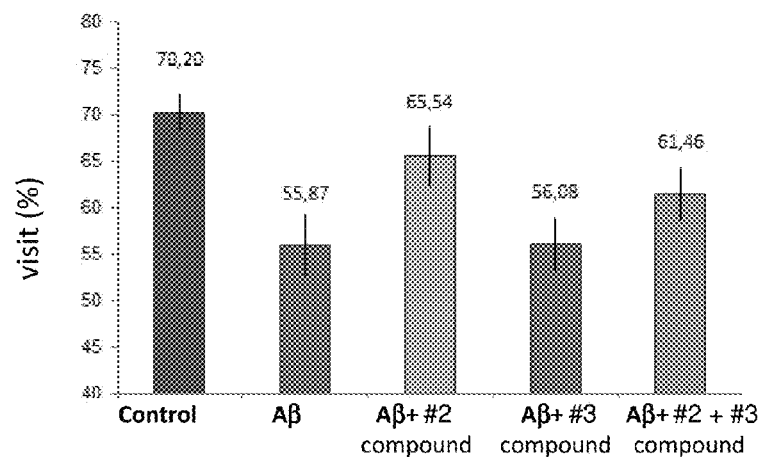

Primary cortical neurons were incubated with increasing concentrations of the compound according to Example 2 in the presence or absence of 1 □M Aβ1-42 oligomers. Following 24 h incubation, neuronal viability was monitored using the calcein-AM assay as previously described [1, 2]. Data shown in FIG. 11. are obtained from 3-4 separate experiments (mean±SEM). Student's t-test (, $p<0.05$, *, $p<0.001$) as well as ANOVA followed by a Scheffe's post hoc test were used to test statistical significance.

VIII. Biological Examples, In Vivo Procedures

In vivo experiments were carried out according to the National Institute of Health guidelines for the care and use of laboratory animals, approved by the French Ministry for Research and Technology. In the course of experiments, animals were housed at a standard temperature (22±1° C.) and in a light-controlled environment (lights on from 7 a.m. to 8 p.m.) with ad libitum access to food and water. Male C57BL/6 mice (C57BL/6J Rj, ref. SC-CJ-12w-M, Janvier, France) were housed 5 animals per cage. From one week before the start of the experiment until the end of the experiment, mice were housed individually. Animals were monitored twice-a-day by laboratory personnel (8 a.m. and 4 p.m.). In this project, young (14 weeks old) as well as aged (15-16 months old) mice were used. Experiments were carried out using 12 mice per experimental group.

Investigation of short-term working memory—Y maze test Y maze tests were carried out as previously described [1, 3]. Prior to testing, mice were brought to the experimental room for at least 30 min to acclimatize to experimental room conditions. The Y maze is made of opaque Plexiglas and each arm is 40 cm long, 16 cm high, 9 cm wide and positioned at equal angles. The apparatus was placed in the test room in such a way that it was brightened homogeneously with 12-15 lux in the arms as well as in the central zone. One mouse at a time was placed at the end of one arm and was allowed to move in the maze freely during a 5 min examination. Each arm entry was recorded with those entries being counted where the mouse completely placed its hind paws in the chosen arm. Alternation was defined as successive entry into the 3 arms on overlapping triplet sets. Results were calculated as the percentage of the ratio of actual detected alternations to possible alternations (defined as the number of total arm entries minus 2).

Example 42

Effects of Treatment with Compounds 7-[(R)-[(4-Methylpyrimidine-2-yl)amino][4-(trifluoromethyl)phenyl]methyl]quinoline-8-ol and 7-[(S)-[(4-Methylpyrimidine-2-yl)amino][4-(trifluoromethyl)phenyl]methyl]quinoline-8-ol According to Example 2 and 3 on Short-Term Memory Impairment Caused by Fibrillar Aggregates of Amyloid Peptides in In Vivo C57BL6/J Mice For the examination of memory impairment caused by Aβ oligomers, a mouse model developed and validated by SynAging was used [1-3]. Mice receiving icy injection of Aβ oligomers develop memory deficits associated with a decrease of hippocampal synaptic protein levels. Under anesthetization, 1 µl of soluble Aβ oligomers (50 pmol) or vehicle (saline) was injected into the right ventricle. The stereotaxic coordinates from the bregma are as follows (in mm): AP-0.22, L-1.0 and D-2.5. For treatments, a 10 ml Hamilton microsyringe fitted with a 26-gauge needle was used. Treatment with molecules described in Example 2. and 3. was carried out once daily for four days with the use of a per os probe (100 µl/animal). Four experimental groups were established: Group A—vehicle/Aβ oligomer, Group B—compound according to Example 2 (4 mg/kg body weight) and Aβ oligomer, Group C—compound according to Example 3 (4 mg/kg body weight) and Aβ oligomer, Group D—compounds from both Example 2. and 3. (4 mg/kg body weight) and Aβ oligomer. At day 4 post Aβ treatment, short-term memory was assessed with the Y maze test.

Treatment with compound 7-[(R)-[(4-Methylpyrimidine-2-yl)amino][4-(trifluoromethyl)phenyl]methyl]quinoline-8-ol according to Example 2 inhibited while treatment with compound 7-[(S)-[(4-Methylpyrimidine-2-yl)amino][4-(trifluoromethyl)phenyl]methyl]quinoline-8-ol) according to Example 3 did not inhibit short-term memory impairment caused by fibrillar aggregates of amyloid peptides in in vivo C57BL6/J mice.

Example 43

Effects of Treatment with Different Concentrations (Related to Body Weight) of Compound 7-[(R)-[(4-Methylpyrimidine-2-yl)amino][4-(trifluoromethyl) phenyl]methyl]quinoline-8-ol According to Example 2 on Short-Term Memory Impairment Caused by Fibrillar Aggregates of Amyloid Peptides in In Vivo C57BL6/J Mice Treatment with Aβ oligomers was carried out as previously described in Example 16. Treatment with the examined compound according to Example 2 was carried out once daily for four days with the use of a per os probe (100 µl/animal). Four experimental groups were established: Group A—vehicle/AS oligomer, Group B—compound according to Example 2. (0.5 mg/kg body weight) and Aβ oligomer, Group C—compound according to Example 2 (2 mg/kg body weight) and Aβ oligomer, Group D—compound according to Example 2 (4 mg/kg body weight) and Aβ oligomer.

Figure 13:
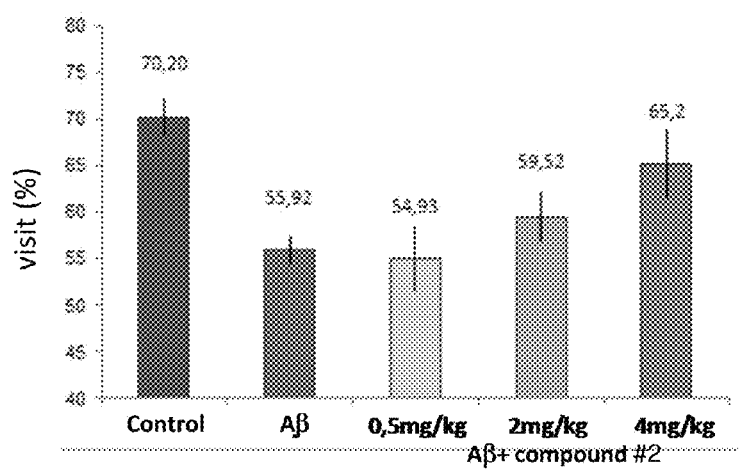

At day 4 post Aβ treatment, short-term memory was assessed with the Y maze test. Results are summarized in FIG. 13.

Treatment with compound 7-[(R)-[(4-Methylpyrimidine-2-yl)amino][4-(trifluoromethyl)phenyl]methyl]quinoline-8-ol according to Example 2 inhibited short-term memory impairment caused by fibrillar aggregates of amyloid peptides in in vivo C57BL6/J mice in a dose-dependent manner.

Example 44

Effect of Compounds 7-[(R)-[(4-Methylpyrimidine-2-yl)amino][4-(trifluoromethyl)phenyl]methyl]quinoline-8-ol and 7-[(S)-[(4-Methylpyrimidine-2-yl) amino][4-(trifluoromethyl)phenyl]methyl]quinoline-8-ol According to Example 2 and 3 on Scopolamine-Induced Short-Term Memory Impairment in In Vivo C57BL6/J Mice Scopolamine has been widely used to induce cognitive deficits (typically short-term memory impairment) in animals [FR4]. Test protocol: 30 min prior to behavioral test, scopolamine (0.6 mg/kg) or vehicle was administered i.p. in control and treated mice (12 mice per experimental groups). Mice were returned to their cage until the start of the test.

Figure 14:
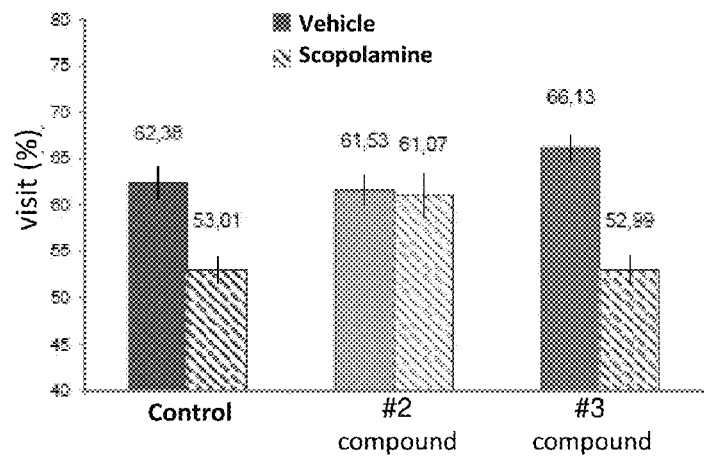

Administration of drug-candidates described in Example 2. and 3. was carried out with a per os gavage (administration time based on PK data). Y-maze tests were carried out as previously described. Results are summarized in FIG. 14.

Treatment with compound 7-[(R)-[(4-Methylpyrimidine-2-yl)amino][4-(trifluoromethyl)phenyl]methyl]quinoline-8-ol according to Example 2 inhibited, while treatment with compound 7-[(S)-[(4-Methylpyrimidine-2-yl)amino][4-(trifluoromethyl)phenyl]methyl]quinoline-8-ol according to Example 3 did not inhibit scopolamine-induced short-term memory impairment in in vivo C57BL6/J mice.

Example 45

Inhibition of the Activity of Caspase 3 Peptidase with Compound 7-[(R)-[(4-Methylpyrimidine-2-yl) amino][4-(trifluoromethyl)phenyl]methyl]quinoline-8-ol According to Example 2

Throughout the experiments, human caspase 3 enzyme produced in *E. coli* was used as previously described (Mittl PRE, Marco S D, Krebs J F, Karanewsky D S, Priestle J P, Tomaselli K J and Grutter M G (1997) Structure of Recombinant Human CPP32 in Complex with the Tetrapeptide Acetyl-Asp-Val-Ala-Asp Fluoromethyl Ketone. J Biol Chem. 272: 6539-6547). In brief: the enzyme (150 U/ml) was pre-incubated together with the compound according to Example 2 (10 µM) in modified HEPES buffer (50 mM HEPES, pH=7.4, 100 mM NaCl, 0.1% CHAPS, 1 mM EDTA, 10% glycerin, 10 mM DTT) for 15 min at 37° C. After the addition of 50 mM Ac-DEVD-AMC substrate, the reaction ran for 60 min. The amount of generated AMC (7-amino-4-methylcoumarine), which gives information about the enzyme activity, was detected by fluorescence at 360/465 nm. At the applied concentration of 10 mM, the compound according to Example 2 reduced the activity of caspase 3 enzyme by 74%.

Example 46

Transcriptional Inhibition of NF-AT (Nuclear Factor of Activated T Cells) Protein with the Compound 7-[(R)-[(4-Methylpyrimidine-2-yl)amino][4-(trifluoromethyl)phenyl]methyl]quinoline-8-ol According to Example 2

Figure 15:
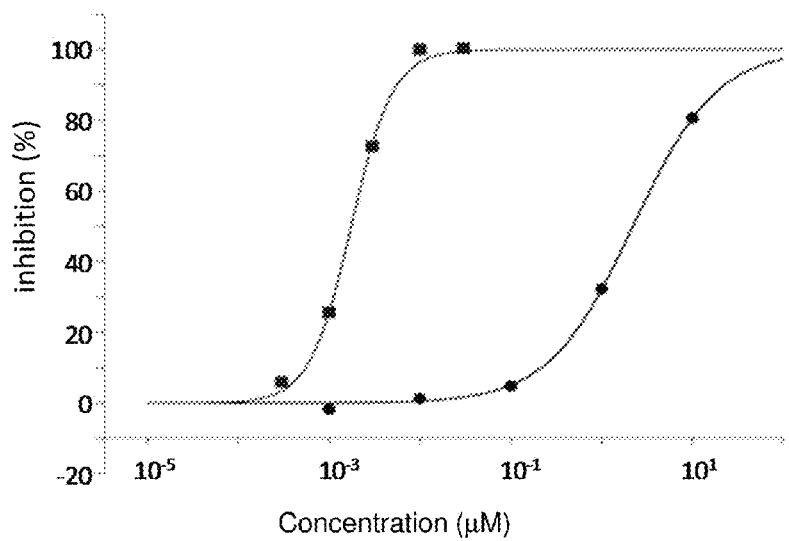

Experiments were carried out on human T Jurkat cells transfected with a reporter construct expressing β-galactosidase and containing the binding site of NFAT1 transcription factor based on the previously described method (Emmel E A, Verweij C L, Durand D B, Higgins K M, Lacy E and Crabtree G R (1989) Cyclosporin A specifically inhibits function of the nuclear proteins involved in T cell activation. Science. 246:1617-1620; Karttunen J and Shastri N (1991) Measurement of ligand-induced activation in single viable T cells using the lacZ reporter gene. Proc Natl Acad Sci USA. 88:3972). Cells ($3 \times 10^6$ cells/ml) were incubated with 10 µM compound according to Example 2 in RPMI-1640 medium (pH=7.4) for 20 min at 37° C. Following this, incubation lasted for an additional 4 h in the presence of 0.5 µM A23187 and 50 ng/ml PMA (12-O-tetradecanoylphorbol-13-acetate). Induced effects can be determined by the β-galactosidase activity of cells treated with the compound according to Example 2 and untreated cells as it catalyzes the transformation of FDG (fluorescein di-β-D-galactopyranoside) into fluorescein. Reading of results was carried out with a SpectraFluor Plus plate reader. Decrease of β-galactosidase activity was compared to the effect of 1 μM cyclosporine A which was served as a positive control. The compound according to Example 2 Reduced the transcriptional activity of NF-AT protein by 2.2 μM half-value concentration. Results are summarized in FIG. 15.

Example 47

Inhibition of 5-Lipoxygenase Enzyme Activity with the Compound 7-[(R)-[(4-Methylpyrimidine-2-yl)amino][4-(trifluoromethyl)phenyl]methyl]quinoline-8-ol According to Example 2

Human 5-lipoxygenase produced by Sf9 cells was used throughout the experiments. The enzyme was pre-incubated with 10 μM compound according to Example 2 at room temperature, then—after the addition of 25 μM arachidonic acid substrate—the amount of generated rhodamine 123 was determined by fluorescence measurement. Percentage of inhibition rate was calculated by comparison to untreated control reactions. In 10 μM concentration the compound according to Example 2 inhibited 5-lipoxygenase activity by 54%.

Example 48

Figure 16:
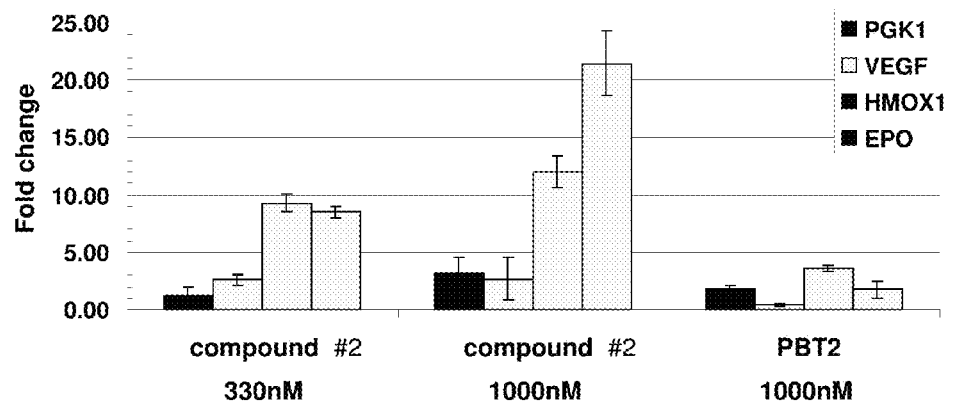

Gene Expression Influencing Effect of the R-Enantiomeric Derivative According to Example 2 on Primary Astrocytes Pure astrocyte culture was obtained from neonatal rats according to the protocol found in literature (Protocols for Neural Cell Culture 2001, pp 117-127. ch 9. Ruth Cole, Jean de Vellis. Preparation of Astrocyte, Oligodendrocyte, and Microglia Cultures from Primary Rat Cerebral Cultures). Astrocytes (1 million) were cultured in 100 mm TC-treated culture dishes (Orange Scientific, Belgium) in an incubator set at 37° C. and 5% $CO_2$ with humid air. The R-enantiomeric derivative according to Example 2 was added to cells in two final concentrations: 330 nM and 1000 nM. Cells were also treated with 1000 nM PBT2 which bears the basic structure of the R-enantiomer according to Example 2 (8-hydroxy-quinoline ring) but contains conformational differences and was developed for the treatment of neurodegenerative disorders (Pub. No.: WO/2004/007461). Treatments were carried out with a 100 μM DMSO-based stock solution. Control cells were treated with the same amount of DMSO without the agent. Each treatment was conducted in three separate culture dishes. After treatment, cells were incubated at 37° C. for 3 h, then the medium was removed, cells were washed with PBS and total RNA was extracted from cells with the Accuzol™ Total RNA Extraction Solution (Bioneer, Daejeon, South Korea), according to the manufacturer's protocol. cDNA transcription was carried out with the High Capacity cDNA Reverse Transcription Kit (Life Technologies, Foster City, Calif., USA). During the test, the expression of four genes (PGK1, EPO, HMOX-1, VEGF) controlled by HIF1a was determined by qRT-PCR, with HPRT gene serving as a control. Relative expression of genes in treated samples was compared to untreated controls. The PCR was conducted with a LightCycler® Nano Instrument (Roche, Budapest, Hungary) in the presence of UPL (Universal Probe Library) probes (HPRT: 95, HMOX1: 4, EPO: 16, VEGF: 1, PGK1: 66), specific primers (HPRT1: 5'-gaccggttctgtcatgtcg-3', HPRT2: 5'-acctggttcatcatcactaat-cac-3'; HMOX1-1: 5'-gtcaagcacagggtgacaga-3', HMOX1-2: 5'-ctgcagctcctcaaacagc-3'; EPO1: 5'-agtcgcgttctggagaggta-3', EPO2: 5'-ccttctgcacagcccatt-3'; VEGF1: 5'-aaaaac-gaaagcgcaagaaa-3', VEGF2: 5'-tttctccgctctgaacaagg-3'; PGK1-1: 5'-ccagataacgaataaccaaagga-3', PGK1-2: 5'-gact-tggctccattgtcca-3') in 20 μl PCR reaction volume with 20 ng cDNA template and 10 μl Lightcycler DNA Probes Master (5×) Reagent Kit (Roche) according to the following protocol: activation of enzyme at 95° C. for 10 min, 50 cycles: denaturation at 95° C. for 15 sec, hybridization and polymerization, then detection at 60° C. for 30 sec. Results are shown in FIG. 16. While the compound according to Example 2 caused dose-dependent and robust activation of EPO and HMOX-1 genes, even 1000 nM of PBT2 did not induced differences in gene activity.

Example 49

Effect of Chronic Treatment with the R-Enantiomeric Derivative According to Example 2 on Erythropoietin Gene Expression in the Hippocampus and Cortex of Aged Animals Twenty-four 18-month-old C57BL/6 female mice (Innovo Ltd., Budapest, Hungary) were divided into two groups randomly: Group 1—untreated control, Group 2—treated with the R-enantiomer according to Example 2, administered in drinking water (20 mg/l) for four months. From both groups, 10-10 mice were sacrificed by $CO_2$ inhalation. After the withdrawal reflex ceased, the whole animal was subjected to perfusion with 1× phosphate buffer according to the described protocol (Whole Animal Perfusion Fixation for Rodents; Gregory J. Gage, Daryl R. Kipke, William Shain; J. Vis. Exp. (65), e3564, doi:10.3791/3564 (2012). After perfusion, brain tissue was removed from the animals and hippocampal and cortical regions were separated. Half of the brain was processed per animal. Half of the samples was used for gene expression studies, the other half was used for protein expression (Example 35) studies.

Figure 17:
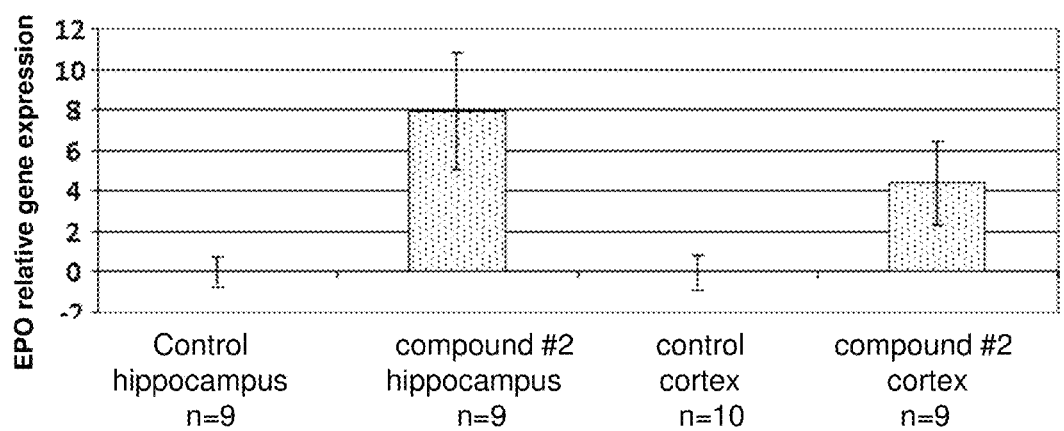

To study gene expression, total RNA was extracted from the brain tissues with Accuzol™ Total RNA Extraction Solution (Bioneer, Daejeon, South Korea), according to the manufacturer's protocol. cDNA transcription was carried out with the High Capacity cDNA Reverse Transcription Kit (Life Technologies, Foster City, Calif., USA). Expression of the gene coding for erythropoietin, the EPO gene was determined by qRT-PCR (with HPRT gene serving as a control) with the method and instrument described in Example 33. but here, mouse-specific UPL probes (HPRT: 95, EPO: 16) and primer pairs were applied (mouse HPRT1: 5'-tcctcctcagaccgctttt-3', mouse HPRT2: 5'-cctggttcat-catcgctaatc-3'; mouse EPO1: 5'-tctgcgacagtcgagttctg-3', mouse EPO2: 5'-cttctgcacaacccatcgt-3'). One hippocampal control, one cortical control and one treated cortical sample did not give appreciable results. Results are shown in FIG. 17. Chronic treatment with the R-enantiomeric derivative according to Example 2 induced both hippocampal and cortical EPO expression compared to samples of untreated control mice.

Example 50

Figure 18:
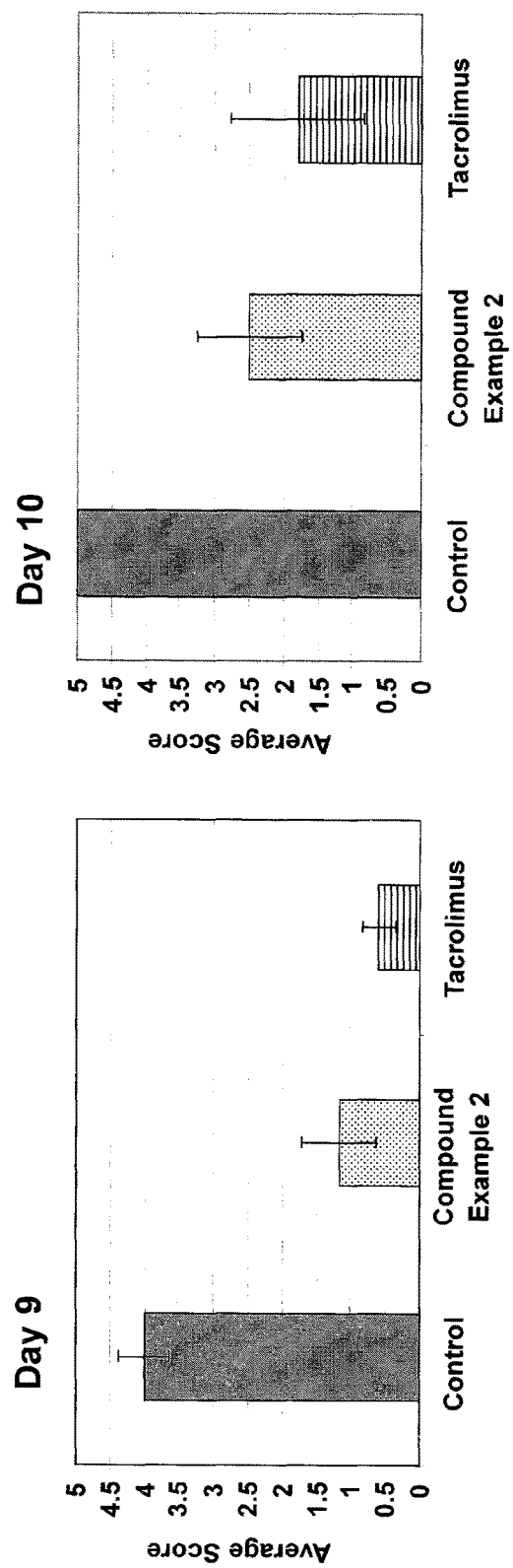

Effect of Chronic Treatment with the R-Enantiomeric Derivative According to Example 2 on Erythropoietin Protein Expression in the Hippocampus and Cortex of Aged Animals Twenty-four 18-month-old female C57BL/6 mice (Innovo Ltd., Budapest, Hungary) were treated according to the experimental setup described in Example 34. in two groups: Group 1—control group given normal drinking water, Group 2—treated with the R-enantiomer according to Example 2, administered in drinking water (20 mg/l) for four months. Brain preparation was carried out under conditions described in Example 34. Brain samples were washed with 1×PBS to remove blood, then tissues were homogenized in 1×PBS and for 3 days, they were held at −20° C. overnight and 25° C. at daytime every day. After the third round of thawing, samples were centrifuged (5 min, 5000 rpm) and the supernatant was collected for further protein expression studies. Determination of erythropoietin levels of samples was done with Quantikine® ELISA Mouse Erythropoetin (R&D Systems, cat. no.: MEPOOB) according to the manufacturer's protocol. At the end of the test, the developed colour was measured with a THERMO-LABSYSTEMS Multiskan FC Absorbance Plate Reader at 450 nm. Results obtained through ELISA and measured at 450 nm were compared to standard dilution series of purified mouse EPO. Values (pg/ml) obtained based on the dilution series were compared to actual protein content of tissues. Protein content of tissue homogenates was measured with Nanodrop-1000 adjusted for BSA protein, at 280 nm. Two hippocampal and two cortical controls as well as one treated hippocampal and cortical sample did not give appreciable results. Results are shown in FIG. 18. Chronic treatment with the R-enantiomeric derivative according to Example 2 induced increased EPO protein levels in both hippocampal and cortical samples compared to samples of untreated control mice.

Example 51

Inhibition of Skin Graft Rejection with the Compound 7-[(R)-[(4-methylpyrimidin-2-yl)amino][4 (trifluoromethyl)phenyl]methyl]quinoline-8-ol according to Example 2

Mouse skin transplantation is a standard method to assay host T cell responses to MHC-disparate donor antigens, which protocol was followed in the present example (Garrod and Cahalan; 2008). Briefly, WT C57BL/6 recipient mice (8-12 weeks old) and WT BALB/c donor mice (8-12 weeks old) were anesthetized with a combination of 10 mg/kg Xylazine and 100 mg/kg Ketamine administered by i.p. injection and 0.05 mg/kg Buprenorphine was administered by subcutaneous injection for analgesia. Ear skin (1.0 cm2) from the WT BALB/c donor mouse was grafted onto the flank of the WT C57BL/6 recipient. The implanted skin (graft) was covered with a sterile bandage, which was removed on day 7 post-transplant.

Recipients received either no treatment (controls), or treated with compound according to Example 2 orally at 5 mg/kg dose, once every day until the end of the experiment from the day of transplantation. As positive control we administered tacrolimus at 5 mg/kg dose, once every day until the end of the experiment from the day of transplantation via intraperitoneal administration.

Different scores were used to define the quality of the grafts: intact grafts (Score 0), early stages of rejection (Score 1-4, corresponding to first clear signals of graft rejection: 1; >25% rejection rate: 2; >50% rejection rate: 3; >75% rejection rate: 4) up to complete graft rejection (Score 5). The different scores describe rejection by the area that was destroyed by the immune system of the host. Scoring was done at day 9 and day 10 post-transplant. Each group contained 6 animals. Average scores with SEM were calculated for each group.

We can see from the results (FIG. 18) that both the positive control, tacrolimus compound as well as the compound according to Example 2 resulted in smaller score values both on day 9 and on day 10, from which we can conclude that both compounds prevented skin graft rejection.

IX. Formulation Examples

Example 52

20 mg of active ingredient, enantiomerically pure 7-[(R)-[(4-methylpyrimidin-2-yl)amino][4-(trifluoromethyl)phenyl]methyl]quinolin-8-ol was mixed with microcrystalline cellulose, mannitol, colloidal anhydrous silicon dioxide and magnesium stearate and the mixture was formulated under pressure, with the usual formulation technic to tablet.

Example 53

20 mg of active ingredient, enantiomerically pure 7-[(R)-[(4-methylpyrimidin-2-yl)amino][4-(trifluoromethyl)phenyl]methyl]quinolin-8-ol was mixed with microcrystalline cellulose, mannitol, colloidal anhydrous silicon dioxide and magnesium stearate and the homogenised mixture was filled into gelatin capsules as solid powder.

REFERENCES

Abdul et al., 2009: Abdul H M, Sama M A, Furman J L, Mathis D M, Beckett T L, Weidner A M, Patel E S, Baig I, Murphy M P, LeVine H 3rd, Kraner S D, Norris C M. Cognitive decline in Alzheimer's disease is associated with selective changes in calcineurin/NFAT signaling. J Neurosci. 2009, 29:12957-12969.

Araboor et al., 2012: Arabpoor Z, Hamidi G, Rashidi B, Shabrang M, Alaei H, Sharifi M R, Salami M, Dolatabadi H R, Reisi P. Erythropoietin improves neuronal proliferation in dentate gyrus of hippocampal formation in an animal model of Alzheimer's disease. Adv Biomed Res. 2012, 1:50.

Asai et al., 1999: Asai A, Qiu Jh, Narita Y, Chi S, Saito N, Shinoura N, Hamada H, Kuchino Y, Kirino T. High level calcineurin activity predisposes neuronal cells to apoptosis. J Biol Chem. 1999, 274:34450-34458.

Bartus, 2000: Bartus, R. T. On neurodegenerative diseases, models, and treatment strategies: lessons learned and lessons forgotten a generation following the cholinergic hypothesis. Exp. Neurol. 2000, 163:495e529.

Bach, 2006: Bach F H. Heme Oxygenase-1 and Transplantation Tolerance Human Immunology 2006, 67:430-432.

Betti, 1900: Betti, M. Gazz. Chim. Ital. 1900, 30 II, 301;

Betti, 1903: Betti, M. Gazz. Chim. Ital. 1903, 33 II, 2;

Bresgen et al., 2003: Bresgen N, Karlhuber G, Krizbai I, Bauer H, et al. Oxidative stress in cultured cerebral endothelial cells induces chromosomal aberrations, micronuclei, and apoptosis, J. Neurosci. Res. 2003 72:327-333.

Britton et al., 2002: Britton R S, Leicester K L, Bacon B R. Iron toxicity and chelation therapy. Int J Hematol. 2002, 76:219-228.

Calabrese et al., 2010: Calabrese V, Butterfield D A, Stella A M, Nutritional antioxidants and the heme oxygenase pathway of stress tolerance: novel targets for neuroprotection in Alzheimer's disease, Ital. J. Biochem. 2003, 52:177-181; Targeting heme oxygenase-1 for neuroprotection and neuroinflammation in neurodegenerative diseases. Jazwa A, Cuadrado A. Curr Drug Targets. 2010, 11:1517-1531.

Chen et al., 2003: Chen K, Gunter K, Maines M D. Neurons overexpressing heme oxygenase-1 resist oxidative stress-mediated cell death, J. Neurochem. 2000, 75:304-313.)

Chong et al., 2013: Chong Z Z, Shang Y C, Mu Y, Cui S, Yao Q, Maiese K. Targeting erythropoietin for chronic neurodegenerative diseases. Expert Opin Ther Targets. 2013, 17:707-720.

Chowdhury et al., 2008: The human oxygen sensing machinery and its manipulation. Chowdhury R, Hardy A, Schofield C J. Chem Soc Rev. 2008, 37:1308-1319.

Chu et al., 2013: Chu J, Li J G, Ceballos-Diaz C, Golde T, Praticò D. The influence of 5-lipoxygenase on Alzheimer's disease-related tau pathology: in vivo and in vitro evidence. Biol Psychiatry. 2013, 74:321-328;

Cole and de Vellis, 2001: Ruth Cole, Jean de Vellis. Preparation of Astrocyte, Oligodendrocyte, and Microglia Cultures from Primary Rat Cerebral Cultures, Protocols for Neural Cell Culture könyv 2001, 9. fejezet, pp 117-127;

De Calignon et al., 2010: de Calignon A, Fox L M, Pitstick R, Carlson G A, Bacskai B J, Spires-Jones T L, Hyman B T. Caspase activation precedes and leads to tangles. Nature. 2010, 464: 1201-1204.

Degterev and Yuan, 2008: Degterev A, Yuan J. Expansion and evolution of cell death programmes. Nat Rev Mol Cell Biol. 2008, 9:378-390.

Eckert et al., 2003: Eckert A, Marques C A, Keil U, Schüssel K, Müller W E. Increased apoptotic cell death in sporadic and genetic Alzheimer's disease. Ann N Y Acad Sci. 2003, 1010:604-609.

Emmel et al., 1991: Emmel E A, Verweij C L, Durand D B, Higgins K M, Lacy E and Crabtree G R (1989) Cyclosporin A specifically inhibits function of the nuclear proteins involved in T cell activation. Science. 246:1617-1620.

Firuzi et al. 2008: Firuzi O, Zhuo J, Chinnici C M, Wisniewski T, Praticò D. 5-Lipoxygenase gene disruption reduces amyloid-beta pathology in a mouse model of Alzheimer's disease. FASEB J. 2008, 22:1169-1178.

Frederickson et al., 2005: Frederickson C J, Koh J Y, Bush A I. The neurobiology of zinc in health and disease. Nat Rev Neurosci. 2005, 6:449-462.

Gage et al., 1999: Gage G J, Kipke D R, Shain W. Whole Animal Perfusion Fixation for Rodents J. Vis. Exp. 2012, (65: e3564;

Frisch M J, et al., 2010: Frisch M J, Trucks G W, Schlegel H B, Scuseria G E et al., Gaussian 09 rev. B01, Gaussian, Inc., Wallingford C T, 2010.

Hagemeyer et al., 2012: Hagemeyer N, Boretius S, Ott C, Von Streitberg A, Welpinghus H, Sperling S, Frahm J, Simons M, Ghezzi P, Ehrenreich H. Erythropoietin attenuates neurological and histological consequences of toxic demyelination in mice. Mol Med. 2012, 18:628-635.

Hengartner, 2000: Hengartner M O. The biochemistry of apoptosis. Nature 2000, 407:770-776;

Hudri et al., 2012: Hudry E, Wu H Y, Arbel-Ornath M, Hashimoto T, Matsouaka R, Fan Z, Spires-Jones T L, Betensky R A, Bacskai B J, Hyman B T. Inhibition of the NFAT pathway alleviates amyloid β neurotoxicity in a mouse model of Alzheimer's disease. J Neurosci. 2012, 32:3176-3192.).

Idris et al., 2008: Idriss N K, Blann A D, Lip G Y. Hemoxygenase-1 in cardiovascular disease. J Am Coll Cardiol. 2008, 52:971-978.

Janciauskiene et al., 1999: Janciauskiene S, Wright H T, Lindgren S. Fibrillar Alzheimer's amyloid peptide Abeta (1-42) stimulates low density lipoprotein binding and cell association, free radical production and cell cytotoxicity in PC12 cells. Neuropeptides. 1999, 33:510-516.

Jazwa and Cuadrado, 2010: Jazwa A, Cuadrado A. Targeting heme oxygenase-1 for neuroprotection and neuroinflammation in neurodegenerative diseases. Curr Drug Targets. 2010, 11:1517-1531.

Karttunen et al. 1991: Karttunen J and Shastri N. Measurement of ligand-induced activation in single viable T cells using the lacZ reporter gene. Proc Natl Acad Sci USA. 1991, 88:3972.

Koh et al., 1996: Koh J Y, Suh S W, Gwag B J, He Y Y, Hsu C Y, Choi D W. The role of zinc in selective neuronal death after transient global cerebral ischemia. Science. 1996, 272:1013-1016.

Korkmaz et al., 2013: Korkmaz S, Barnucz E, Loganathan S, Li S, Radovits T, Hegedus P, Zubarevich A, Hirschberg K, Weymann A, Puskás L G, Ózsvári B, Faragó N, Kanizsai I, Fábián G, Gyuris M, Merkely B, Karck M, Szabó C, Szabó G. Q50, an iron-chelating and zinc-complexing agent, improves cardiac function in rat models of ischemia/reperfusion-induced myocardial injury. Circ J. 2013; 77:1817-1826.

Lewen et al., 2000: Lewén A, Matz P, Chan P H. Free radical pathways in CNS injury. J Neurotrauma. 2000, 17:871-890;

Li et al., 2007: Li C, Hossieny P, Wu B J, Qawasmeh A, Beck K, Stocker R. Pharmacologic induction of heme oxygenase-1. Antioxid Redox Signal. 2007, 9:2227-2239.

Liu et al., 2005: Liu F, Grundke-Iqbal I, Iqbal K, Oda Y, Tomizawa K, Gong C X. Truncation and activation of calcineurin A by calpain I in Alzheimer disease brain. J Biol Chem. 2005, 280:37755-37762.

Lue, et al., 1999: Lue LF1, Kuo Y M, Roher A E, Brachova L, Shen Y, Sue L, Beach T, Kurth J H, Rydel R E, Rogers J. Soluble amyloid beta peptide concentration as a predictor of synaptic change in Alzheimer's disease, AmJ Pathol 1999, 155:853-862.

Lynch et al., 2002: Lynch A M, Lynch M A. The age-related increase in IL-1 type I receptor in rat hippocampus is coupled with an increase in caspase-3 activation. Eur J Neurosci 2002, 15:1779-1788.

Machova et al., 2008: Machova, E., Jakubik, J., Michal, P., Oksman, M., Iivonen, H., Tanila, H., Dolezal, V. Impairment of muscarinic transmission in transgenic APPswe/PS1dE9 mice. Neurobiol. Aging 2008, 29:368e378.

Mammis et al., 2009: Mammis A, McIntosh T K, Maniker A H. Erythropoietin as a neuroprotective agent in traumatic brain injury. Surg Neurol. 2009, 71:527-531.

Mattson, 2006: Mattson M P. Neuronal life-and-death signaling, apoptosis, and neurodegenerative disorders. Antioxid Redox Signal. 2006, 8:1997-2006.

McLean et al., 1999: C. McLean, R. Cherny, F. Fraser, S. Fuller, M. Smith, K. Beyreuther, A. Bush and C. Masters, Soluble pool of Aβ amyloid as a determinant of severity of neurodegeneration in Alzheimer's Disease, Ann Neurol 1999, 46:860-866

Merelli et al., 2011: Merelli A, Caltana L, Lazarowski A, Brusco A. Experimental evidence of the potential use of erythropoietin by intranasal administration as a neuroprotective agent in cerebral hypoxia. Drug Metabol Drug Interact. 2011, 26:65-69.

Merelli et al., 2013: Merelli A, Czornyj L, Lazarowski A. Erythropoietin: a neuroprotective agent in cerebral hypoxia, neurodegeneration, and epilepsy. Curr Pharm Des. 2013, 19:6791-801.

Mittl et al., 1997: Mittl PRE, Marco S D, Krebs J F, Karanewsky D S, Priestle J P, Tomaselli K J and Grutter M G Structure of Recombinant Human CPP32 in Complex with the Tetrapeptide Acetyl-Asp-Val-Ala-Asp Fluoromethyl Ketone. J Biol Chem. 1997, 272: 6539-6547.

Newton et al. 2013: Newton S S, Fournier N M, Duman R S. Vascular growth factors in neuropsychiatry. Cell Mol Life Sci. 2013, 70:1739-1752.

Nguyen et al., 2005: Nguyen T, Hamby A, Massa S M. Clioquinol down-regulates mutant huntingtin expression in vitro and mitigates pathology in a Huntington's disease mouse model. Proc Natl Acad Sci USA. 2005, 102:11840-11845.

Noh et al., 2014: Noh M Y, Cho K A, Kim H, Kim S M, Kim S H. Erythropoietin modulates the immune-inflammatory response of a SOD1(G93A) transgenic mouse model of amyotrophic lateral sclerosis (ALS). Neurosci Lett. 2014, 574:53-58.

Orrenius, 2007: Orrenius S. Reactive oxygen species in mitochondria-mediated cell death. Drug Metab Rev. 2007, 39:443-455.

Palmieri, 2000: Palmieri, G. A Practical o-Hydroxybenzylamines Promoted Enantioselective Addition of Dialkylzincs to Aldehydes with Asymmetric Amplification Tetrahedron Asymmetry 2000, 11:3361.

Phillips et al., 1954: J. P. Phillips, R. W. Keown, Q. Fernando; The reaction of anils with 8-quinolinol., J. Org. Chem. 1954, 19:907.

Phillips and Barrall, 1956: J. P. Phillips, E. M. Barrall. Notes—Betti Reactions of Some Phenols. J. Org. Chem. 1956, 21:692.

Phillips, 1956: J. P. Phillips, The Reactions Of 8-Quinolinol, Chem. Rev. 1956, 56:286.

Regland et al., 2001: Regland B, Lehmann W, Abedini I, Blennow K, Jonsson M, Karlsson I, Sjögren M, Wallin A, Xilinas M, Gottfries C G. Treatment of Alzheimer's disease with clioquinol. Dement Geriatr Cogn Disord. 2001, 12:408-414.

Sama et al., 2008: Sama M A, Mathis D M, Furman J L, Abdul H M, Artiushin I A, Kraner S D, Norris C M. Interleukin-1beta-dependent signaling between astrocytes and neurons depends critically on astrocytic calcineurin/NFAT activity. J Biol Chem. 2008, 283:21953-21964.

Schäfer et al., 2007: Schafer S, Pajonk F G, Multhaup G, Bayer T A. Copper and clioquinol treatment in young APP transgenic and wild-type mice: effects on life expectancy, body weight, and metal-ion levels. J Mol Med (Berl). 2007, 85:405-413.

Smirnova et al., 2010: Smirnova N A, Rakhman I, Moroz N, Basso M, Payappilly J, Kazakov S, Hernandez-Guzman F, Gaisina I N, Kozikowski A P, Ratan R R, Gazaryan I G. Utilization of an in vivo reporter for high throughput identification of branched small molecule regulators of hypoxic adaptation. Chem Biol. 2010, 17:380-391.

Stefanis, 2005: Stefanis L. Caspase-dependent and -independent neuronal death: two distinct pathways to neuronal injury. Neuroscientist. 2005, 11:50-62.

Szabó, 2005: Szabó C. Mechanisms of cell necrosis. Crit Care Med. 2005, 33:S530-534.

Uz et al., 1998: Uz, T., Pesold, C., Longone, P., and Manev, H. Agingassociated up-regulation of neuronal 5-lipoxygenase expression: putative role in neuronal vulnerability. FASEB J. 1998, 12:439-449.

Verkade et al., 2008: Verkade J M M, van Hemert L J C, Quaedflieg P J L M, Rutjes F P J T. Organocatalysed asymmetric Mannich reactions; Chem. Soc. Rev., 2008, 37:29.

Wang et al., 1999: J. Wang, D. W. Dickson, J. Q. Trojanowski and V. M. Lee, The levels of soluble versus insoluble brain Abeta distinguish Alzheimer's disease from normal and pathologic aging, Exp Neurol. 1999, 158:328-337.

Xue et al., 2007: Xue Y Q, Zhao L R, Guo W P, Duan W M. Intrastriatal administration of erythropoietin protects dopaminergic neurons and improves neurobehavioral outcome in a rat model of Parkinson's disease. Neuroscience. 2007, 146:1245-1258.

Zhang et al., 2006: Zhang, C. P., Zhu, L. L., Zhao, T., Zhao, H., Huang, X., Ma, X., Wang, H., and Fan, M. Characteristics of neural stem cells expanded in lowered oxygen and the potential role of hypoxia-inducible factor-1Alpha. Neurosignals 2006, 15:259-265.

Zhou et al., 2006: Zhou, Y., Wei, E. Q., Fang, S. H., Chu, L. S., Wang, M. L., Zhang, W. P., Yu, G. L., Ye, Y. L., Lin, S. C., and Chen, Z. Spatio-temporal properties of 5-lipoxygenase expression and activation in the brain after focal cerebral ischemia in rats. Life Sci. 2006, 79:1645-1656.

Garrod K R, Cahalan M D (2008) Murine skin transplantation. J Vis Exp 11:634.

The invention claimed is:

1. A novel, stereoselective process for the preparation of the novel enantiomeric derivatives of general formulas (I) and (II) and pharmaceutically acceptable salts and complexes with divalent or polyvalent metals thereof,

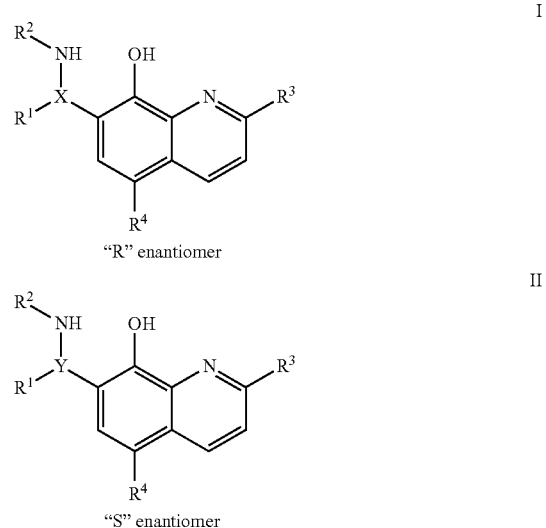

wherein in general formulas (I) and (II):

$R^1$ is a lower alkyl group, lower cycloalkyl group, aryl group, aralkyl group, or six membered heteroaryl or heteroaralkyl group wherein said cyclic groups are optionally substituted at the ortho-, meta- or para position with 1, 2, 3 or 4 are electron withdrawing groups or optionally substituted five membered heteroaryl or heteroaralkyl group wherein the five or six membered heteroaryl or heteroaralkyl groups comprising one, two or three nitrogen, oxygen or sulfur atoms or combinations thereof;

$R^2$ is hydrogen atom, aryl group, or six membered heteroaryl group wherein said cyclic groups are optionally substituted at the ortho, meta or para positions with 1, 2, 3 or 4 electron-withdrawing groups or electron-donating groups or optionally substituted five membered heteroaryl group wherein the five or six membered heteroaryl groups comprising one, two or three nitrogen, oxygen or sulfur atoms or combinations thereof;

R$^3$ is hydrogen, lower alkyl, —CH2F, —CHF2, —CF3, —CH2CH2F, —CH2CHF2, —CH2CF3, —CH2OR$^5$, —CH2CH2OR$^6$, or —CH2-NR7R$^8$;

R$^4$ represents a hydrogen atom, a halogen atom, a methylthio group, methylsulfinyl group, methyl sulfonyl group, or azido group;

R$^5$ is hydrogen or lower alkyl group

R$^6$ is hydrogen or lower alkyl group

R$^7$ is hydrogen or lower alkyl group;

R$^8$ is hydrogen or a lower alkyl group;

R$^7$ and R$^8$ together are —(CH2) n-, or —CH2CH2OCH2CH2-, or —CH2CH2NR9CH2CH2- —CH2CH2SCH2CH2- group or groups;

R$^9$ is a lower alkyl group or COR$^{10}$;

R$^{10}$ is hydrogen, a lower alkyl group or OMe or OMe group n is 4, 5 or 6;

in formula (I) X is a —CH group with "R" configuration at C-atom;

in formula (II) Y is a —CH group with "S" configuration at C-atom, with the proviso that R1 cannot be unsubstituted phenyl group when R2 is a phenyl group unsubstituted or substituted 2-pyridyl group or 2 or 4-carboxyphenyl group;

R3 is methyl or hydrogen,

R4 is hydrogen or chlorine substituents;

as well as

R1 cannot be 3,4-dimethylphenyl group, if

R2 is unsubstituted 2-pyridyl group,

R3 is methyl, and

R4 is hydrogen;

as well as

R1 cannot be 2-furyl group, if

R2 is unsubstituted 2-pyridyl group,

R3 is hydrogen, and

R4 is a chlorine substituent as well as

R1 cannot be an unsubstituted 2-pyridyl group, when R 2 is 5-methylisoxazole-3-yl group R3 is hydrogen R4 is hydrogen, the method comprising:

reacting an 8-hydroxyquinoline derivative of general formula (III)

III with an amine of general formula (IV),

R$^2$—NH2  IV and oxo compounds of formula (V)

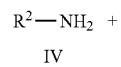
V and in the presence of a quinidine or a quinine catalyst, an acid and a solvent

R$^2$—NH2 + IV

III

V

Procedure "R": solvent/acid
quinidine

Procedure "S": solvent/acid
quinine

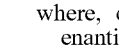
I

II where, depending on the catalyst, the pure R or S enantiomer derivative is formed.

2. The process for preparing the novel R-enantiomeric and S-enantiomeric derivatives of general formulas (I') and (I") and pharmaceutically acceptable salts and complexes with divalent or polyvalent metals thereof

I'

R-enantiomer

-continued

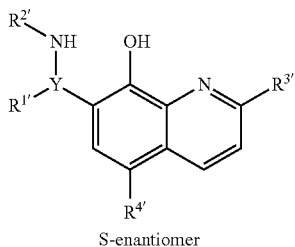

II'

S-enantiomer according to claim 1,
wherein in formulas (I') and (II")
R$^{1'}$ is an aryl group substituted at the meta or para-position with an electron withdrawing group or at the ortho, meta or para position with an electron-donating group or disubstituted at the meta and para or at the ortho and para positions with electron withdrawing groups, or R$^{1'}$ is an unsubstituted or substituted heteroaryl group;
R2' is an aromatic group substituted at the para-position with an electron withdrawing group or R2' is an unsubstituted or substituted aryl or heteroaromatic group, substituted at the ortho-, meta- or para-position with alkyl groups and/or electron withdrawing groups;
R$^{3'}$ is hydrogen;
R$^{4'}$ is hydrogen; and
wherein forming an R enantiomeric derivative with formula (I') is quinidine as the catalyst used, and forming an S enantiomeric derivative is quinine as the catalyst used.

3. The process according to claim 1, wherein the novel enantiomeric derivatives of 8-hydroxyquinoline derivatives, pharmaceutically acceptable salts, complexes with divalent or polyvalent metals thereof is 7-[(R)-[(4-methyl-pyrimidin-2-yl) amino][4-(trifluoromethyl) phenyl] methyl] quinoline-8-ol.

4. The process according to claim 1, wherein the novel enantiomeric derivatives of 8-hydroxyquinoline derivatives, pharmaceutically acceptable salts, complexes with divalent or polyvalent metals thereof, are:
7-[(S)-[(4-methyl-pyrimidin-2-yl) amino] [4-(trifluoromethyl) phenyl] methyl] quinoline-8-ol,
Potassium 7-[(R)-[(4-methyl-pyrimidin-2-yl) amino] [4-(trifluoromethyl) phenyl] methyl] quinoline-8-olate,
Potassium 7-[(S)-[(4-methyl-pyrimidin-2-yl) amino] [4-(trifluoromethyl) phenyl] methyl] quinoline-8-olate,
Sodium 7-[(R)-[(4-methyl-pyrimidin-2-yl) amino] [4-(trifluoromethyl) phenyl] methyl] quinoline-8-olate,
7-[(R)-[(4-methyl-pyrimidin-2-yl) amino] [4-(trifluoromethyl) phenyl] methyl] quinoline-8-ol fumarate salt
7-[(S)-[(4-methyl-pyrimidin-2-yl) amino] [4-(trifluoromethyl) phenyl] methyl] quinoline-8-ol fumarate salt
7-[(R)-[(4-methyl-pyrimidin-2-yl) amino] [4-(trifluoromethyl) phenyl] methyl] quinoline-8-ol zinc complex,
7-[(R)-[(6-methylpyridin-2-yl) amino] (4-nitrophenyl) methyl] quinoline-8-ol,
7-[(S)-[(6-methylpyridin-2-yl) amino] (4-nitrofenilmetil)] quinolin-8-ol,
7-[(R)-[(6-methylpyridin-2-yl) amino] (3-hidroxifenilmetil] quinolin-8-ol,
7-[(S)-[(6-methylpyridin-2-yl) amino]-3-hidroxifenilmetil] quinolin-8-ol,
7-[(R)-[(6-methylpyridin-2-yl) amino] (4-hydroxy-3-methoxyphenyl) methyl] quinoline-8-ol,
7-[(S)-[(6-methylpyridin-2-yl) amino] (4-hydroxy-3-methoxyphenyl) methyl] quinoline-8-ol,
7-[(R)-[(6-methylpyridin-2-yl) amino] (5-brómpiridin-2-yl) methyl] quinolin-8-ol,
7-[(S)-[(6-methylpyridin-2-yl) amino] (5-brómpiridin-2-yl) methyl] quinolin-8-ol,
7-[(R)-[(6-methylpyridin-2-yl) amino] (2-hidroxfenil-metil] quinolin-8-ol,
7-[(S)-[(6-methylpyridin-2-yl) amino] (2-hidroxifenil-metil] quinolin-8-ol
5-chloro-7-[(R)-[(4-methyl-pyrimidin-2-yl) amino] [4-(trifluoromethyl) phenyl] methyl] quinoline-8-ol,
5-chloro-7-[(S)-[(4-methyl-pyrimidin-2-yl) amino] [4-(trifluoromethyl) phenyl) methyl] quinolin-8-ol,
5-chloro-7-[(R)-[(6-methylpyridin-2-yl) amino)] [(4-(trifluoromethyl) phenyl] methyl) quinoline-8-ol,
2-methyl-7-[(R)-[(4-methyl-pyrimidin-2-yl) amino] [4-(trifluoromethyl) phenyl) methyl] quinolin-8-ol,
2-methyl-7-[(S)-[(4-methyl-pyrimidin-2-yl) amino] [4-(trifluoromethyl) phenyl] methyl] quinoline-8-ol,
2-[(dimethylamino) methyl]-7-[(R)-[(4-methyl-pyrimidin-2-yl) amino] [4-(trifluoromethyl) phenyl] methyl] quinoline-8-ol,
2-[(dimethylamino) methyl]-7-[(S)-[(4-methyl-pyrimidin-2-yl) amino] [4-(trifluoromethyl) phenyl] methyl] quinoline-8-ol,
2-[(dimethylamino) methyl]-7-[(R)-[(4-methylpyridin-2-yl) amino] [4-(trifluoromethyl) phenyl] methyl] quinoline-8-ol,
2-[(dimethylamino) methyl]-7-[(S)-[(4-methylpyridin-2-yl) amino] [4-(trifluoromethyl) phenyl] methyl] quinoline-8-ol,
5-nitro-7-[(R)-[(4-methyl-pyrimidin-2-yl) amino] [4-(trifluoromethyl) phenil] methyl] quinoline-8-ol,
5-nitro-7-[(S)-[(4-methyl-pyrimidin-2-yl) amino] [4-(trifluoromethyl) phenil] methyl] quinoline-8-ol,
7-[(R)-(pyridin-2-yl) [4-(trifluoromethyl) phenylamino] methyl] quinoline-8-ol,
7-[(S)-(pyridin-2-yl) [4-(trifluoromethyl) phenylamino] methyl] quinoline-8-ol,
2-(hydroxymethyl)-7-[(R)-[(4-methyl-pyrimidin-2-yl) amino] [4-(trifluoromethyl) phenyl] methyl] quinoline-8-ol,
2-(hydroxymethyl)-7-[(S)-[(4-methyl-pyrimidin-2-yl) amino] [4-(trifluoromethyl) phenyl] methyl] quinoline-8-ol.

5. The process according to claim 2, wherein the novel enantiomeric derivatives of 8-hydroxyquinoline derivatives, pharmaceutically acceptable salts, complexes with divalent or polyvalent metals thereof is 7-[(R)-[(4-methyl-pyrimidin-2-yl) amino] [4-(trifluoromethyl) phenyl] methyl] quinoline-8-ol.

6. The process according to claim 2, wherein the novel enantiomeric derivatives of 8-hydroxyquinoline derivatives, pharmaceutically acceptable salts, complexes with divalent or polyvalent metals thereof, are:
7-[(S)-[(4-methyl-pyrimidin-2-yl) amino] [4-(trifluoromethyl) phenyl] methyl] quinoline-8-ol,
Potassium 7-[(R)-[(4-methyl-pyrimidin-2-yl) amino] [4-(trifluoromethyl) phenyl] methyl] quinoline-8-olate,
Potassium 7-[(S)-[(4-methyl-pyrimidin-2-yl) amino] [4-(trifluoromethyl) phenyl] methyl] quinoline-8-olate,
Sodium 7-[(R)-[(4-methyl-pyrimidin-2-yl) amino] [4-(trifluoromethyl) phenyl] methyl] quinoline-8-olate, 7-[(R)-[(4-methyl-pyrimidin-2-yl) amino] [4-(trifluoromethyl) phenyl] methyl] quinoline-8-ol fumarate salt
7-[(S)-[(4-methyl-pyrimidin-2-yl) amino] [4-(trifluoromethyl) phenyl] methyl] quinoline-8-ol fumarate salt
7-[(R)-[(4-methyl-pyrimidin-2-yl) amino] [4-(trifluoromethyl) phenyl] methyl] quinoline-8-ol zinc complex,
7-[(R)-[(6-methylpyridin-2-yl) amino] (4-nitrophenyl) methyl] quinoline-8-ol,
7-[(S)-[(6-methylpyridin-2-yl) amino] (4-nitrofenilmetil)] quinolin-8-ol,
7-[(R)-[(6-methylpyridin-2-yl) amino] (3-hidroxifenilmetil] quinolin-8-ol,
7-[(S)-[(6-methylpyridin-2-yl) amino]-3-hidroxifenilmetil] quinolin-8-ol,
7-[(R)-[(6-methylpyridin-2-yl) amino] (4-hydroxy-3-methoxyphenyl) methyl] quinoline-8-ol,
7-[(S)-[(6-methylpyridin-2-yl) amino] (4-hydroxy-3-methoxyphenyl) methyl] quinoline-8-ol,
7-[(R)-[(6-methylpyridin-2-yl) amino] (5-brómpiridin-2-yl) methyl] quinolin-8-ol,
7-[(S)-[(6-methylpyridin-2-yl) amino] (5-brómpiridin-2-yl) methyl] quinolin-8-ol,
7-[(R)-[(6-methylpyridin-2-yl) amino] (2-hidroxfenilmetil] quinolin-8-ol,
7-[(S)-[(6-methylpyridin-2-yl) amino] (2-hidroxifenilmetil] quinolin-8-ol
5-chloro-7-[(R)-[(4-methyl-pyrimidin-2-yl) amino] [4-(trifluoromethyl) phenyl] methyl] quinoline-8-ol,
5-chloro-7-[(S)-[(4-methyl-pyrimidin-2-yl) amino] [4-(trifluoromethyl) phenyl) methyl] quinolin-8-ol,
5-chloro-7-[(R)-[(6-methylpyridin-2-yl) amino)] [(4-(trifluoromethyl) phenyl] methyl) quinoline-8-ol,
2-methyl-7-[(R)-[(4-methyl-pyrimidin-2-yl) amino] [4-(trifluoromethyl) phenyl) methyl] quinolin-8-ol,
2-methyl-7-[(S)-[(4-methyl-pyrimidin-2-yl) amino] [4-(trifluoromethyl) phenyl] methyl] quinoline-8-ol,
2-[(dimethylamino) methyl]-7-[(R)-[(4-methyl-pyrimidin-2-yl) amino] [4-(trifluoromethyl) phenyl] methyl] quinoline-8-ol,
2-[(dimethylamino) methyl]-7-[(S)-[(4-methyl-pyrimidin-2-yl) amino] [4-(trifluoromethyl) phenyl] methyl] quinoline-8-ol,
2-[(dimethylamino) methyl]-7-[(R)-[(4-methylpyridin-2-yl) amino] [4-(trifluoromethyl) phenyl] methyl] quinoline-8-ol,
2-[(dimethylamino) methyl]-7-[(S)-[(4-methylpyridin-2-yl) amino] [4-(trifluoromethyl) phenyl] methyl] quinoline-8-ol,
5-nitro-7-[(R)-[(4-methyl-pyrimidin-2-yl) amino] [4-(trifluoromethyl) phenil] methyl] quinoline-8-ol,
5-nitro-7-[(S)-[(4-methyl-pyrimidin-2-yl) amino] [4-(trifluoromethyl) phenil] methyl] quinoline-8-ol,
7-[(R)-(pyridin-2-yl) [4-(trifluoromethyl) phenylamino] methyl] quinoline-8-ol,
7-[(S)-(pyridin-2-yl) [4-(trifluoromethyl) phenylamino] methyl] quinoline-8-ol,
2-(hydroxymethyl)-7-[(R)-[(4-methyl-pyrimidin-2-yl) amino] [4-(trifluoromethyl) phenyl] methyl] quinoline-8-ol,
2-(hydroxymethyl)-7-[(S)-[(4-methyl-pyrimidin-2-yl) amino] [4-(trifluoromethyl) phenyl] methyl] quinoline-8-ol.

* * * * *